(12) United States Patent
Costales et al.

(10) Patent No.: US 8,859,548 B2
(45) Date of Patent: *Oct. 14, 2014

(54) COMPOUNDS AND COMPOSITIONS AS PROTEIN KINASE INHIBITORS

(71) Applicants: Abran Q. Costales, Emeryville, CA (US); Shenlin Huang, San Diego, CA (US); Jeff Xianming Jin, San Ramon, CA (US); Zuosheng Liu, San Diego, CA (US); Sabina Pecchi, Oakland, CA (US); Daniel Poon, Piedmont, CA (US); John Tellew, La Jolla, CA (US); Qiong Zhang, Shanghai (CN)

(72) Inventors: Abran Q. Costales, Emeryville, CA (US); Shenlin Huang, San Diego, CA (US); Jeff Xianming Jin, San Ramon, CA (US); Zuosheng Liu, San Diego, CA (US); Sabina Pecchi, Oakland, CA (US); Daniel Poon, Piedmont, CA (US); John Tellew, La Jolla, CA (US); Qiong Zhang, Shanghai (CN)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/022,540

(22) Filed: Sep. 10, 2013

(65) Prior Publication Data

US 2014/0011825 A1    Jan. 9, 2014

Related U.S. Application Data

(60) Continuation of application No. 13/473,230, filed on May 16, 2012, now Pat. No. 8,563,553, which is a division of application No. 12/862,418, filed on Aug. 24, 2010, now Pat. No. 8,242,260.

(60) Provisional application No. 61/238,083, filed on Aug. 28, 2009, provisional application No. 61/313,061, filed on Mar. 11, 2010.

(51) Int. Cl.
*A61K 31/50* (2006.01)
*A61K 45/06* (2006.01)
*A61K 31/506* (2006.01)
*C07D 403/04* (2006.01)

(52) U.S. Cl.
CPC .............. *C07D 403/04* (2013.01); *A61K 45/06* (2013.01); *A61K 31/506* (2013.01)
USPC ......................................... 514/247

(58) Field of Classification Search
CPC ........................... A61K 31/506; C07D 239/26
USPC ........................................... 514/247
See application file for complete search history.

(56) References Cited

FOREIGN PATENT DOCUMENTS

| GB | 2 306 108 A | 4/1997 |
|----|---|---|
| WO | WO 2009/115572 A2 | 9/2009 |
| WO | WO 2009/137391 A2 | 11/2009 |
| WO | WO 2010/010154 A1 | 1/2010 |

OTHER PUBLICATIONS

Ronald L. Wolin et al. "Dual Binding Site Inhibitors of B-RAF Kinase" *Bioorg. Med. Chem. Lett.* 18:2825-2829, 2008.

*Primary Examiner* — Wu-Cheng Winston Shen
*Assistant Examiner* — Christopher R Stone
(74) *Attorney, Agent, or Firm* — Scott W. Reid

(57) ABSTRACT

The present invention provides compounds of Formula I or II:

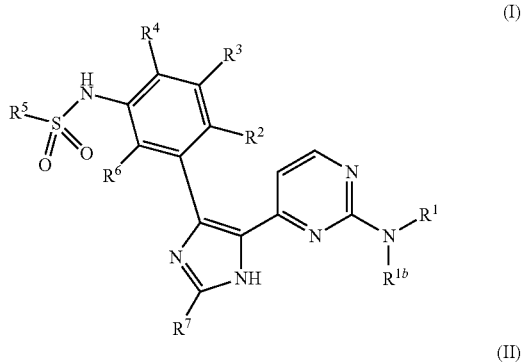

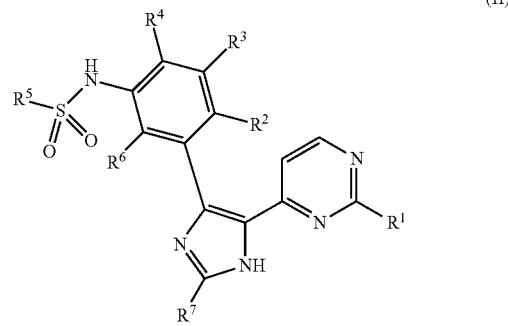

wherein $R^1$, $R^{1b}$, $R^2$, $R^3$, $R^4$, $R^5$, $R^6$ and $R^7$ are defined herein. The compounds of Formula (I) or (II) and pharmaceutical compositions thereof are useful for the treatment of B-Raf-associated diseases.

16 Claims, No Drawings

COMPOUNDS AND COMPOSITIONS AS PROTEIN KINASE INHIBITORS

CROSS-REFERENCE TO RELATED APPLICATIONS

This application is a continuation of U.S. Ser. No. 13/473,230, filed May 15, 2012, which is a divisional of 12/862,418, filed Aug. 24, 2012, which issued as U.S. Pat. No. 8,242,260, and claims the benefit of priority under 35 U.S.C. §119(e) to U.S. provisional application Ser. No. 61/238,083, filed on Aug. 28, 2009, and U.S. provisional application Ser. No. 61/313,061, filed on Mar. 11, 2010, which are incorporated herein by reference in their entirety.

FIELD OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of B-Raf.

BACKGROUND OF THE INVENTION

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor, trkB, Met, and the fibroblast growth factor receptor, FGFR3; non-receptor tyrosine kinases such Abl and the fusion kinase BCR-Ab1, Lck, Csk, Fes, Bmx and c-src; and serine/threonine kinases such as B-Raf, sgk, MAP kinases (e.g., MKK4, MKK6, etc.) and SAPK2α, SAPK2β and SAPK3. Aberrant kinase activity has been observed in many disease states including benign and malignant proliferative disorders as well as diseases resulting from inappropriate activation of the immune and nervous systems.

SUMMARY

Compounds of Formula (I) and (II) below are described herein which have been shown to have Raf kinase activity:

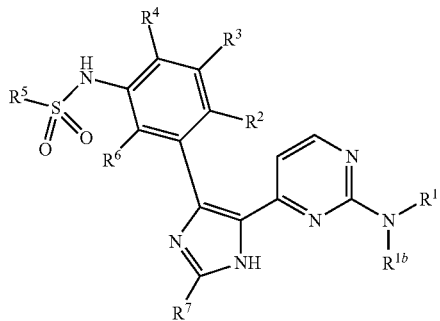

(I)

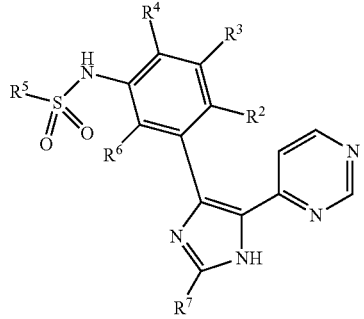

(II)

wherein
R$^1$ is
(i) H,
(ii) (C$_3$-C$_6$) cycloalkyl optionally substituted with cyano;
(iii) (C$_1$-C$_3$) alkyl optionally substituted with cyano, —C(O)NH$_2$, or hydroxy, or
(iv) —X$^1$NHC(O)OR$^{1a}$ or —X$^1$NHC(O)NHR$^{1a}$, where X$^1$ is (C$_1$-C$_4$)alkylene optionally substituted with 1 to 3 groups each independently selected from halo, (C$_1$-C$_4$)alkyl, or halosubstituted(C$_1$-C$_4$)alkyl and R$^{1a}$ is H, (C$_1$-C$_4$)alkyl, or halosubstituted(C$_1$-C$_4$)alkyl;
R$^{1b}$ is H or methyl;
R$^2$ is H or halogen;
R$^3$ is H, halogen, (C$_1$-C$_4$)alkoxy, (C$_1$-C$_4$)alkyl, halosubstituted(C$_1$-C$_4$)alkoxy, or halosubstituted(C$_1$-C$_4$)alkyl;
R$^4$ is halogen, H, or (C$_1$-C$_4$) alkyl;
R$^5$ is (C$_1$-C$_6$)alkyl, (C$_3$-C$_6$)cycloalkyl, (C$_3$-C$_8$)branched alkyl, halosubstituted(C$_1$-C$_6$)alkyl, halosubstituted(C$_3$-C$_8$) branched alkyl, (C$_3$-C$_6$)cycloalkyl(C$_1$-C$_3$)alkylene, or phenyl, where said phenyl is optionally substituted with 1 to 3 substituents each independently selected form halo, CH$_3$, or CF$_3$;
R$^6$ is H, (C$_1$-C$_4$) alkyl, or halogen; and
R$^7$ is H, (C$_1$-C$_6$)alkyl, (C$_3$-C$_6$)cycloalkyl, 1-methyl-(C$_3$-C$_6$) cycloalkyl, 1-(halosubstituted methyl)-(C$_3$-C$_6$)cycloalkyl, —(C$_3$-C$_8$)branched alkyl, halosubstituted(C$_1$-C$_6$)alkyl, halosubstituted(C$_3$-C$_8$)branched alkyl, or phenyl, where said phenyl is optionally substituted with 1 to 3 substituents selected form halogen, (C$_1$-C$_4$)alkyl or halosubstituted(C$_1$-C$_4$)alkyl, preferably R$^7$ is H, (C$_1$-C$_6$)alkyl, (C$_3$-C$_6$)cycloalkyl, 1-methyl-(C$_3$-C$_6$)cycloalkyl, (C$_3$-C$_8$)branched alkyl, or phenyl, where said phenyl is optionally substituted with 1 to 3 substituents selected form halogen, (C$_1$-C$_4$)alkyl or halosubstituted(C$_1$-C$_4$)alkyl; or a pharmaceutically acceptable salt thereof.

In one embodiment, compounds of Formula (I), or a pharmaceutically acceptable salt thereof, is provided.

In one particular embodiment of a compound of Formula I
R$^1$ is
(i) (C$_1$-C$_3$)alkyl optionally substituted with cyano, —C(O)NH$_2$, or hydroxy, or
(ii) —X$^1$NHC(O)OR$^{1a}$, where X$^1$ is (C$_1$-C$_4$)alkylene optionally substituted with 1 to 3 groups each independently selected from halo, (C$_1$-C$_4$)alkyl, or halosubstituted(C$_1$-C$_4$) alkyl and R$^{1a}$ is H, (C$_1$-C$_4$)alkyl, or halosubstituted(C$_1$-C$_4$) alkyl;
R$^2$ is H or halogen;
R$^3$ is H, halogen, (C$_1$-C$_4$)alkoxy, (C$_1$-C$_4$)alkyl, halosubstituted(C$_1$-C$_4$)alkoxy, or halosubstituted(C$_1$-C$_4$)alkyl;
R$^4$ is halogen, H, or (C$_1$-C$_4$)alkyl;

$R^5$ is $(C_1-C_6)$alkyl, $(C_3-C_6)$cycloalkyl, $(C_3-C_8)$branched alkyl, halosubstituted$(C_1-C_6)$alkyl, or halosubstituted$(C_3-C_8)$branched alkyl;

$R^6$ is H, $(C_1-C_4)$alkyl, or halogen; and $R^7$ is H, $(C_1-C_6)$alkyl, $(C_3-C_6)$cycloalkyl, 1-methyl-$(C_3-C_6)$cycloalkyl, 1-(halosubstituted methyl)-$(C_3-C_6)$cycloalkyl, $(C_3-C_8)$branched alkyl, halosubstituted$(C_1-C_6)$alkyl, or halosubstituted$(C_3-C_8)$branched alkyl or phenyl, where said phenyl is optionally substituted with 1 to 3 substituents selected form halogen, $(C_1-C_4)$alkyl or halosubstituted$(C_1-C_4)$alkyl, preferably $R^7$ is H, $(C_1-C_6)$alkyl, $(C_3-C_6)$cycloalkyl, 1-methyl-$(C_3-C_6)$cycloalkyl, or phenyl, where said phenyl is optionally substituted with 1 to 3 substituents selected form halogen, $(C_1-C_4)$alkyl or halosubstituted$(C_1-C_4)$alkyl; or a pharmaceutically acceptable salt thereof.

In one preferred embodiment, compounds of Formula (I) are provided wherein $R^1$ is —$X^1$NHC(O)O$R^{1a}$, where $X^1$ is a $(C_1-C_4)$alkylene optionally substituted with 1 to 3 groups each independently selected from $(C_1-C_4)$alkyl or halosubstituted$(C_1-C_4)$alkyl and $R^{1a}$ is $(C_1-C_2)$alkyl or halosubstituted$(C_1-C_2)$alkyl; $R^2$ is H or F; $R^3$ is H, halogen, $(C_1-C_2)$alkoxy, $(C_1-C_2)$alkyl, halosubstituted$(C_1-C_2)$alkoxy, or halosubstituted$(C_1-C_2)$alkyl; $R^4$ is H or methyl; $R^5$ is $(C_1-C_4)$alkyl, $(C_3-C_6)$cycloalkyl, $(C_3-C_5)$branched alkyl, halosubstituted$(C_1-C_4)$alkyl, or halosubstituted$(C_3-C_6)$branched alkyl; $R^6$ is H, $(C_1-C_2)$alkyl, or halogen; and $R^7$ is $(C_3-C_6)$cycloalkyl, 1-methyl-$(C_3-C_6)$cycloalkyl, or $(C_3-C_6)$branched alkyl; or a pharmaceutically acceptable salt thereof.

In another preferred embodiment, compounds of Formula (I) are provided wherein $R^1$ is —$X^1$NHC(O)O$R^{1a}$, where $X^1$ is a $(C_1-C_4)$alkylene optionally substituted with 1 to 3 groups each independently selected from $(C_1-C_4)$alkyl or halosubstituted$(C_1-C_4)$alkyl and $R^{1a}$ is $(C_1-C_2)$alkyl or halosubstituted$(C_1-C_2)$alkyl; $R^2$ is H or F; $R^3$ is H, halogen, $(C_1-C_2)$alkoxy, $(C_1-C_2)$alkyl, halosubstituted$(C_1-C_2)$alkoxy, or halosubstituted$(C_1-C_2)$alkyl; $R^4$ is H or methyl; $R^5$ is $(C_1-C_4)$alkyl, $(C_3-C_6)$cycloalkyl, $(C_3-C_5)$branched alkyl, halosubstituted$(C_1-C_4)$alkyl, halosubstituted$(C_3-C_6)$branched alkyl, $(C_3-C_6)$cycloalkyl$(C_1-C_3)$alkylene, or phenyl substituted with 1 to 3 substituents each independently selected form Cl, F, $CH_3$, or $CF_3$; $R^6$ is H, $(C_1-C_2)$alkyl, or halogen; and $R^7$ is $(C_3-C_6)$cycloalkyl, 1-methyl-$(C_3-C_6)$cycloalkyl, or $(C_3-C_6)$branched alkyl; or a pharmaceutically acceptable salt thereof.

In another preferred embodiment, compounds of Formula (I) are provided wherein $R^1$ is —$X^1$NHC(O)O$R^{1a}$, where $X^1$ is $(C_1-C_2)$alkylene substituted with $(C_1-C_2)$alkyl and $R^{1a}$ is $(C_1-C_2)$alkyl; $R^2$ is H; $R^3$ is H, Cl, F, methoxy, methyl, or difluoromethoxy; $R^4$ is H; $R^5$ is methyl, cyclopropyl, ethyl, propyl, isopropyl, sec-butyl, isobutyl, trifluoromethyl, or 3,3,3-trifluoropropyl; $R^6$ is H, methyl, F, or Cl; and $R^7$ is t-butyl, cyclopropyl, or 1-trifluoromethylcyclopropyl; or a pharmaceutically acceptable salt thereof.

In another preferred embodiment, compounds of Formula (I) are provided wherein $R^1$ is —$X^1$NHC(O)O$R^{1a}$, where $X^1$ is a $(C_1-C_4)$alkylene optionally substituted with 1 to 3 groups each independently selected from $(C_1-C_4)$alkyl or halosubstituted$(C_1-C_4)$alkyl and $R^{1a}$ is $(C_1-C_2)$alkyl or halosubstituted$(C_1-C_2)$alkyl; $R^2$ is H or F; $R^3$ is H, halogen, $(C_1-C_2)$alkoxy, $(C_1-C_2)$alkyl, halosubstituted$(C_1-C_2)$alkoxy, or halosubstituted$(C_1-C_2)$alkyl; $R^4$ is H or methyl; $R^5$ is $(C_1-C_4)$alkyl, $(C_3-C_6)$cycloalkyl, $(C_3-C_5)$branched alkyl, halosubstituted$(C_1-C_4)$alkyl, halosubstituted$(C_3-C_6)$branched alkyl, or phenyl substituted with F, $CH_3$, or $CF_3$; $R^6$ is H, $(C_1-C_2)$alkyl, or halogen; and $R^7$ is $(C_3-C_6)$cycloalkyl, 1-methyl-$(C_3-C_6)$cycloalkyl, or $(C_3-C_6)$branched alkyl; or a pharmaceutically acceptable salt thereof.

In yet another preferred embodiment, compounds of Formula (I) are provided wherein $R^1$ is —$X^1$NHC(O)O$R^{1a}$, where $X^1$ is $(C_1-C_2)$alkylene substituted with $(C_1-C_2)$alkyl and $R^{1a}$ is $(C_1-C_2)$alkyl; $R^2$ is H; $R^3$ is H, Cl, F, methoxy, methyl, or difluoromethoxy; $R^4$ is H; $R^5$ is methyl, cyclopropyl, ethyl, propyl, isopropyl, sec-butyl, isobutyl, trifluoromethyl, or 3,3,3-trifluoropropyl; $R^6$ is H, methyl, F, or Cl; and $R^7$ is t-butyl, cyclopropyl, or 1-methylcyclopropyl; or a pharmaceutically acceptable salt thereof.

In one embodiment, compounds of Formula (II), or a pharmaceutically acceptable salt thereof.

In a preferred embodiment, compounds of Formula (II) are provided wherein $R^2$ is H or F; $R^3$ is H, halogen, $(C_1-C_2)$alkoxy, $(C_1-C_2)$alkyl, halosubstituted$(C_1-C_2)$alkoxy, or halosubstituted$(C_1-C_2)$alkyl; $R^4$ is H or methyl; $R^5$ is $(C_1-C_4)$alkyl, $(C_3-C_6)$cycloalkyl, $(C_3-C_5)$branched alkyl, halosubstituted$(C_1-C_4)$alkyl, halosubstituted$(C_3-C_6)$branched alkyl, or $(C_3-C_6)$cycloalkyl$(C_1-C_3)$alkylene; $R^6$ is H, $(C_1-C_2)$alkyl, or halogen; and $R^2$ is $(C_3-C_6)$cycloalkyl, 1-methyl-$(C_3-C_6)$cycloalkyl, or $(C_3-C_6)$branched alkyl; or a pharmaceutically acceptable salt thereof.

In another preferred embodiment, compounds of Formula (II) are provided wherein $R^2$ is H; $R^3$ is H, Cl, F, methoxy, methyl, or difluoromethoxy; $R^4$ is H; $R^5$ is methyl, cyclopropyl, ethyl, propyl, isopropyl, sec-butyl, isobutyl, trifluoromethyl, or 3,3,3-trifluoropropyl; $R^6$ is H, methyl, F, or Cl; and $R^7$ is t-butyl, cyclopropyl, or 1-methylcyclopropyl; or a pharmaceutically acceptable salt thereof.

In one preferred embodiment, compounds of Formula (I) or (II) are provided wherein $R^1$ has the following formula (1a)

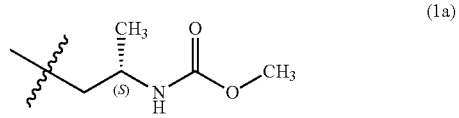

or a pharmaceutically acceptable salt thereof.

Particular compounds of Formula (I) include: (S)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate; (R)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate; (S)-Methyl 1-(4-(2-cyclopropyl-4-(2-fluoro-5-methyl-3-(methylsulfonamido)phenyl)-1H-imidazol-5-yl)pyrimidin-2-ylamino)propan-2-ylcarbamate; (S)-Methyl 1-(4-(2-cyclopropyl-4-(2,5-dichloro-3-(methylsulfonamido)phenyl)-1H-imidazol-5-yl)pyrimidin-2-ylamino)propan-2-ylcarbamate; (S)-Methyl 1-(4-(4-(2-chloro-3-(methylsulfonamido)phenyl)-2-cyclopropyl-1H-imidazol-5-yl)pyrimidin-2-ylamino)propan-2-ylcarbamate; (S)-Methyl 1-(4-(2-cyclopropyl-4-(2-fluoro-3-(methylsulfonamido)phenyl)-1H-imidazol-5-yl)pyrimidin-2-ylamino)propan-2-ylcarbamate; Methyl (2S)-1-(4-(2-cyclopropyl-4-(2,5-difluoro-3-(methylsulfonamido)phenyl)-1H-imidazol-5-yl)pyrimidin-2-ylamino)propan-2-ylcarbamate; and (S)-Methyl 1-(4-(4-(2-chloro-5-methyl-3-(methylsulfonamido)phenyl)-2-cyclopropyl-1H-imidazol-5-yl)pyrimidin-2-ylamino)propan-2-ylcarbamate; or a pharmaceutically acceptable salt thereof. In particular, (S)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate, or a pharmaceutically acceptable salt thereof.

Other particular compounds of Formula (I) include: (S)-Methyl 1-(4-(5-(5-chloro-3-(cyclopropanesulfonamido)-2- fluorophenyl)-2-cyclopropyl-1H-imidazol-4-yl)pyrimidin-2-ylamino)propan-2-ylcarbamate; (S)-Methyl 1-(4-(5-(5-chloro-3-(ethylsulfonamido)-2-fluorophenyl)-2-cyclopropyl-1H-imidazol-4-yl)pyrimidin-2-ylamino) propan-2-ylcarbamate; (S)-Methyl 1-(4-(5-(5-chloro-2-fluoro-3-(3,3,3-trifluoropropylsulfonamido)phenyl)-2-cyclopropyl-1H-imidazol-4-yl)pyrimidin-2-ylamino) propan-2-ylcarbamate; (S)-Methyl 1-(4-(5-(5-chloro-3-(cyclopropylmethylsulfonamido)-2-fluorophenyl)-2-cyclopropyl-1H-imidazol-4-yl)pyrimidin-2-ylamino) propan-2-ylcarbamate; (S)-Methyl 1-(4-(4-(2-chloro-3-(ethylsulfonamido)-5-fluorophenyl)-2-cyclopropyl-1H-imidazol-5-yl)pyrimidin-2-ylamino)propan-2-ylcarbamate; (S)-Methyl 1-(4-(4-(2-chloro-3-(cyclopropanesulfonamido)-5-fluorophenyl)-2-cyclopropyl-1H-imidazol-5-yl)pyrimidin-2-ylamino)propan-2-ylcarbamate; (S)-Methyl 1-(4-(5-(5-chloro-2-fluoro-3-(methylsulfonamido)phenyl)-2-(1-methylcyclopropyl)-1H-imidazol-4-yl)pyrimidin-2-ylamino)propan-2-ylcarbamate; (S)-Methyl 1-(4-(5-(2-fluoro-5-methyl-3-(methylsulfonamido)phenyl)-2-(1-methylcyclopropyl)-1H-imidazol-4-yl)pyrimidin-2-ylamino)propan-2-ylcarbamate; (S)-Methyl 1-(4-(5-(5-chloro-2-fluoro-3-(4-fluorophenylsulfonamido)phenyl)-2-cyclopropyl-1H-imidazol-4-yl)pyrimidin-2-ylamino) propan-2-ylcarbamate; and (S)-Methyl 1-(4-(5-(5-chloro-2-fluoro-3-(3-fluorophenylsulfonamido)phenyl)-2-cyclopropyl-1H-imidazol-4-yl)pyrimidin-2-ylamino) propan-2-ylcarbamate; or a pharmaceutically acceptable salt thereof.

Particular compounds of Formula (II) include N-(2-chloro-3-(2-cyclopropyl-5-(pyrimidin-4-yl)-1H-imidazol-4-yl)-5-fluorophenyl)-2,6-difluorobenzenesulfonamide; N-(2-chloro-3-(2-cyclopropyl-5-(pyrimidin-4-yl)-1H-imidazol-4-yl)-5-fluorophenyl)methanesulfonamide; and N-(2-chloro-3-(2-cyclopropyl-5-(pyrimidin-4-yl)-1H-imidazol-4-yl)-5-fluorophenyl)propane-1-sulfonamide; or a pharmaceutically acceptable salt thereof.

The compounds of the present invention inhibit the activity of B-Raf and are, therefore, expected to be useful in the treatment of B-Raf-associated diseases.

In another aspect of the present invention, a pharmaceutical composition is provided which comprises a compound of Formula (I), or a pharmaceutically acceptable salt thereof, and a diluent, carrier or excipient. The pharmaceutical composition may further comprise an additional therapeutic agent, wherein the additional therapeutic agent is selected from the group consisting of an anticancer compound, an analgesic, an antiemetic, an antidepressant, and an anti-inflammatory agent.

In yet another aspect of the present invention, a method for treating cancer is provided which comprises administering to a subject in need of such treatment a pharmaceutically effective amount of a compound of Formula (I), or a pharmaceutical acceptable salt thereof, or a pharmaceutical composition comprising a compound of Formula (I), or a pharmaceutical acceptable salt thereof, and a diluent, carrier or excipient.

In another aspect of the present invention, a method for treating a condition mediated by Raf kinase which comprises administering to a subject in need thereof an effective amount of a compound of Formula (I), or a pharmaceutical acceptable salt thereof, or a pharmaceutical composition comprising a compound of Formula (I), or a pharmaceutical acceptable salt thereof, and a diluent, carrier or excipient. Preferably, the Raf Kinase being mediated is a mutant b-Raf kinase, more preferably, a mutant b-Raf(V600E) kinase.

The methods may comprise administering an additional therapeutic agent. Preferred additional agents include an anti-cancer drug, a pain medication, an antiemetic, an antidepressant or an anti-inflammatory agent, more preferably, the additional therapeutic agent is a different Raf kinase inhibitor or an inhibitor of MEK, mTOR, PI3K, CDK9, PAK, Protein Kinase C, a MAP kinase, a MAPK Kinase, or ERK.

DEFINITIONS

"Alkyl" as a group and as a structural element of other groups, for example halo-substituted-alkyl and alkoxy, can be either straight-chained or branched. $C_{1-4}$-alkoxy includes, methoxy, ethoxy, and the like. "Halosubstituted alkyl" refers to an alkyl group (branched or unbranched) wherein any of the hydrogens can be substituted with a halogen. Representative examples of halosubstituted-($C_1$-$C_4$)alkyl include fluoromethyl, difluoromethyl, trifluoromethyl, chlorofluoromethyl, difluoroethyl, pentafluoroethyl, and the like. Similarly, hydroxy-substituted-($C_1$-$C_6$)alkyl means and alkyl group (branched or unbranched) wherein any of the hydrogens can be substituted with a hydroxyl. For example, hydroxy-substituted-($C_1$-$C_6$)alkyl includes 2-hydroxyethyl, and the like. Similarly, cyano-substituted-($C_1$-$C_6$)alkyl means and alkyl group (branched or unbranched) wherein any of the hydrogens can be substituted with cyano.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example, ($C_1$-$C_{10}$) heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, ($C_3$-$C_{10}$)cycloalkyl includes cyclopropyl, cyclobutyl, cyclopentyl, cyclohexyl, cycloheptyl, cyclooctyl, cyclononyl, and cyclodecyl. A preferred cycloalkyl is cyclopropyl.

"Heterocycloalkyl" means cycloalkyl where one or more of the ring carbons is replaced by a moiety selected from —O—, —N=, —NR—, —C(O)—, —S—, —S(O)— or —S(O)$_2$—, wherein R is hydrogen, ($C_1$-$C_4$)alkyl or a nitrogen protecting group (—NPg). Representative examples of ($C_3$-$C_8$)heterocycloalkyl include 2H-pyranyl, 4H-pyranyl, piperidinyl, 1,4-dioxane, morpholinyl, 1,4-dithianyl, thiomorpholino, imidazolidin-2-one, tetrahydrofuran, piperazinyl, 1,3,5-trithianyl, pyrrolidinyl, pyrrolidinyl-2-one, piperidinone, 1,4-dioxa-8-aza-spiro[4.5]dec-8-yl, etc.

"Halogen" (or halo) represents chloro, fluoro, bromo or iodo.

"Treat", "treating" and "treatment" refer to a method of alleviating or abating a disease and/or its attendant symptoms.

The term "compounds of the present invention" (unless specifically identified otherwise) refer to compounds of Formula (I) or (II), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Compounds of Formula I can be prepared using the procedure outlined in Scheme I below.

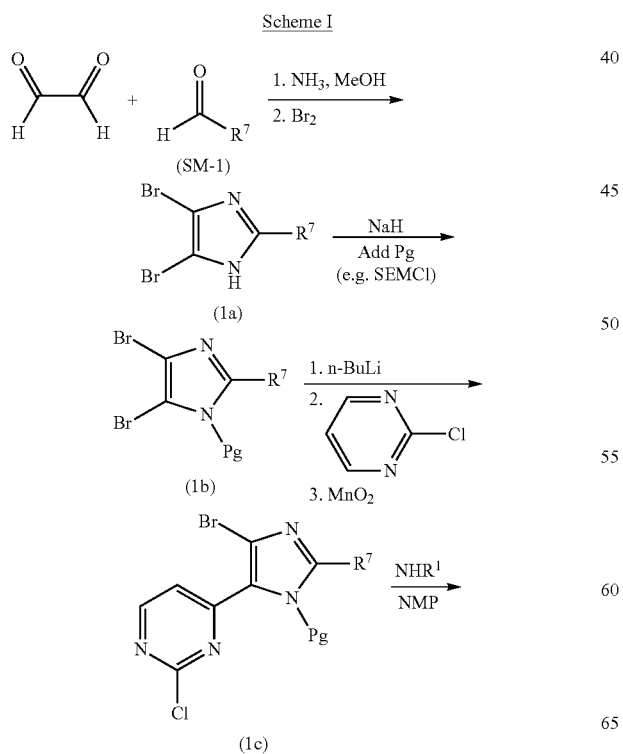

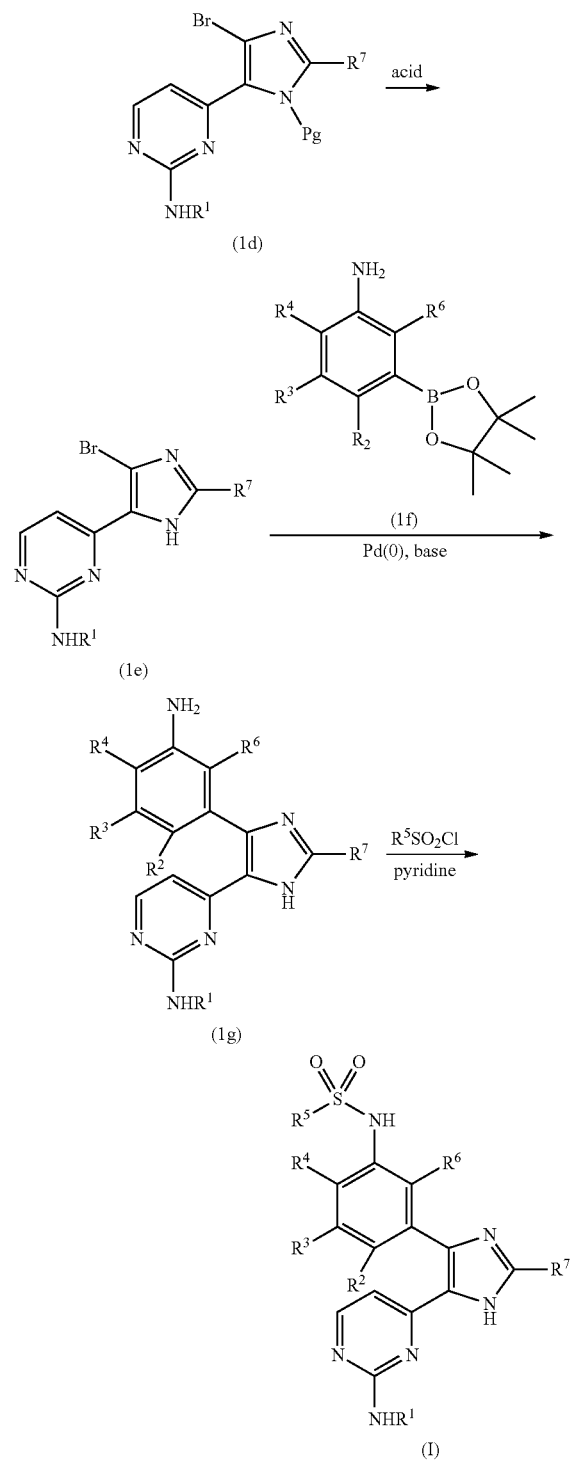

The dibromo imidazole intermediate (1a) may by prepared by condensing the desired aldehyde ($R^7C(O)H$) with glyoxal in the presence of ammonium hydroxide at a temperature from about 0° C. to about 5° C. to afford the C-2 substituted imidazole (see e.g., *J Med Chem*, (1979), 22, 687), followed by bromination. Deprotonation with NaH, and addition of an amino-protection group (e.g., 2-(trimethylsilyl)ethoxymethyl chloride (SEMCl) would furnish the protected dibromo imidazole (1b). Those skilled in the art will appreciate that other nitrogen protecting groups may be employed instead of the SEM protecting group. Directed lithiation, followed by addition into 2-chloropyrimidine and subsequent oxidation can provide the 5-(2-chloro-4-pyrimidinyl)-4-bromoimidazole (1c). See, *Organic Letters* 2005, 7, 4133. Simple SnAr substitution with the desired amine ($R^1NH$) can afford substituted pyrimidines (1d). SEM deprotection (e.g., HCl in protic solvent, such as ethanol, etc.) to afford intermediate (1e) and subsequent Suzuki cross-coupling with the desired sulfonanilide boronate ester or acid (1f) would provide intermediate (1g). The final cross-coupling may be generally substituted with the corresponding Stille reactions where the boronate ester or acid is replaced with the corresponding stannane. The desired sulfonyl chloride may then be added to the primary amine group of intermediate (1g) in the presence of a base (e.g., pyridine) to produce a compound of Formula (I).

Compounds of Formula I or II can also be prepared by the procedures outlined below in Scheme II.

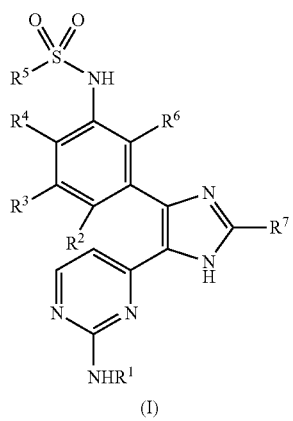

(I)

Reversing the order of cross-coupling and deprotection from Scheme I would yield the trisubstituted imidazole (1g). Removal of the imidazole protecting could also be reserved to the end of the synthetic sequence. Treatment with the desired sulfonyl chloride ($R^5SO_2Cl$) in the presence of pyridine at reduced temperatures produces a compound of Formula (I).

Another alternative route for making compounds of the present invention is outlined in Scheme III below.

Scheme II

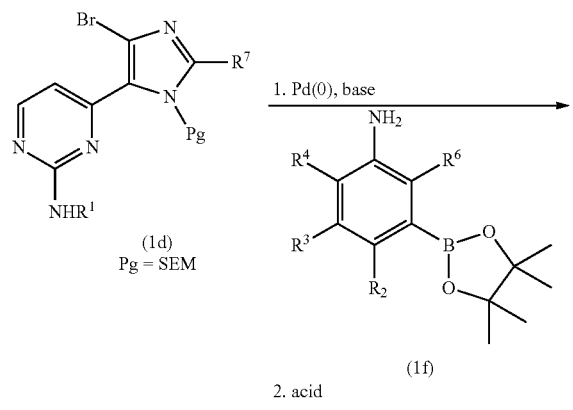

Scheme III

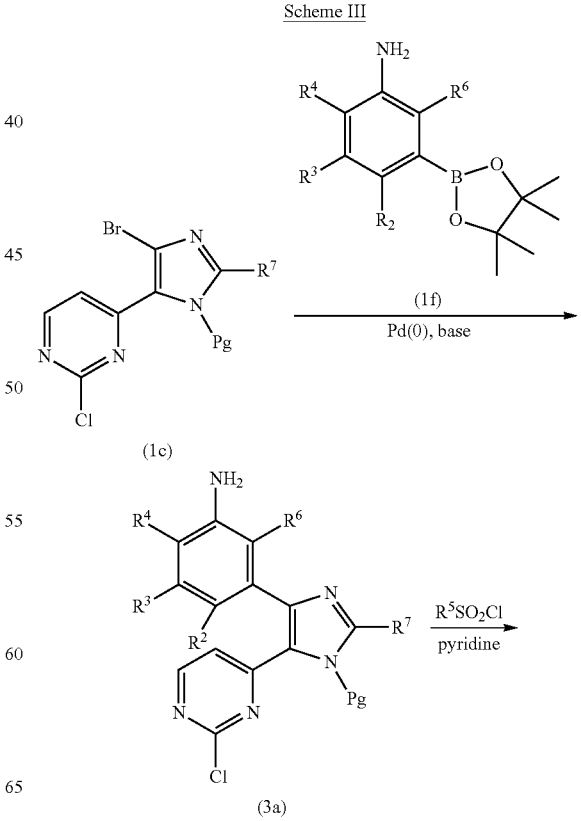

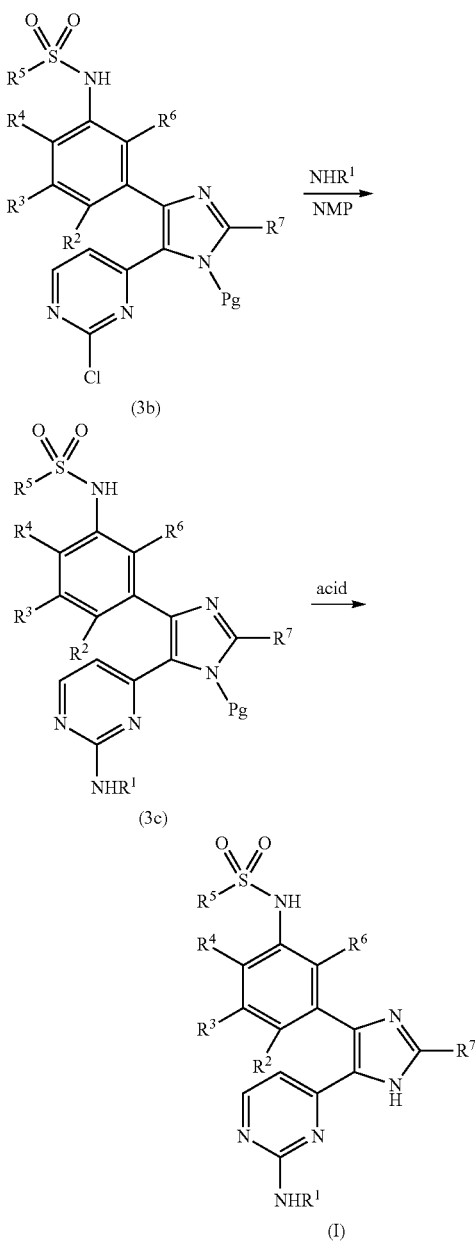

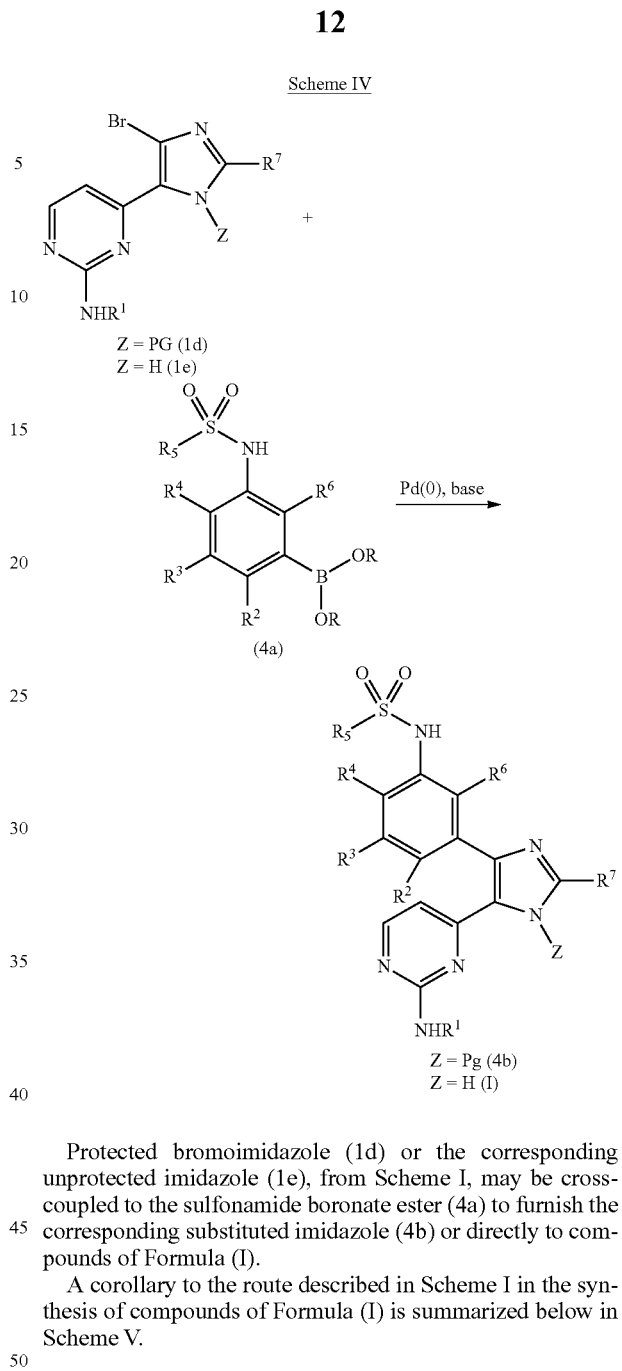

In a variation of the route described in Scheme I, the bromoimidazole intermediate (1c) may be cross-coupled with the appropriate boronate ester or (1f) to provide the 3-(5-(2-chloropyrimidin-4-yl)-1H-imidazol-4-yl)aniline (3a). Treatment with the desired sulfonyl chloride will furnish the corresponding sulfonanilide (3b). Simple SnAr substitution with the desired amine (R¹NH) can afford substituted pyrimidines (3c) and deprotection of the imidazole would yield compounds of Formula (I).

Another variation of Scheme I is depicted in Scheme IV below.

Protected bromoimidazole (1d) or the corresponding unprotected imidazole (1e), from Scheme I, may be cross-coupled to the sulfonamide boronate ester (4a) to furnish the corresponding substituted imidazole (4b) or directly to compounds of Formula (I).

A corollary to the route described in Scheme I in the synthesis of compounds of Formula (I) is summarized below in Scheme V.

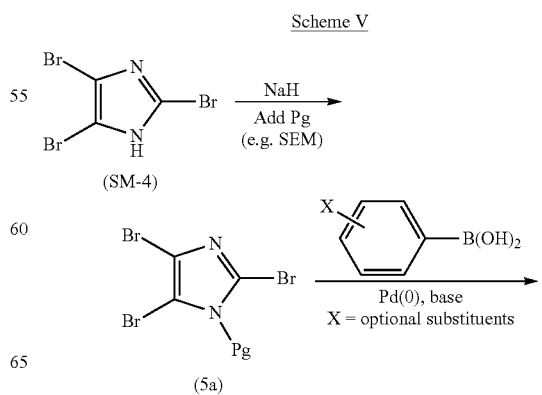

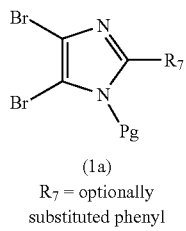

(1a)
R₇ = optionally substituted phenyl

Tribromoimidazole may be protected as described in Scheme I to produce intermediate (5a). Selective C-2 Suzuki cross-coupling with an optionally substituted phenyl boronic acid or ester could provide the common intermediate (1a) which could then be elaborated to compounds of Formula (I) as outlined in Scheme I. See *Tetrahedron Letters*, 1998, 39, 5171.

Those of skill in the art will appreciate that compounds of the present invention could be made using procedures analogous to those described in the Example section below.

The compounds of the present invention (including intermediates) may be isolated and used per se or in the form of its pharmaceutically acceptable salt, solvate and/or hydrate. Many of the intermediates and compounds represented by Formula I are capable of forming acid addition salts, particularly pharmaceutically acceptable acid addition salts. Pharmaceutically acceptable acid addition salts of the compound of the present invention include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of Formula I or II by known salt-forming procedures.

Compounds of the present invention which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of Formula I by known salt-forming procedures.

For those compounds containing an asymmetric carbon atom, the compounds exist in individual optically active isomeric forms or as mixtures thereof, e.g. as racemic or diastereomeric mixtures. Unless specified otherwise, the present invention embraces both individual optically active R and S isomers as well as mixtures, e.g. racemic or diastereomeric mixtures, thereof. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a commercially available chiral High pressure liquid chromatography (HPLC) column.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of Formula I or II (or pharmaceutically acceptable salt thereof) in combination with an excipient, wherein the excipient is a solvent. The compound per se, pharmaceutical salt thereof, or a solvate/hydrate of the compound or salt may exist in either amorphous or crystalline form (e.g., polymorphs).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention includes all pharmaceutically acceptable isotopically-labeled compounds of Formula (I) or (II) wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the invention are useful in vitro and/or in vivo in inhibiting the growth of cancer cells. Consequently, the compounds of the present invention (including the compositions and processes used therein) may be used in the manufacture of a medicament for the therapeutic applications described herein. The compounds may be used alone or in compositions together with a pharmaceutically acceptable carrier, solvents (including water), or excipient. Suitable pharmaceutically acceptable carriers, diluents, or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference. The pharmaceutical compositions include the incorporation of solvents (including water) into a crystalline matrix of the compound (also referred to as solvates and hydrates).

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, B-Raf.

The Ras-Raf-MEK-ERK signaling pathway transmits signals from cell surface receptors to nucleus and is essential for cell proliferation and survival. Since 10-20% of human cancers harbor oncogenic Ras mutation and many human cancers have activated growth factor receptors, this pathway is an ideal target for intervention.

The Raf family of serine/threonine kinase include three members: C-Raf (or Raf-1), B-Raf and A-Raf. Both the essential role and the position of Raf in many signaling pathways have been demonstrated from studies using deregulated and dominant inhibitory Raf mutants in mammalian cells as well as from studies employing biochemical and genetic techniques to model organisms. In the past, the focus on Raf being an anti-tumor drug target centered on its function as a downstream effector of Ras. However, recent findings suggest that Raf may have a prominent role in the formation of certain tumors with no requirement of an oncogenic Ras allele. In particular, activating alleles of B-Raf have been identified in ~70% of melanomas, 40% of papillary thyroid carcinoma, 30% of ovarian low-grade carcinoma, and 10% of colorectal cancers. Most B-Raf mutations are found within the kinase domain, with a single substitution (V599E) accounting for 80%. The mutated B-Raf proteins activate Raf-MEK-ERK pathway either via elevated kinase activity toward MEK or via activating C-Raf.

Therefore, development of a kinase inhibitor for B-Raf provides a new therapeutic opportunity for treatment of many types of human cancers, especially for metastatic melanomas, solid tumors, brain tumors such as Glioblastoma multiform (GBM), acute myelogenous leukemia (AML), papillary thyroid carcinoma, ovarian low-grade carcinoma, and colorectal cancer. Several Raf kinase inhibitors have been described as exhibiting efficacy in inhibiting tumor cell proliferation in vitro and/or in vivo assays (see, for example, U.S. Pat. Nos. 6,391,636; 6,358,932; 6,037,136; 5,717,100; 6,458,813; 6,204,467; and 6,268,391). Other patents and patent applications suggest the use of Raf kinase inhibitors for treating leukemia (see, for example, U.S. Pat. Nos. 6,268,391; 6,204,467; 6,756,410; and 6,281,193; and abandoned U.S. Patent Application Nos. 20020137774 and 20010006975), or for treating breast cancer (see, for example, U.S. Pat. Nos. 6,358,932; 5,717,100; 6,458,813; 6,268,391; 6,204,467; and 6,911,446).

The compounds of the present invention inhibit cellular processes involving B-Raf kinase by blocking the signal cascade in these cancer cells and ultimately inducing stasis and/or death of the cells.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

The pharmaceutical formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Oral formulations can also comprise the active ingredient along with 20-60% Eudragit EPO, Hydroxypropyl cellulose EF, Hydroxypropyl methylcellulose, or Kollidon VA64, and up to 5% of pluronic F68, Cremophor EL, or Gelucire 44/14. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

In some therapies, it may be advantageous to administer the compounds of the invention in combination with one or more therapeutic agents (pharmaceutical combinations). For example, synergistic effects can occur with other anti-tumor or anti-proliferative agents, for example, mitotic inhibitors, alkylating agents, anti-metabolites, intercalating antibiotics, growth factor inhibitors (e.g., trastuzumab, panitumumab, cetuximab, gefitinib, erlotinib, lapatinib, sorafenib, etc.), cell cycle inhibitors, enzymes, topoisomerase inhibitors, biological response modifiers, antibodies, cytotoxics, anti-hormones, anti-androgens, an anti-angiogenesis agent, kinase inhibitor, pan kinase inhibitor or growth factor inhibitor. Suitable therapeutic agents include erlotinib, docetaxel, gemcitabine, cisplatin, carboplatin, paclitaxel, bevacizumab, trastuzumab, pertuzumab, temozolomide, taxoxifen, doxorubicin, rapamycin and lapatnib. Other suitable therapeutic agents are listed in the Physicians Desk Reference.

Preferred therapeutic agents for combination therapy include MEK inhibitors (e.g., sorafenib, AZD6244 (Example 10 of WO 03/077914), 2-(2-fluoro-4-iodophenylamino)-N-(2-hydroxyethoxy)-1,5-dimethyl-6-oxo-1,6-dihydropyridine-3-carboxamide, 4-(4-bromo-2-fluorophenylamino)-N-(2-hydroxyethoxy)-1,5-dimethyl-6-oxo-1,6-dihydropyridazine-3-carboxamide, PD-0325901 (N-[(2-R)-2,3-dihydroxypropoxy]-3,4-difluoro-2-[(2-fluoro-4-iodophenyl)amino]-benzamide available from Axon Medchem), PD-184352 (2-(2-chloro-4-iodophenyl)amino-N-(cyclopropylmethoxy)-3,4-difluorobenzamide available from Axon Medchem), PD-0325901 (N—[((R)-2,3-dihydroxypropyl)oxy]-3,4-difluoro-2-[(2-fluoro-4-iodophenyl)amino]benzamide available from Axon Medchem), SL-327 (α-[amino[(4-aminophenyl)thio]methylene]-2-(trifluoromethyl)benzeneacetonitrile available from Axon Medchem), XL-518 (Exelixis), AR-119 (Ardea Biosciences, Valeant Pharmaceuticls), AS-701173 (Merck Serono), AS-701255 (Merck Serono), 360770-54-3 (Wyeth), RDEA119 ((S)—N-(3,4-difluoro-2-(2-fluoro-4-iodophenylamino)-6-methoxyphenyl)-1-(2,3-dihydroxypropyl)cyclopropane-1-sulfonamide)):

mTOR inhibitors (e.g., Rapamycin (sirolimus), TORISEL™ (temsirolimus), RAD001 (everolimus), AP23573 (deforolimus), OSI-027 (OSI Pharmaceuticals), compounds described in WO 06/090167; WO 06/090169; WO 07/080382, WO 07/060404; and WO08/023161): and PI3K inhibitors (e.g., wortmannin, 17-hydroxywortmannin analogs described in WO 06/044453, 4-(2-(1H-indazol-4-yl)-6-((4-(methylsulfonyl)piperazin-1-yl)methyl)thieno-[3,2-d]pyrimidin-4-yl)morpholine, (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, 4-(2-(1H-indazol-4-yl)-6-((4-(methylsulfonyl)piperazin-1-yl)methyl)thieno-[2,3-d]pyrimidin-4-yl) morpholine, LY294002 (2-(4-Morpholinyl)-8-phenyl-4H-1-benzopyran-4-one available from Axon Medchem), PI 103 hydrochloride (3-[4-(4-Morpholinylpyrido[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzene-sulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (-(1H-Indazol-4-yl)-6-(4-methanesulfonyl-piperazin-1ylmethyl)-4-morpholin-4-yl-thieno[3,2-d]pyrimidine bismesylate available from Axon Medchem), BEZ235 (2-Methyl-2-[4-(3-methyl-2-oxo-8-quinolin-3-yl-2,3-dihydro-imidazo[4,5-c]quinolin-1-yl)-phenyl]-propionitrile available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147.

Where the compounds of the invention are administered in conjunction with other therapies, dosages of the co-administered compounds will of course vary depending on the type of co-drug employed, on the specific drug employed, on the condition being treated and so forth.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent (described above) may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The invention also provides for a pharmaceutical combinations, e.g. a kit, comprising a) a first agent which is a compound of the invention as disclosed herein, in free form or in pharmaceutically acceptable salt form, and b) at least one additional therapeutic agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

EXAMPLES

The present invention is further exemplified, but not limited, by the following intermediates and examples that illustrate the preparation of compounds of the present invention.

Preparative separations are carried out using a Combi-Flash® Rf system (Teledyne Isco Inc. Lincoln, Nebr.) in combination with RediSep® Normal-Phase Silica Flash Columns (4 g-120 g, 35-70 micron particle size; Teledyne Isco Inc.), or by flash column chromatography using silica gel (230-400 mesh) packing material, or by HPLC using a WATERS 2767 Sample Manager, C-18 reversed phase column, 30×50 mm, flow 75 mL/min. Typical solvents employed for the CombiFlash® system and flash column chromatography are dichloromethane, methanol, ethyl acetate, hexane, acetone, aqueous ammonia (or ammonium hydroxide), and triethyl amine Typical solvents employed for the reverse phase HPLC are varying concentrations of acetonitrile and water with 0.1% trifluoroacetic acid (TFA).

Microwave reactions conducted in a Creator or Initiator microwave system (Biotage, Charlottesville, Va.)

The following acronyms having the corresponding meanings are used in the experimental section below.

| | |
|---|---|
| DEAD—diethyl azodicarboxylate | DIEA—diisopropylethyl amine |
| THF—tetrahydrofuran | Et$_2$O—diethyl ether |
| DMF—dimethylformamide | NMP—N-methylpyrrolidinone |
| DME—1,1-dimethoxyethane | DPPA—diphenyl phosphorazide |
| EtOAc—ethyl acetate | TFA—trifluoroacetic acid |
| NBS—N-bromosuccinimide | dba—dibenzylideneacetone |
| dppf—bis(diphenylphosphino)ferrocene | PPTS—pyridinium p-toluenesulfonate |

Preparation of Key Starting Materials and Intermediates

Preparation of starting material (S)-tert-butyl 1-aminopropan-2-ylcarbamate (SM-1)

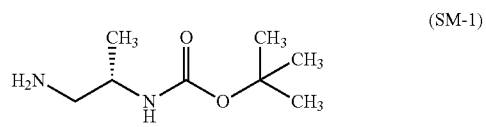

(SM-1)

Step 1. Preparation of (S)-tert-butyl 1-(1,3-dioxisoindolin-2-yl)propan-2-ylcarbamate To a stirred solution of (S)-tert-butyl 1-hydroxypropan-2-ylcarbamate (7.4 g, 42.2 mmol) in dry THF (420 mL) were added phthalimide (6.83 g, 46.4 mmol) and PPh$_3$ (12.18 g, 46.4 mmol) DEAD (7.3 mL, 46.4 mmol) was then added dropwise to the stirred solution at room temperature, and maintained for 3 hours. The reaction mixture was then concentrated and the resulting residue was purified by flash chromatography (SiO$_2$, 30-70% EtOAc in hexanes) to provide 12.5 g of (S)-tert-butyl 1-(1,3-dioxisoindolin-2-yl)propan-2-ylcarbamate. LCMS (m/z) 205.1 (MH$^+$-BOC), $t_R$=0.86 minute; $^1$H NMR (CDCl$_3$, 400 MHz) δ 7.82-7.87 (m, 2H), 7.67-7.75 (m, 2H), 4.60-4.76 (br d, 1H), 4.03-4.20 (br s, 1H), 3.62-3.72 (m, 2H), 1.25 (s, 9H), 1.21 (d, J=6.6 Hz, 3H).

Step 2. Preparation of (S)-tert-butyl 1-aminopropan-2-ylcarbamate (SM-1)

Hydrazine monohydrate (20 mL, 642.7 mmol) was added to a suspension of (S)-tert-butyl 1-(1,3-dioxisoindolin-2-yl)propan-2-ylcarbamate (12.5 g, 41.1 mmol) in dry methanol (150 mL), and the resulting mixture was heated to 50° C. for 1 hour. After cooling to room temperature, the reaction mixture was filtered through a sintered funnel, and the filtrate concentrated. The resulting residue was suspended in diethyl ether (300 mL) and filtered, washing the filter cake thoroughly with diethyl ether. The combine filtrates were filtered and concentrated to furnish 6.3 g of (S)-tert-butyl-1-aminopropan-2-ylcarbamate: $^1$H NMR (CDCl$_3$, 400 MHz) δ 4.44-4.71 (br s, 1H), 3.53-3.74 (br m, 1H), 2.75 (dd, J=4.9, 12.9 Hz, 1H), 2.64 (dd, J=6.6, 12.9 Hz, 1H), 1.45 (s, 9H), 1.15-1.34 (br s, 2H), 1.12 (d, J=6.7 Hz, 3H).

Preparation of starting material (S)-tert-butyl 1-aminopropan-2-ylcarbamate (SM-2)

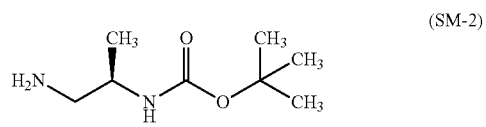

(SM-2)

(R)-tert-butyl 1-aminopropan-2-ylcarbamate was prepared in a similar fashion as above using (R)-tert-butyl 1-hydroxypropan-2-ylcarbamate as the starting material.

Preparation of starting material
3-amino-2-methylpropanenitrile (SM-3)

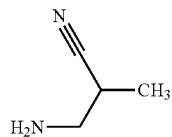

(SM-3)

Following the procedure described in U.S. Pat. No. 2,659,739, a 200 mL steel bomb was charged with 32% aqueous ammonia solution (81 mL) and of methacrylonitrile (18 g, 23 mL, 270 mmol). The reaction vessel was sealed and heated to 135° C. with stirring for 2 hours. The reaction was allowed to cool to room temperature and the reaction mixture was distilled under reduced pressure (84-85° C., 24 mbar) to furnish 12.4 g (147 mmol, 53%) 3-amino-2-methylpropanenitrile as a colorless oil: $^1$H NMR (CDCl$_3$, 400 MHz) δ 2.89 (dd, J=4.9, 6.5 Hz, 2H), 2.63-2.72 (m, 1H), 1.37 (2H), 1.32 (m, 2H), 1.31 (d, J=7.4 Hz, 3H).

Preparation of starting material
3-amino-2-methylpropanenitrile (SM-4)

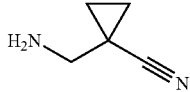

(SM-4)

Step 1. Preparation of
1-(hydroxymethyl)cyclopropanecarbonitrile

Following a procedure reported in WO 2009/024550, a solution of ethyl 1-cyanocyclopropanecarboxylate (4.0 g, 28.7 mmol) in a DME (80 mL) and methanol (8 mL) was treated with NaBH$_4$ (8.7 g, 230 mmol) and stirred at room temperature for 24 hours. The reaction was then quenched with saturated aqueous NaHCO$_3$ solution (100 ml) with gas evolution under control, and then extracted with 9:1 DCM-MeOH (3×50 ml). The organic layers were combined, dried (Na$_2$SO$_4$), concentrated to give 1-(hydroxy-methyl)-cyclopropanecarbonitrile (2.34 g, 24.1 mmol, 84%) as a colorless oil which was used without further purification: $^1$H NMR (300 MHz, CDCl$_3$) δ 3.63 (s, 2H), 2.10-2.45 (br s, 1H), 1.20-1.35 (m, 2H), 0.90-1.05 (m, 2H).

Step 2. Preparation of 1-((1,3-dioxoisoindolin-2 yl)methyl)cyclopropanecarbonitrile A solution of 1-(hydroxymethyl)-cyclopropanecarbonitrile (5.52 g, 56.8 mmol), phthalimide (9.20 g, 62.5 mmol), and triphenylphosphine (16.4 g, 62.5 mmol) in THF (550 mL) was treated with DEAD (9.90 mL, 62.5 mmol) and stirred at room temperature for 17 hours. The reaction mixture was then concentrated and the resulting solids were triturated in diethyl ether (150 mL), and collected by filtration. Purification by flash chromatography (SiO$_2$, 0-20% EtOAc in DCM) afforded 1-((1,3-dioxoisoindolin-2-yl)methyl)-cyclopropanecarbonitrile (8.8 g, 38.8 mmol, 68%) as a white solid: LCMS (m/z) 227.0 (MH$^+$), $t_R$=0.66 minute; $^1$H NMR (300 MHz, CDCl$_3$) δ 7.90 (dd, J=5.4, 3.1 Hz, 2H), 7.77 (dd, J=5.4, 3.1 Hz, 2H), 3.81 (s, 2H), 1.30-1.44 (m, 2H), 1.28 (d, J=3.8 Hz, 2H).

Step 3. Preparation of
1-(aminomethyl)cyclopropanecarbonitrile (SM-4)

A solution of 1-((1,3-dioxoisoindolin-2-yl)methyl)cyclopropanecarbonitrile (8.78 g, 38.8 mmol), hydrazine monohydrate (9.5 ml, 190 mmol) in MeOH (150 mL) was heated at 60° C. for 3 h with precipitation occurring 30 min after heating. The reaction mixture was then cooled down to room temperature and filtered. The filtrate was concentrated in vacuo and the resulting residue was sonicated with Et$_2$O (150 mL). The resulting suspension was filtered through a sintered funnel, and the filtrate was concentrated and dried in vacuo to provide 1-(aminomethyl)-cyclopropanecarbonitrile (3.6 g, 36.3 mmol, 93%) as a colorless oil: $^1$H NMR (300 MHz, CDCl$_3$) δ 2.76 (s, 2H), 1.60-2.25 (br s, 2H), 1.16-1.35 (m, 2H), 0.79-0.98 (m, 2H).

Preparation of starting material 5-chloro-2-fluoro-3-(4,4,5,5-tetramethyl-1,3,2-dioxaborolan-2-yl)aniline (SM-5)

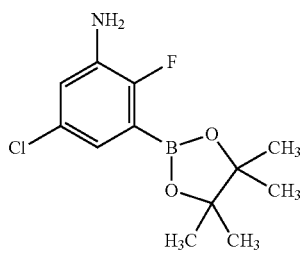

(SM-5)

Step 1: Preparation of
3-bromo-5-chloro-2-fluorobenzoic acid

To a cooled solution of diisopropylamine (2.4 mL, 17.2 mmol) in dry THF (15 mL) under Argon at 0° C. was added n-butyllithium (7.5 mL, 2.0 M in pentane, 15.0 mmol). After 30 minutes the solution was cooled to −78° C. and a solution of 2-bromo-4-chloro-1-fluorobenzene (3 g, 14.3 mmol) in dry THF (15 mL) was added over 15 minutes. After 1 hour, this solution was transferred via cannula over 10 minutes to a mixture of solid carbon dioxide and THF (30 mL) at −78° C. After 45 minutes the cold bath was removed and excess carbon dioxide was allowed to vent while the solution warmed to room temperature. The reaction mixture was then quenched with aqueous 0.5 M HCl solution (60 mL). After concentrating, the remaining aqueous phase was basified with aqueous 0.5 M NaOH solution and was washed with ethyl acetate (100 mL). The aqueous phase was then acidified with aqueous 1.0 M HCl solution and extracted with chloroform (2×75 mL). The combined organic portions were washed with brine, dried (Na$_2$SO$_4$) and concentrated to give 3.34 g of a semi-crystalline solid as a mixture of regioisomers with the desired isomer as the major: LCMS (m/z) not observed (MH⁺), $t_R$=0.66 minute; ¹H NMR (400 MHz, CDCl₃) δ 7.80 (dd, J=5.5, 2.7 Hz, 1H), 7.95 (dd, J=5.5, 2.7 Hz, 1H).

Step 2: Preparation of tert-butyl 3-bromo-5-chloro-2-fluorophenyl-carbamate

A mixture of 3-bromo-5-chloro-2-fluorobenzoic acid (3.34 g, 13.2 mmol), DIEA (2.04 g, 15.8 mmol) and diphenyl phosphorazide (DPPA, 4.53 g, 16.5 mmol) in 1:1 dry t-butanol and toluene (35 mL) was heated to and maintained at reflux for 23 hours. The reaction was allowed to cool to room temperature and was then partitioned between CHCl₃ (75 mL) and water (75 mL). The organic layer was separated, washed with brine, dried (Na₂SO₄), and then concentrated under reduced pressure to yield an oily residue. Purification by flash chromatography (SiO₂, 0-5% EtOAc in heptane) to yield tert-butyl 3-bromo-5-chloro-2-fluorophenylcarbamate (2.45 g, 7.5 mmol, 57%): LCMS (m/z) not ionized (MH⁺), $t_R$=1.20 minutes; ¹H NMR (400 MHz, CDCl₃) δ 8.17 (d, J=5.1 Hz, 1H), 7.16 (m, 1H), 6.72 (br s, 1H), 1.53 (s, 9H).

Step 3. Preparation of 3-bromo-5-chloro-2-fluoroaniline tert-Butyl 3-bromo-5-chloro-2-fluorophenylcarbamate (1.0 g, 3.1 mmol) was treated with 4.0 M HCl in dioxane (10 mL) and the resulting reaction was maintained at room temperature for 4 hours. The reaction mixture was concentrated and partitioned between EtOAc (200 mL) and saturated aqueous NaHCO₃ solution (75 mL). The layers were separated and the organic portion was washed with brine (75 mL), dried (Na₂SO₄), and concentrated to give 3-bromo-5-chloro-2-fluoroaniline as a colorless oil which was carried forward without further purification: LCMS (m/z) 225.9 (MH⁺), $t_R$=0.96 minute; ¹H NMR (400 MHz, CDCl₃) δ 6.88 (m, 1H), 6.70 (d, J=7.0 Hz, 1H).

Step 4. Preparation of 5-chloro-2-fluoro-3-(4,4,5,5-tetramethyl-1,3,2-dioxaborolan-2-yl)aniline (SM-5)

A mixture of 3-bromo-5-chloro-2-fluoroaniline (0.69 g, 3.1 mmol), bis(pinacolato)diboron (0.94 g, 3.7 mmol), and potassium acetate (0.91 g, 9.2 mmol) in dry dioxane (11 mL) was sparged with N₂. Dichloro 1,1'-bis(diphenylphosphino) ferrocene palladium (0.23 g, 0.31 mmol) was then added and the reaction vial sealed. The mixture was heated with an oil bath at 105° C. for 3.5 hours. The reaction mixture was then allowed to cool to room temperature, centrifuged, and the supernatant, which contained the desired compound 5-chloro-2-fluoro-3-(4,4,5,5-tetramethyl-1,3,2-dioxaborolan-2-yl)aniline, was decanted and used without further purification: LCMS (m/z) 189.9 (MH⁺, boronic acid), $t_R$=0.43 minute.

Preparation of N-(5-chloro-2-fluoro-3-(4,4,5,5-tetramethyl-1,3,2-dioxaborolan-2-yl)phenyl)propane-1-sulfonamide (SM-6)

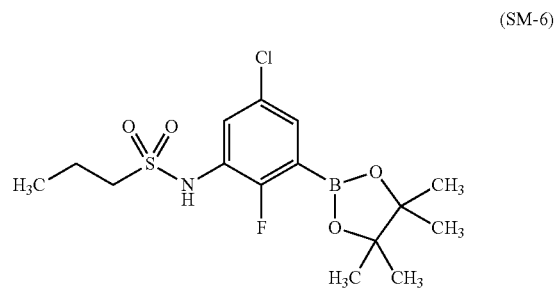 [SMILES: CCCS(=O)(=O)Nc1cc(Cl)cc(B2OC(C)(C)C(C)(C)O2)c1F]

(SM-6)

Step 1. Preparation of N-(3-bromo-5-chloro-2-fluorophenyl)propane-1-sulfonamide

To a solution of 3-bromo-5-chloro-2-fluoroaniline (SM-5, step 3, 0.52 g, 2.3 mmol) in pyridine (2.5 mL) cooled in an ice water bath was added propane-1-sulfonyl chloride (0.3 mL, 2.8 mmol). After 4 hours the solution was concentrated and partitioned between EtOAc (75 mL) and aqueous 0.1 M HCl solution (30 mL). The layers were separated and the organic phase was then washed with brine, dried (Na₂SO₄) and concentrated to give 778 mg of N-(3-bromo-5-chloro-2-fluorophenyl)propane-1-sulfonamide as a yellow solid which was carried forward without further purification: LCMS (m/z) not observed, $t_R$=0.95 minute.

Step 2. Preparation of N-(5-chloro-2-fluoro-3-(4,4,5,5-tetramethyl-1,3,2-dioxaborolan-2-yl)phenyl)propane-1-sulfonamide (SM-6)

This material was prepared following the procedure used for SM-5, step 4: LCMS (m/z) 590.3 (2×MH⁺), $t_R$=0.67 minute.

Preparation of starting 2,5-difluoro-3-(4,4,5,5-tetramethyl-1,3,2-dioxaborolan-2-yl)aniline (SM-7)

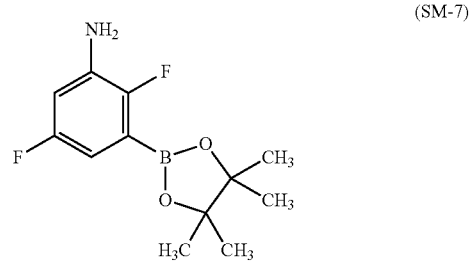 [SMILES: CC1(C)OB(c2cc(F)cc(N)c2F)OC1(C)C]

(SM-7)

Step 1. Preparation of 3-bromo-2,5-difluoroaniline

A mixture of 1,3-dibromo-2,5-difluorobenzene (4 g, 14.7 mmol), benzophenone imine (2.6 mL, 15.5 mmol), sodium tert-butoxide (2.1 g, 22.1 mmol), (S)-BINAP (1.4 g, 2.2 mmol), in toluene (15 mL) was sparged with Argon and charged with Pd₂(dba)₃ (0.67 g, 0.74 mmol). The reaction was then sealed and irradiated at 100° C. for 30 minutes in a microwave reactor. The reaction mixture was diluted with Et$_2$O and stirred for 2 hours with a palladium scavenger (Siliabond DMT). The mixture was filtered through a plug of Celite and the collected filtrate was partitioned between diethyl ether and water, and the resulting layers separated. The organic portion was washed with water, brine, dried (MgSO$_4$), and concentrated to afford a brown red solid. The solid was dissolved in THF (40 mL) and treated with aqueous 6.0 N HCl solution (25 ml, 150 mmol). The reaction was stirred for 1.5 hours at room temperature was partitioned between water and Et$_2$O. The layers were separated and the aqueous portion was brought to a pH of 9 with aqueous 1.0 M NaOH solution. The basic aqueous layer was extracted diethyl ether (3×30 mL) the combined diethyl ether layers were washed with aqueous 1.0 M NaOH solution, water, brine, dried (MgSO$_4$), concentrated. Purification by flash chromatography (SiO$_2$, 0-10% EtOAc in heptane) afforded 3-bromo-2,5-difluoroaniline (1.7 g, 8.2 mmol, 56%, trace benzophenone) as an orange solid: $^1$H NMR (400 MHz, CDCl$_3$) δ 3.93 (br s, 2H) 6.43 (m, 1H) 6.62 (m, 1H).

Step 2. Preparation of 2,5-difluoro-3-(4,4,5,5-tetramethyl-1,3,2-dioxaborolan-2-yl)aniline To a solution of 3-bromo-2,5-difluoroaniline (2.0 g, 9.4 mmol), bis(pinacolato)diboron (2.86 g, 11.25 mmol), tricyclohexylphosphine (0.184 g, 0.656 mmol), and potassium acetate (1.380 g, 14.06 mmol) in 1,4 dioxane (1.0 ml), was added Pd$_2$(dba)$_3$ (0.26 g, 0.28 mmol) and the resulting reaction mixture was irradiated to 120° C. in the microwave for 30 minutes. The reaction was allowed to cool to room temperature and was diluted with EtOAc and the reaction was diluted with EtOAc and palladium scavenger (Silicycle DMT) was added and mixture was stirred for 30 minutes, then filtered through a sintered funnel. The filtrate was washed with water, brine, dried (MgSO4), and concentrated to afford filtered and stripped to 2,5-difluoro-3-(4,4,5,5-tetramethyl-1,3,2-dioxaborolan-2-yl)aniline (2.4 g, 9.4 mmol): LCMS (m/z) 255.1 (MH$^+$), t$_R$=0.95 minute; LCMS (m/z) 174.0 (MH$^+$, boronic acid), t$_R$=0.3 minute.

Preparation of starting material 2-chloro-5-fluoro-3-(4,4,5,5-tetramethyl-1,3,2-dioxaborolan-2-yl)aniline (SM-8)

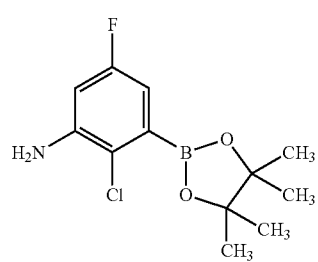

(SM-8)

Step 1. Preparation of 3-bromo-2-chloro-5-fluoroaniline

To a sealable glass tube was charged 1,3-dibromo-2-chloro-5-fluorobenzene (12.52 g, 43.4 mmol), benzophenone imine (8.26 g, 45.6 mmol), sodium tert-butoxide (6.26 g, 65.1 mmol), and toluene (100 mL). The resulting mixture was thoroughly sparged with Argon, followed by the addition of Pd$_2$(dba)$_3$ (0.398 g, 0.434 mmol) and (S)-BINAP (0.81 g, 1.3 mmol), and follow by another Argon sparge. The reaction tube was sealed and heated to 85° C. in an oil bath and maintained overnight. The reaction was allowed to cool to room temperature and quenched with water (20 mL). The resulting layers were partitioned and separated. The organic phase was concentrated and assayed to be a mixture of mono- and bis-aminated products (~4:1 by HPLC area at 220 nm). The residue was dissolved in THF (70 mL), treated with aqueous 3.0 M HCl (20 mL) at room temperature for 1 hour and basified with saturated aqueous Na$_2$CO$_3$ solution (40 mL). The reaction mixture was allowed to partition and the layers were separated. The organic portion was separated, washed with brine, concentrated and the resulting residue was purified by flash chromatography (SiO$_2$, 0-15% EtOAc in heptane) and 3-bromo-2-chloro-5-fluoroaniline was obtained as a light yellow solid (6.82 g, 30.4 mmol): LCMS (m/z): not ionized (MH$^+$), t$_R$=0.95 minute; $^1$H NMR (CDCl$_3$, 300 MHz) δ 4.32 (br s, 2H), 6.44 (dd, J=9.8, 2.8 Hz, 1H), 6.77 (dd, J=7.9, 2.6 Hz, 1H).

Step 2. Preparation of 2-chloro-5-fluoro-3-(4,4,5,5-tetramethyl-1,3,2-dioxaborolan-2-yl)aniline (SM-8)

To a glass pressure vial was added 3-bromo-2-chloro-5-fluoroaniline (10.22 g, 45.5 mmol), bis(pinacolato)diboron (13.9 g, 54.6 mmol), tricyclohexylphosphine (0.89 g, 3.2 mmol), potassium acetate (6.70 g, 68.3 mmol), and Pd(dba)$_2$ (1.31 g, 2.3 mmol) in 1,4-dioxane (170 mL) to give a red suspension which was sparged with nitrogen, and the reaction vessel was then sealed. The reaction mixture was heated in an oil bath to 120° C. for 5 hours and was then allowed to cool to room temperature. SiliaBond DMT (10 g, from Silicycle) was added and mixture stirred 1 hour at room temperature. The mixture was diluted with EtOAc and filtered through neutral alumina with a cover of silica gel, washing the filter cake thoroughly with EtOAc. The combined filtrates were partitioned with water and the phases separated. The aqueous phase was extracted with EtOAc. The organic phases were combined, washed with water, brine, dried (Na$_2$SO$_4$), filtered and concentrated to a yellow oil. Heptane was added and mixture briefly sonicated to provide a suspension which upon concentration afforded 2-chloro-5-fluoro-3-(4,4,5,5-tetramethyl-1,3,2-dioxaborolan-2-yl)aniline (14.64 g, 35.0 mmol, 65% purity by $^1$H NMR) as an orange solid which was used without further purification. A purified sample (SiO$_2$, 0-50% EtOAc in heptane) was obtained for characterization: LCMS (m/z): 272.0 (MH$^+$), t$_R$=0.99 minute: $^1$H NMR (300 MHz, CDCl$_3$) δ 1.36 (s, 12H) 4.17 (br s, 2H) 6.53 (dd, J=9.8, 2.7 Hz, 1H) 6.76 (dd, J=8.6, 2.7 Hz, 1H).

Preparation of Starting material 2-chloro-3-(4,4,5,5-tetramethyl-1,3,2-dioxaborolan-2-yl)aniline (SM-9)

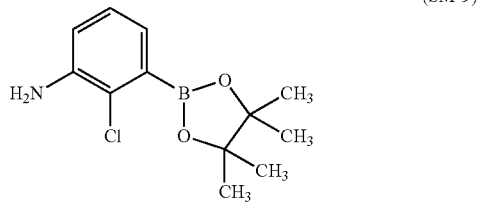

(SM-9)

Step 1. Preparation of 1-bromo-2-chloro-3-nitrobenzene

To an oven dried round-bottom flask fitted with stir bar and an oven dried condenser under $N_2$ at room temperature was added 2-chloro-3-nitrobenzoic acid (6.0 g, 29.8 mmol), mercuric oxide, red (9.67 g, 44.7 mmol) and carbon tetrachloride (200 mL). The reaction mixture heated to 90° C. for 30 minutes with irradiation from a 150 W TYPE A utility light bulb. The reaction mixture was then cooled to approximately 60° C. and bromine (2.30 mL, 44.7 mmol) added dropwise via syringe and the nitrogen inlet was replaced with an Ar balloon. The reaction mixture was heated again to 90° C. for 4 hours under constant irradiation from the light bulb. The reaction was allowed to cool to room temperature, quenched with saturated aqueous $NaHCO_3$ solution and DCM and stirred for 30 minutes. The phases partitioned upon standing and then were separated. The aqueous portion was extracted with DCM. The combined organic phases were washed with water, brine, dried ($Na_2SO_4$), filtered and concentrated in vacuo to afford 7.04 g of 1-bromo-2-chloro-3-nitrobenzene: $^1$H NMR (400 MHz, $CDCl_3$) δ 7.31 (t, J=8.0 Hz, 1H) 7.74 (dd, J=8.2, 1.2 Hz, 1H) 7.87 (dd, J=8.0, 1.4 Hz, 1H).

Step 2. Preparation of 3-bromo-2-chloroaniline

To a solution of 1-bromo-2-chloro-3-nitrobenzene (3.0 g, 12.7 mmol) in MeOH (127 ml) was added Zn dust (8.30 g, 127 mmol) followed by $NH_4Cl$ (6.79 g, 127 mmol) which resulted in a significant exotherm. The heterogeneous reaction mixture was stirred at room temperature for 1 hour. The reaction mixture was filtered through a pad of Celite and concentrated to an off-white solid. To this solid was added EtOAc and the resulting mixture was sonicated for 10 minutes. The mixture was filtered through Celite and washed with EtOAc. The combine filtrates were concentrated in vacuo to afford 2.17 g (10.5 mmol, 79%) of 3-bromo-2-chloroaniline: LCMS (m/z): 205.9 ($MH^+$); $t_R$=0.87 minute: $^1$H NMR (400 MHz, $CDCl_3$) δ 6.62-6.66 (m, 1H) 6.87 (t, J=8.0 Hz, 1H) 6.97 (d, J=7.8 Hz, 1H) 7.22 (d, J=9.0 Hz, 1H).

Step 3. Preparation 2-chloro-3-(4,4,5,5-tetramethyl-1,3,2-dioxaborolan-2-yl)aniline (SM-9)

To a glass pressure vessel was added 3-bromo-2-chloroaniline (3.08 g, 14.9 mmol), bis(pinacolato)diboron (4.55 g, 17.9 mmol), tricyclohexylphosphine (0.29 g, 1.04 mmol), potassium acetate (2.2 g, 22.4 mmol), and $Pd_2dba_3$ (0.41 g, 0.45 mmol) in 1,4-dioxane (75 mL) to give a red suspension which was sparged with nitrogen, and the reaction vessel was then sealed. The reaction was heated in an oil bath to 120° C. for 2 hours. LCMS of an aliquot indicted complete conversion and the reaction was allowed to cool to room temperature. SiliaBond DMT (4 g from SiliCycle) was added and the resulting mixture was stirred at room temperature for 30 minutes, then filtered through a plug of neutral alumina layered with $SiO_2$. The filter cake was washed thoroughly with EtOAc and the combined filtrates were partitioned water. The phases were separated and the aqueous portion was extracted with EtOAc. The combined organic portions were washed with water (2×), brine, dried ($Na_2SO_4$), and concentrated to provide 2-chloro-3-(4,4,5,5-tetramethyl-1,3,2-dioxaborolan-2-yl)aniline (1.6 g) as a dark yellow crystalline solid which was used without further purification: LCMS (m/z) 254.0 ($MH^+$); $t_R$=0.91 minute.

Preparation of starting material N-(2-chloro-3-(4,4,5,5-tetramethyl-1,3,2-dioxaborolan-2-yl)phenyl)propane-1-sulfonamide (SM-10)

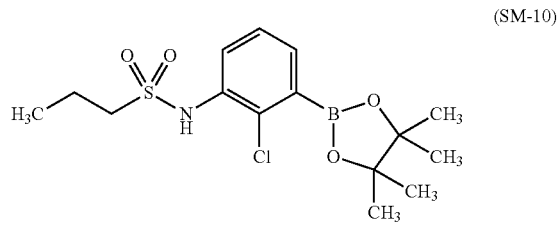 [SMILES: CCCS(=O)(=O)Nc1cccc(B2OC(C)(C)C(C)(C)O2)c1Cl]

(SM-10)

Step 1. Preparation of N-(3-bromo-2-chlorophenyl)propane-1-sulfonamide

This material was prepared from 3-bromo-2-chloro aniline (SM-9, step 2) following the procedure used for SM-6, step 1. Purification by flash chromatography ($SiO_2$; 0-60% EtOAc in heptane) afforded N-(3-bromo-2-chlorophenyl)propane-1-sulfonamide (51%): $^1$H NMR (400 MHz, $CDCl_3$) δ 1.05 (t, J=7.4 Hz, 3H) 1.83-1.95 (m, 2H) 3.01-3.15 (m, 2H) 4.21 (br s, 1H) 7.17 (t, J=8.22 Hz, 1H) 7.44 (d, J=8.2 Hz, 1H) 7.67 (d, J=8.22 Hz, 1H).

Step 2. Preparation of N-(2-chloro-3-(4,4,5,5-tetramethyl-1,3,2-dioxaborolan-2-yl)phenyl)propane-1-sulfonamide (SM-10)

This material was prepared using the product from the previous step and following the procedure used for SM-9, step 3 (88%): LCMS (m/z): 360.1 ($MH^+$); $t_R$=1.06 minutes.

Preparation of 2-fluoro-3-(4,4,5,5-tetramethyl-1,3,2-dioxaborolan-2-yl)aniline (SM-11)

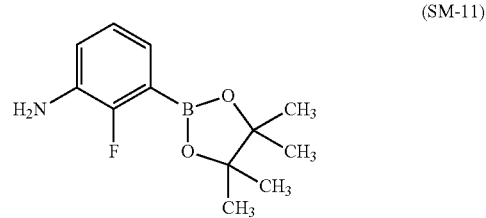 [SMILES: CC1(C)OB(c2cccc(N)c2F)OC1(C)C]

(SM-11)

Step 1. Preparation of 3-bromo-2-fluoroaniline

This material was prepared from 1-bromo-2-fluoro-3-nitrobenzene, following the procedure used for SM-9, step 2 (94%): LCMS (m/z) 189.9, $t_R$=0.74 minute; $^1$H NMR (300 MHz, CDCl$_3$) δ 3.81 (br s, 2H) 6.64-6.75 (m, 1H) 6.80 (t, J=8.2 Hz, 1H) 6.84-6.95 (m, 1H).

Step 2. Preparation of 2-fluoro-3-(4,4,5,5-tetramethyl-1,3,2-dioxaborolan-2-yl)aniline (SM-11)

This material was prepared following the procedure used for SM-9, step 3: LCMS (m/z): 115.9 (MH$^+$, boronic acid); $t_R$=0.17 minute.

Preparation of starting material N-(2-fluoro-3-(4,4,5,5-tetramethyl-1,3,2-dioxaborolan-2-yl)phenyl)propane-1-sulfonamide (SM-12)

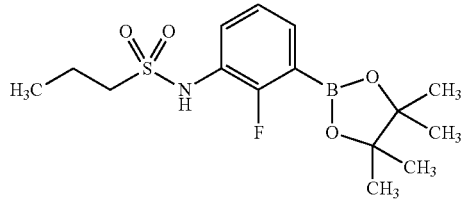

(SM-12)

Step 1: Preparation of N-(3-bromo-2-fluorophenyl)propane-1-sulfonamide

This material was prepared from 3-bromo-2-fluoroaniline (SM-11, step 1), following the procedure used for SM-6, step 1. Purification by flash chromatography (SiO$_2$, 0-50% EtOAc in heptane) afforded N-(3-bromo-2-fluorophenyl) propane-1-sulfonamide (56%) as a white crystalline solid: $^1$H NMR (400 MHz, CDCl$_3$) δ 1.05 (t, J=7.4 Hz, 3H) 1.80-1.97 (m, 2H) 2.99-3.20 (m, 2H) 6.60 (br s, 1H) 7.04 (t, J=7.6 Hz, 1H) 7.34 (app t, J=6.7 Hz, 1H) 7.56 (app t, J=7.6 Hz, 1H).

Step 2. Preparation of N-(2-fluoro-3-(4,4,5,5-tetramethyl-1,3,2-dioxaborolan-2-yl)phenyl)propane-1-sulfonamide (SM-12)

This material was prepared following the procedure used for SM-9, step 3, and was used in next steps without further characterization and purification.

Preparation of starting material 3,3,3-trifluoro-N-(2-fluoro-3-(4,4,5,5-tetramethyl-1,3,2-dioxaborolan-2-yl)phenyl)propane-1-sulfonamide (SM-13)

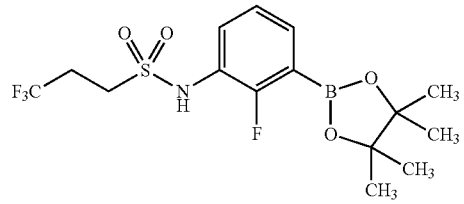

(SM-13)

Step 1. Preparation of N-(3-bromo-2-fluorophenyl)-3,3,3-trifluoropropane-1-sulfonamide This material was prepared from 3-bromo-2-fluoroaniline (SM-11, step 1), according to the procedure used for SM-6, step 1: LCMS (m/z) not ionized (MH$^+$), $t_R$=0.92 minute; $^1$H NMR (400 MHz, CDCl$_3$) δ ppm 2.62-2.82 (m, 2H) 3.30-3.43 (m, 2H) 7.05-7.13 (m, 1H) 7.43 (t, J=6.9 Hz, 1H) 7.50-7.56 (m, 1H).

Step 2. Preparation of 3,3,3-trifluoro-N-(2-fluoro-3-(4,4,5,5-tetramethyl-1,3,2-dioxaborolan-2-yl)phenyl)propane-1-sulfonamide (SM-13)

This material was prepared according to the procedure used for SM-9, step 3: LCMS (m/z) not ionized (MH$^+$), $t_R$=0.62 minute.

Preparation of N-(2,6-difluoro-3-(4,4,5,5-tetramethyl-1,3,2-dioxaborolan-2-yl)phenyl)propane-1-sulfonamide (SM-14)

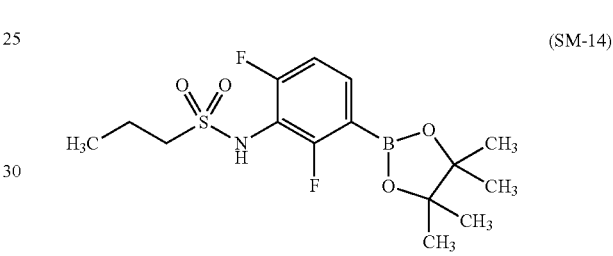

(SM-14)

Step 1. Preparation of bromo-2,6-difluorobenzoic acid

To an oven dried 2-necked round bottom flask under Argon at room temperature was added diisopropylamine (8.1 mL, 57.0 mmol) and THF (260 mL). The solution was cooled to −70° C. in a dry ice-acetone bath. n-Butyllithium (2.0 M in cyclohexane, 25.9 mL, 51.8 mmol) was added indropwise via syringe and the resulting reaction was warmed to 0° C. briefly then cooled back to −70° C. To this cold solution was added 1-bromo-2,4-difluorobenzene (5.9 mL, 52.0 mmol) dropwise via syringe. After addition, the reaction was maintained at −70° C. for 1 hour. Carbon dioxide (5-9 g pieces, previously rinsed with dry THF) were added to the solution. The Ar balloon was removed and replaced with a bubbler to allow venting. The resulting reaction was then allowed to warm to room temperature and was quenched with a saturated aqueous NH$_4$Cl solution to pH-7-8. The aqueous mixture was washed with EtOAc, acidified with aqueous 6 N HCl solution to pH-2-3, and extracted with EtOAc. The organic extract was washed with brine, dried (Na$_2$SO$_4$), filtered and concentrated in vacuo to afford 10.9 g (89%) of 3-bromo-2,6-difluorobenzoic acid: $^1$H NMR (400 MHz, DMSO-d$_6$) δ 7.25 (m, 1H) 7.92 (m, 1H).

Step 2. Preparation of tert-butyl 3-bromo-2,6-difluorophenylcarbamate

To a round bottom flask containing 3-bromo-2,6-difluorobenzoic acid (5 g, 21.1 mmol) under nitrogen with a condenser was added toluene (35 mL) and t-BuOH (35 mL). To this solution was added DIEA (4.4 ml, 25.3 mmol) and DPPA (5.7 mL, 26.4 mmol). The reaction mixture was heated to 111° C. in an oil bath for 48 hours. The reaction was allowed to cool to room temperature and the volatiles were removed in vacuo. The resulting residue was suspended with water and extracted with EtOAc. The organic phase was washed with water, brine, dried (Na$_2$SO$_4$), filtered and concentrated onto silica. Purification by flash chromatography (SiO$_2$; 0-100% EtOAc in heptane) afforded 3.49 g (54%) of tert-butyl 3-bromo-2,6-difluorophenylcarbamate: $^1$H NMR (400 MHz, DMSO-d$_6$) δ 1.34-1.54 (m, 9H) 7.17 (m, 1H) 7.63 (ddd, J=8.9, 7.9, 5.9 Hz, 1H).

Step 3. Preparation of 3-bromo-2,6-difluoroaniline

To a round bottom flask containing tert-butyl 3-bromo-2,6-difluorophenylcarbamate (1 g, 3.3 mmol) was added DCM (3 mL) and TFA (3 mL). The reaction was stirred for 2 hours at room temperature. The volatiles were removed in vacuo, and the resulting residue was neutralized with saturated aqueous NaHCO$_3$ solution to pH 8. The aqueous mixture was extracted with EtOAc. Organic phase was washed with water, brine, dried (Na$_2$SO$_4$), filtered and concentrated onto silica. Purification by flash chromatography (SiO$_2$; 0-50% EtOAc in heptane) afforded 425 mg (63%) of 3-bromo-2,6-difluoroaniline: LCMS (m/z) 208.0 (MH$^+$); t$_R$=0.80 minute; $^1$H NMR (400 MHz, DMSO-d$_6$) δ 5.54 (s, 2H) 6.78 (ddd, J=9.0, 7.4, 5.5 Hz, 1H) 6.85-6.95 (m, 1H).

Step 4. Preparation of N-(3-bromo-2,6-difluorophenyl) propane-1-sulfonamide

To a solution of 3-bromo-2,6-difluoroaniline (425 mg, 2.04 mmol) in dry pyridine (2.0 mL) was added 1-propanesulfonyl chloride (275 μL, 2.45 mmol) and the resulting reaction was maintained overnight at room temperature. The reaction was partitioned between EtOAc and water, and the layers separated. The aqueous portion was extracted with EtOAc and the combined organic portions were washed with 10% aqueous citric acid solution, water, brine, dried (Na$_2$SO$_4$), and concentrated to yield a brown viscous oil as a 2:1 mixture of 3-bromo-2,6-difluoroaniline and N-(3-bromo-2,6-difluorophenyl) propane-1-sulfonamide which was carried forward without further purification: N-(3-bromo-2,6-difluorophenyl) propane-1-sulfonamide LCMS (m/z) not ionized (MH$^+$); t$_R$=1.06 minutes.

Step 5. Preparation of N-(2,6-difluoro-3-(4,4,5,5-tetramethyl-1,3,2-dioxaborolan-2-yl)phenyl)propane-1-sulfonamide (SM-14)

The mixture of 3-bromo-2,6-difluoroaniline and N-(3-bromo-2,6-difluorophenyl) propane-1-sulfonamide (560 mg, 2.69 mmol) was combined with bis(pinacolato)diboron (820 mg, 3.23 mmol), tricyclohexylphosphine (52.8 mg, 0.188 mmol), potassium acetate (396 mg, 4.04 mmol), and Pd$_2$dba$_3$ (74.0 mg, 0.081 mmol) in 1,4-dioxane (10 mL) to give a yellow suspension. The reaction mixture was heated in a oil bath to 120° C. for 2 hours whereupon LCMS indicated complete conversion. The reaction was allowed to cool to room temperature and partitioned between EtOAc and water. The layers were separated and the aqueous portion was extracted with EtOAc. The combine organic portions were washed with water (2×), brine, dried (Na$_2$SO$_4$), and concentrated to give a dark brown oil as a mixture of boronate esters which was used without further purification: N-(2,6-difluoro-3-(4,4,5,5-tetramethyl-1,3,2-dioxaborolan-2-yl)phenyl)propane-1-sulfonamide LCMS (m/z) 174.0 (MH$^+$, boronic acid); t$_R$=0.33 minute.

Preparation of 3-methoxy-2-methyl-5-(4,4,5,5-tetramethyl-1,3,2-dioxaborolan-2-yl)aniline (SM-15)

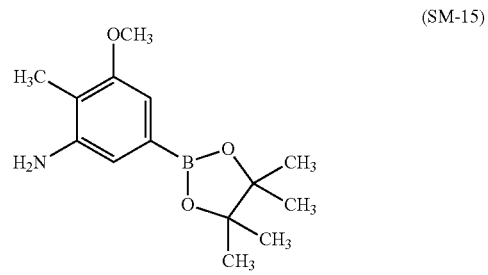 [SMILES: COc1cc(B2OC(C)(C)C(C)(C)O2)cc(N)c1C]

(SM-15)

Step 1. Preparation of 5-bromo-3-methoxy-2-methylaniline

This material was prepared from 5-bromo-1-methoxy-2-methyl-3-nitrobenzene following the procedure used for SM-9, step 2: LCMS (m/z): 216.0 (MH$^+$); t$_R$=0.65 minute.

Step 2. Preparation of 3-methoxy-2-methyl-5-(4,4,5,5-tetramethyl-1,3,2-dioxaborolan-2-yl)aniline (SM-15)

This material was prepared following the procedure used for SM-9, step 3: LCMS (m/z): 264.3 (MH$^+$); t$_R$=0.67 minute.

Preparation of 5-chloro-2-methyl-3-(4,4,5,5-tetramethyl-1,3,2-dioxaborolan-2-yl)aniline (SM-16)

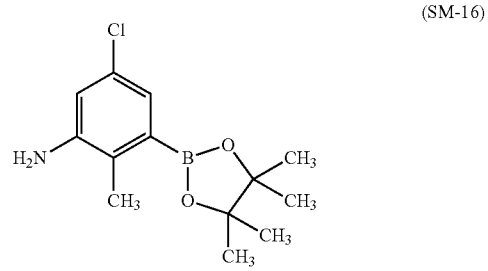 [SMILES: Cc1c(N)cc(Cl)cc1B1OC(C)(C)C(C)(C)O1]

(SM-16)

Step 1. Preparation of 3-bromo-5-chloro-2-methylaniline

This material was prepared from 1-bromo-5-chloro-2-methyl-3-nitrobenzene following the procedure used for SM-9, step 3 (96%): LCMS (m/z): 219.9 (MH$^+$); t$_R$=0.99 minute.

Step 2. Preparation of 5-chloro-2-methyl-3-(4,4,5,5-tetramethyl-1,3,2-dioxaborolan-2-yl)aniline (SM-16)

This material was prepared following the procedure used for SM-9, step 3: LCMS (m/z) 268.1 (MH$^+$); t$_R$=1.14 minutes.

Preparation of starting material 3-chloro-5-(4,4,5,5-tetramethyl-1,3,2-dioxaborolan-2-yl)aniline (SM-17)

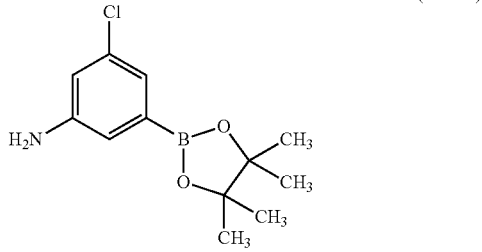
(SM-17)

This material was prepared from 3-bromo-5-chloroaniline following a similar procedure used for SM-9, step 3. The crude product was purified by flash chromatography (RediSep Cyano®, Teledyne ISCO, 0-50% EtOAc in hexanes) to afford 3-chloro-5-(4,4,5,5-tetramethyl-1,3,2-dioxaborolan-2-yl)aniline (48%) as a pale orange solid: LCMS (m/z) 172.1 (MH$^+$), $t_R$=0.33 minute.

Preparation of 3-(difluoromethoxy)-5-(4,4,5,5-tetramethyl-1,3,2-dioxaborolan-2-yl)aniline (SM-18)

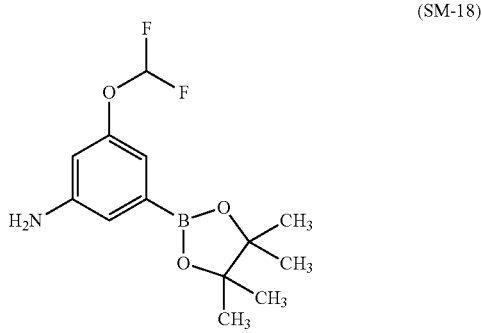 [SMILES: CC1(C)OB(c2cc(N)cc(OC(F)F)c2)OC1(C)C]
(SM-18)

Step 1. Preparation of 1-bromo-3-(difluoromethoxy)-5-nitrobenzene

To a solution of 3-bromo-5-nitrophenol (3.1 g, 14.4 mmol) and powdered sodium hydroxide (0.63 g, 15.8 mmol) in DMF (14 mL), sodium chlorodifluoroacetate (4.4 g, 28.7 mmol) was added in five portions every 0.5 hour to the warmed reaction mixture at to 55° C. The reaction was maintained at to 55° C. for 1 day and then allowed to cool to room temperature. The reaction mixture was partitioned between EtOAc and water, the layers separated, and the aqueous portion was extracted (2×25 mL) EtOAc and the combined organic layers were washed with aqueous 1.0 M NaOH solution (3×25 mL), water (3×25 mL) and brine (50 mL). The organic layer was dried (MgSO$_4$), and concentrated. The resulting residue was purified by flash chromatography (SiO$_2$, 0-50% EtOAc in hexanes) to afford 1-bromo-3-(difluoromethoxy)-5-nitrobenzene (160 mg, 0.6 mmol). $^1$H NMR (400 MHz, CDCl$_3$) δ 6.61 (t, J=71.6 Hz, 1H) 7.65 (s, 1H) 7.96 (s, 1H) 8.21-8.31 (m, 1H).

Step 2. Synthesis of 3-bromo-5-(difluoromethoxy)aniline

This material was prepared following the procedure used for SM-9, step 3. The crude product was purified by flash chromatography (SiO2, 0-30% EtOAc in hexanes) to furnish 3-bromo-5-(difluoromethoxy)aniline as a light brown oil (41% yield):
LCMS (m/z) 237.9 (MH$^+$), $t_R$=0.81 minute; $^1$H NMR (300 MHz, CDCl$_3$) δ 3.83 (br s, 2H) 6.45 (t, 1H) 6.58-6.79 (m, 1H).

Step 3. Synthesis of 3-(difluoromethoxy)-5-(4,4,5,5-tetramethyl-1,3,2-dioxaborolan-2-yl)aniline (SM-18)

This material was prepared following the procedure used for SM-9, step 3: LCMS (m/z) 204.1 (MH$^+$, boronic acid), $t_R$=0.33 minute.

Preparation of starting material N-(3-methyl-5-(4,4,5,5-tetramethyl-1,3,2-dioxaborolan-2-yl)phenyl)propane-2-sulfonamide (SM-19)

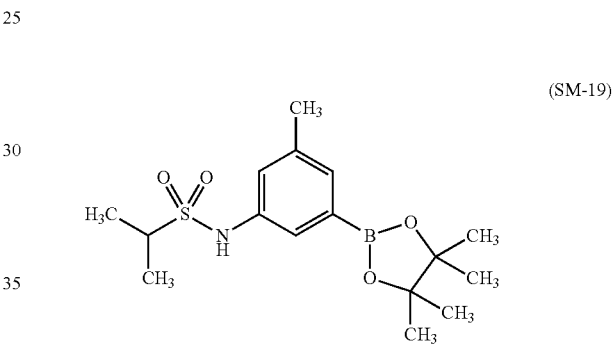
(SM-19)

Step 1. Preparation of N-(3-bromo-5-methylphenyl)propane-2-sulfonamide

To a solution of 3-bromo-5-methylaniline (500 mg, 2.2 mmol) in DCM (5 mL), isopropylsulfonylchloride (0.3 mL, 2.7 mmol) was added, followed by the addition of pyridine (0.45 mL, 5.6 mmol). The reaction was stirred at room temperature for 25 hours at which time it was quenched with water and extracted with EtOAc. The organic layer was washed with brine, dried (MgSO$_4$), and absorbed onto silica. Purification by flash chromatography (SiO$_2$, 0-30% EtOAc in hexanes) afforded N-(3-bromo-5-methylphenyl)propane-2-sulfonamide (558 mg, 1.9 mmol, 85%) as a peach colored solid: $^1$H NMR (400 MHz, CDCl$_3$) δ 1.41 (d, J=6.7 Hz, 6H) 2.31 (s, 3H) 3.33 (m, 1H) 6.84 (br s, 1H) 6.97 (s, 1H) 7.10 (s, 1H) 7.21 (s, 1H).

Step 2. Preparation of N-(3-methyl-5-(4,4,5,5-tetramethyl-1,3,2-dioxaborolan-2-yl)phenyl)propane-2-sulfonamide This material was prepared following the procedure used for SM-9, step 3 and was used as is in the next step.

Preparation of 2,5-dichloro-3-(4,4,5,5-tetramethyl-1,3,2-dioxaborolan-2-yl)aniline (SM-20)

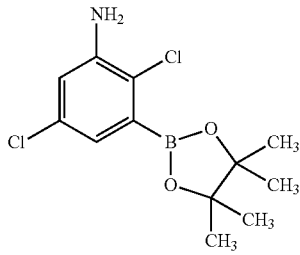
(SM-20)

Step 1. Preparation of 2,5-dichloro-3-nitrobenzoic acid

To a solution of 2,5-dichlorobenzoic acid (3 g, 15.7 mmol) in $H_2SO_4$ (16 mL) at 0° C. was added dropwise fuming nitric acid (1.4 mL, 31.4 mmol) and the reaction mixture was stirred for 5 minutes at 0° C., and was then gradually allowed to warm to over 20 minutes. The reaction was treated with ice water and extracted with EtOAc. The organic layer was washed with water and brine then dried ($Na_2SO_4$), filtered and concentrated to afford 3.54 g (48%) of 2,5-dichloro-3-nitrobenzoic acid which is contaminated with 3,6-dichloro-2-nitrobenzoic acid (40%): $^1$H NMR (300 MHz, $CD_3OD$) δ 7.73 (s, 1H) 8.06 (d, J=2.6 Hz, 1H) 8.11 (d, J=2.6 Hz, 1H).

Step 2. Preparation of 1-bromo-2,5-dichloro-3-nitrobenzene

To an oven dried round bottom flask equipped with stir bar and condenser, under nitrogen at room temperature was added 2,5-dichloro-3-nitrobenzoic acid (3.54 g, 15.00 mmol as a mixture with 3,6-dichloro-2-nitrobenzoic acid), mercuric oxide, red (4.87 g, 22.50 mmol) and carbon tetrachloride (100 mL). The reaction mixture was heated to 90° C. for 30 minutes with irradiation from a 150 W TYPE A utility light bulb. The reaction mixture was then cooled to approximately 60° C. and bromine (1.2 mL, 22.5 mmol) was added dropwise via a syringe. The nitrogen atmosphere was replaced with an argon balloon and the reaction mixture was heated again to 90° C. for 4 hours with constant light irradiation. The reaction mixture was then cooled to room temperature, quenched with saturated aqueous $NaHCO_3$ solution, stirred for 2 hours, filtered through Celite, and diluted with DCM. The two phases were separated and the aqueous mixture was extracted with DCM. The organics were combined, washed with water, brine, dried ($Na_2SO_4$), and concentrated to a pale yellow crystalline solid which was purified by flash chromatography ($SiO_2$, 0-15% EtOAc in heptane) to afford 1.83 g (29%) of 1-bromo-2,5-dichloro-3-nitrobenzene: $^1$H NMR (300 MHz, $CDCl_3$) δ 7.75 (d, J=2.3 Hz, 1H) 7.87 (d, J=2.3 Hz, 1H).

Step 3. Preparation of 3-bromo-2,5-dichloroaniline

This material was prepared according to the procedure used for SM-9, step 2 using 1-bromo-2,5-dichloro-3-nitrobenzene. Purification by flash chromatography ($SiO_2$, 0-30% EtOAc in heptane) provided 3-bromo-2,5-dichloroaniline (24%): LCMS (m/z) 239.9 ($MH^+$), $t_R$=1.03 minutes; $^1$H NMR (400 MHz, $CDCl_3$) δ 4.28 (br s, 2H) 6.71 (d, J=2.4 Hz, 1H) 7.02 (d, J=2.4 Hz, 1H).

Step 4. Preparation of 2,5-dichloro-3-(4,4,5,5-tetramethyl-1,3,2-dioxaborolan-2-yl)aniline (SM-20)

This material was prepared according to the procedure used for SM-9, step 3. LCMS (m/z): 287.9 ($MH^+$); $t_R$=1.10 minutes.

Preparation of 2-chloro-5-methyl-3-(4,4,5,5-tetramethyl-1,3,2-dioxaborolan-2-yl)aniline (SM-21)

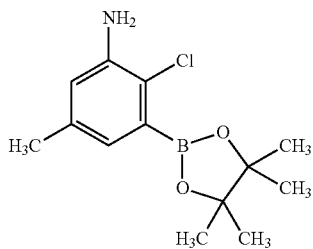
(SM-21)

Step 1. Preparation of 3-bromo-2-chloro-5-methylaniline

To an Argon sparged solution of 1,3-dibromo-2-chloro-5-methylbenzene (5 g, 17.6 mmol), benzophenone imine (3.1 mL, 18.5 mmol), sodium tert-butoxide (2.53 g, 26.4 mmol) in toluene, (S)-BINAP (1.6 g, 2.6 mmol) and $Pd_2(dba)_3$ (0.81 g, 0.88 mmol) were added and the reaction was heated in an oil bath. When the temperature reached 60° C. an exotherm was noted, with reflux of the solvent. Heating was maintained and the reaction was complete after 1.5 hours. The reaction mixture was cooled, diluted with $Et_2O$ and stirred with Siliabond DMT (Pd scavenger), and was then filtered through Celite. The filtrate was washed with water, brine, dried ($MgSO_4$), and concentrated to afford a sticky brown residue. The residue was dissolved in THF (60 mL) and aqueous 6.0 M HCl solution was added. The reaction mixture was stirred for 30 minutes, partitioned with $Et_2O$ and 1M NaOH was added until the aqueous layer was pH 9. The layers were separated and the organic layer was washed with water, brine, dried ($MgSO_4$), and concentrated. Purification by flash chromatography ($SiO_2$, 0-20% EtOAc in heptane) furnished 3-bromo-2-chloro-5-methylaniline (1.7 g) with a small amount of benzophenone as a contaminant: $^1$H NMR (300 MHz, $CDCl_3$) δ 2.21 (s, 3H) 4.11 (br s, 2H) 6.52 (s, 1H) 6.85 (s, 1H).

Step 2. Preparation of 2-chloro-5-methyl-3-(4,4,5,5-tetramethyl-1,3,2-dioxaborolan-2-yl)aniline This material was prepared following the procedure used for SM-9, step 3. $^1$H NMR (300 MHz, $CDCl_3$) δ 1.26 (s, 8H) 1.36 (s, 10H) 2.22 (s, 3H) 4.00 (br s, 2H) 6.65 (d, J=2.1 Hz, 1H) 6.89 (d, J=1.8 Hz, 1H).

Preparation of starting material 2-fluoro-5-methyl-3-(4,4,5,5-tetramethyl-1,3,2-dioxaborolan-2-yl)aniline (SM-22)

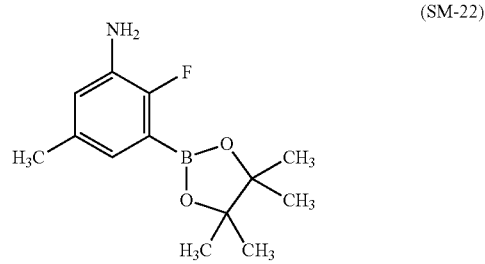

(SM-22)

Step 1. Preparation of 3-bromo-2-fluoro-5-methylbenzoic acid

To a solution of diisopropylamine (1.8 mL, 12.7 mmol) in THF (20 mL) at −10° C., n-BuLi (0.68 g, 10.6 mmol) was added and the reaction was stirred for 1 hour at −10° C. and was then cooled to −78° C. A solution of 2-bromo-1-fluoro-4-methylbenzene (2.0 g, 10.6 mmol) in THF (10 mL) was added in dropwise and the reaction was stirred for 1 hour after which excess solid carbon dioxide (4.76 g, 106 mmol) was added. After 30 minutes the reaction mixture was allowed to warm to room temperature, allowing for pressure release, and was quenched with water. The resulting layers were separated and the aqueous portion was extracted with $Et_2O$. The aqueous layer was then acidified with aqueous 6.0 M HCl solution and the resulting white precipitate was extracted into $Et_2O$. The combined organic portions were dried ($MgSO_4$), and concentrated in vacuo to afford 3-bromo-2-fluoro-5-methylbenzoic acid (2.1 g, 9.0 mmol, 85%) as a white solid: $^1$H NMR (300 MHz, $CDCl_3$) δ 2.37 (s, 3H) 7.60 (dd, J=5.9, 1.8 Hz, 1H) 7.75 (dd, J=6.2, 1.8 Hz, 1H).

Step 2. Preparation of tert-butyl 3-bromo-2-fluoro-5-methylphenylcarbamate

To a solution of 3-bromo-2-fluoro-5-methylbenzoic acid (2.1 g, 9.01 mmol) in toluene (30 mL) and t-BuOH (15 mL), DIEA (1.9 mL, 10.8 mmol) and DPPA (2.4 mL, 11.3 mmol) were added and the reaction mixture was heated to and maintained at 120° C. for 24 hours. The reaction was allowed to cool to room temperature and concentrated to afford a brown oil. The oil was partitioned between diethyl ether and water and the resulting layers separated. The diethyl ether layer was washed with water, brine, dried ($MgSO_4$) and concentrated. Purification by flash chromatography ($SiO_2$, 0-5% EtOAc in heptane) provided tert-butyl 3-bromo-2-fluoro-5-methylphenylcarbamate (985 mg, 3.2 mmol, 36%) as a clear pale yellow oil: LCMS (m/z) 247.9 (MH$^+$-t-butyl); $t_R$=1.14 minutes; $^1$H NMR (300 MHz, $CDCl_3$) δ 1.53 (s, 9H) 2.29 (s, 3H) 6.67 (br s, 1H) 6.98 (d, J=6.2 Hz, 1H) 7.88 (d, J=6.5 Hz, 1H).

Step 3. 3-Bromo-2-fluoro-5-methylaniline

To a solution of tert-butyl 3-bromo-2-fluoro-5-methylphenylcarbamate (985 mg, 3.24 mmol) in isopropyl alcohol (10 mL) was added concentrated aqueous HCl (~12 M, 2.6 mL, 32.4 mmol) and the reaction mixture was warmed to 60° C. for 2 hours, allowed to cool to room temperature, and then concentrated in vacuo to afford a white solid. The solid was dissolved in water and the resulting aqueous solution was neutralized with aqueous 1.0 M NaOH solution, and extracted with $Et_2O$. The organic phase was washed with brine, dried ($MgSO_4$) and concentrated to afford 3-bromo-2-fluoro-5-methylaniline (594 mg, 2.91 mmol, 90%) which was carried forward without further purification: $^1$H NMR (300 MHz, $CDCl_3$) δ 2.21 (s, 3H) 3.71 (br s, 2H) 6.51 (d, J=7.9 Hz, 1H) 6.70 (d, J=4.7 Hz, 1H).

Step 4. Preparation of 2-fluoro-5-methyl-3-(4,4,5,5-tetramethyl-1,3,2-dioxaborolan-2-yl)aniline (SM-22)

This material was prepared following the procedure used for SM-9, step 3: LCMS (m/z) 252.0 (MH$^+$); $t_R$=0.83 minute.

Preparation of starting material 2-chloro-4-fluoro-3-(4,4,5,5-tetramethyl-1,3,2-dioxaborolan-2-yl)aniline (SM-20)

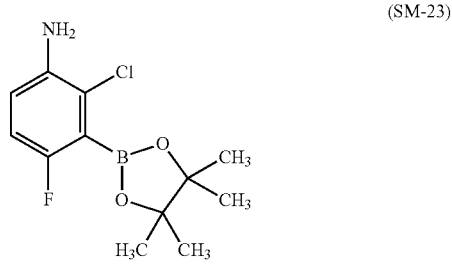 [SMILES: CC1(C)OB(c2c(F)ccc(N)c2Cl)OC1(C)C]

(SM-23)

Step 1. Preparation of 2-(2-bromo-3-chloro-1-fluoro-4-nitrobenzene)

2-Bromo-1-chloro-3-fluorobenzene (3.4 g, 16.2 mmol) was dispersed in concentrated sulfuric acid (10 mL), $NaNO_3$ (1.52 g, 17.9 mmol) was then added into the mixture in portions with stirring at 0° C. The reaction mixture was then stirred at room temperature overnight. The reaction was poured into ice water (60 mL) and allowed to stand overnight. The resulting precipitated white solid was collected by filtration, washed with water, and dissolved in EtOAc. The organic solution was washed with saturated aqueous $Na_2CO_3$ solution, brine, dried ($Na_2SO_4$), and concentrated to afford 3.8 g of a solid residue (1:7 mixture of two regioisomers, the major being the desired one). The solid was dissolved in HOAc (15 mL), cooled to 5° C., and iron powder (2.7 g, 48 mmol) was added in portions. After addition, the reaction mixture was stirred at room temperature overnight, diluted in EtOAc and then filtered through a pad of Celite. The filtrate was made alkaline (pH~12) with aqueous 12 N NaOH solution and the resulting gelatinous mixture was filtered through Celite. The filtrate partitioned upon standing and the layers separated. The aqueous portion was extracted with EtOAc (2×) and the combined organic portions were washed with brine, dried ($Na_2SO_4$) and concentrated. Purification by flash chromatography ($SiO_2$, 0-70% EtOAc in heptane) gave the desired 3-bromo-2-chloro-4-fluoroaniline (2.2 g, 9.0 mmol, 56%): LCMS (m/z) 223.8 (MH$^+$); $t_R$=0.89 minute; $^1$H NMR (400 MHz, $CDCl_3$) δ 6.92-6.88 (m, 1H), 6.71-6.66 (m, 1H), 4.05 (br s 2H).

Step 2. Preparation of 4 (2-chloro-4-fluoro-3-(4,4,5,5-tetramethyl-1,3,2-dioxaborolan-2-yl)aniline (SM-23)

This compound was prepared using the same procedure as in starting material SM-9, step 3: LCMS (m/z) 272.0 (MH$^+$); t$_R$=0.95 minute.

Preparation of Intermediate (S)-tert-butyl 1-(4-(4-bromo-2-cyclopropyl-1-((2-(trimethylsilyl)ethoxy)methyl)-1H-imidazol-5-yl)pyrimidin-2-ylamino)propan-2-ylcarbamate (I-1a)

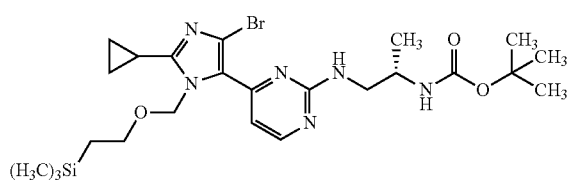

(I-1a)

Step 1. Preparation of 2-cyclopropyl-1H-imidazole

Glyoxal (40% in water) (86 mL, 749 mmol) in water (200 mL) was added to a cooled solution (5° C.) of cyclopropanecarbaldehyde (50.0 mL, 713 mmol) in methanol (100 mL) to give a colorless solution. Ammonium hydroxide (28% aq, 397 mL, 2900 mmol) was added dropwise over 1 hour at 0-5° C. The reaction was stirred for 3 hours at 0° C. and then allowed to warm to room temperature overnight. Brine (200 mL) was added to the reaction and extracted with EtOAc (4×400 mL, 4×600 mL). The combined organic layers were dried (Na$_2$SO$_4$) and concentrated to afford 2-cyclopropyl-1H-imidazole as a beige solid (70.1 g, 648 mmol, 91%). LCMS (m/z) 109.0 (MH$^+$), t$_R$=0.22 minute; $^1$H NMR (400 MHz, DMSO-d6) δ 0.73-0.81 (m, 2H), 0.81-0.88 (m, 2H), 1.85-1.95 (m, 1H), 6.78 (br s, 2H), 11.65 (br s, 1H).

Step 2. Preparation of 4,5-dibromo-2-cyclopropyl-1H-imidazole

Bromine (61 mL, 1190 mmol) was added dropwise over 2 hours to a cooled mixture of 2-cyclopropyl-1H-imidazole (70.5 g, 652 mmol) and KHCO$_3$ (118 g, 1179 mmol) in DMF (360 mL) at 0° C. Additional KHCO$_3$ (20 g, 200 mmol) was added and the reaction was stirred for another 45 minutes at 0° C. Water (1.5 L) was added dropwise over 45 minutes and the resulting orange slurry was filtered cold. The solids were washed with water (4×150 mL) and dried in a vacuum oven at 50° C. for 24 hours to furnish 4,5-dibromo-2-cyclopropyl-1H-imidazole as a tan solid (122 g, 459 mmol, 70%). LCMS (m/z) 264.8 (MH$^+$), t$_R$=0.51 minute; $^1$H NMR (400 MHz, DMSO-d6) δ 0.77-0.81 (m, 2H), 0.86-0.91 (m, 2H), 1.83-1.92 (m, 1H), 12.86 (br s, 1H).

Step 3. Preparation of 4,5-dibromo-2-cyclopropyl-1-((2-(trimethylsilyl)-ethoxy)methyl)-1H-imidazole A solution of 4,5-dibromo-2-cyclopropyl-1H-imidazole (60 g, 226 mmol) in THF (150 mL) was added dropwise over 50 minutes under nitrogen to a stirring mixture of sodium hydride (95%, 6.3 g, 250 mmol) in dry THF (150 mL) at 0° C.

The reaction mixture was stirred 30 minutes and 2-(trimethylsilyl)ethoxymethylchloride (SEMCl, 40 mL, 38 g, 226 mmol) was added dropwise over 50 minutes at 0° C. After stirring for 1 hour, the reaction was slowly quenched with water (20 mL) and added EtOAc (500 mL). The mixture was washed with water (2×750 mL) and the combined aqueous portions were back extracted with EtOAc (200 mL). The combined organic portions were washed with brine (1 L), dried (Na$_2$SO$_4$), and concentrated. The resulting residue was dissolved in heptane (200 mL) and the resulting solution was passed through a pad of silica gel, eluting with heptane (4×500 mL) and EtOAc-heptane (1:4, 2×250 mL) to give 4,5-dibromo-2-cyclopropyl-1-((2-(trimethylsilyl)ethoxy)methyl)-1H-imidazole (79 g, 199 mmol, 88%) as a pale yellow solid after concentration: LCMS (m/z) 394.9 (MH$^+$), t$_R$=1.20 minutes, $^1$H NMR (400 MHz, CDCl$_3$) δ ppm −0.04-0.05 (m, 9H), 0.87-1.12 (m, 6H), 1.88-2.04 (m, 1H), 3.55-3.66 (m, 2H), 5.37 (s, 2H).

Step 4. Preparation of 4-(4-bromo-2-cyclopropyl-1-((2-(trimethylsilyl) ethoxy)methyl)-1H-imidazol-5-yl)-2-chloro-4,5-dihydropyrimidine Butyllithium (2.0 M in pentane, 31 mL, 62 mmol) was added dropwise over 40 minutes to a solution of 4,5-dibromo-2-cyclopropyl-1-((2-(trimethylsilyl)ethoxy)methyl)-1H-imidazole (23.4 g, 59.1 mmol) in THF (175 mL) at −78° C. Reaction was stirred at −78° C. for 10 minutes. After this time, an aliquot of the reaction was quenched with water and complete lithiation was verified by LCMS. A solution of 2-chloropyrimidine (8.12 g, 70.9 mmol) in THF (20 mL) was added dropwise and stirred for 30 minutes. LCMS analysis indicated complete reaction. The reaction was quenched with saturated aqueous NH$_4$Cl solution (20 mL), allowed to warm to 0° C., and partitioned between water (500 mL) and EtOAc (500 mL). The layers were separated and the organic portion was washed with water-brine (500 mL) and brine (500 mL), then dried (Na$_2$SO$_4$) and concentrated to a yellow oil.

The crude residue was suspended in a mixture of EtOAc-hexanes (1:5, 50 mL) and heptane (50 mL) and then sonicated for 2 minutes. The resulting suspension was allowed to settle at 0° C. for 1 hour. The collected solids were washed with cold EtOAc-heptane (1:5, 50 mL) to furnish 19.6 g of 4-(4-bromo-2-cyclopropyl-1-((2-(trimethylsilyl)ethoxy)methyl)-1H-imidazol-5-yl)-2-chloro-4,5-dihydropyrimidine as a white solid. The combined filtrates were purified by flash chromatography (SiO$_2$, 20-70% EtOAc in heptane) to provide an additional 2.05 g of product (21.65 g, 50.1 mmol, 85%): LCMS (m/z) 431.0 (MH$^+$), t$_R$=0.78 minute; $^1$H NMR (400 MHz, DMSO-d6) δ ppm −0.02 (s, 9H), 0.74-0.99 (m, 6H), 1.99-2.16 (m, 1H), 3.52 (m, 2H), 4.48 (br s, 1H), 5.45 (s, 2H), 5.55 (dd, J=2.7, 1.6 Hz, 1H), 6.14 (dd, J=7.4, 1.6 Hz, 1H), 9.06-9.50 (br s, 1H).

Step 5. Preparation of 4-(4-bromo-2-cyclopropyl-1-((2-(trimethylsilyl) ethoxy)methyl)-1H-imidazol-5-yl)-2-chloropyrimidine 4-(4-Bromo-2-cyclopropyl-1-((2-(trimethylsilyl)ethoxy)methyl)-1H-imidazol-5-yl)-2-chloro-4,5-dihydropyrimidine (21.65 g, 50.1 mmol) and manganese dioxide (43.6 g, 501 mmol) in EtOAc (240 mL) was heated at reflux for 2.5 hours. The reaction mixture was cooled to room temperature and filtered through Celite. The filtrates were concentrated and the residue purified by flash column chromatography (10-40% EtOAc in heptane) to afford 4-(4-bromo-2-cyclopropyl-1-((2-(trimethylsilyl)ethoxy)methyl)-1H-imidazol-5-yl)-2- chloropyrimidine as a yellow oil (17.8 g, 41.4 mmol, 83%). LCMS (m/z) 429.0 (MH+), $t_R$=1.24 minutes; $^1$H NMR (400 MHz, CDCl$_3$) δ −0.06 (s, 9H), 0.82-0.90 (m, 2H), 1.04-1.11 (m, 2H), 1.14-1.20 (m, 2H), 2.06 (m, 1H), 3.55-3.62 (m, 2H), 5.92 (s, 2H), 7.92 (d, J=5.5 Hz, 1H), 8.62 (d, J=5.5 Hz, 1H).

Step 6. Preparation of (S)-tert-butyl-1-(4-(4-bromo-2-cyclopropyl-1-((2-(trimethylsilyl)ethoxy)methyl)-1H-imidazol-5-yl)pyrimidin-2-ylamino)propan-2-ylcarbamate (I-1a)

A mixture of 4-(4-bromo-2-cyclopropyl-1-((2-(trimethylsilyl)ethoxy)methyl)-1H-imidazol-5-yl)-2-chloropyrimidine (5.50 g, 12.8 mmol), (S)-tert-butyl 1-aminopropan-2-ylcarbamate (SM-1, 2.68 g, 15.4 mmol), diisopropylethylamine (2.68 mL, 15.4 mmol) and sodium carbonate (2.71 g, 25.6 mmol) in NMP (8 mL) was heated with 110° C. oil bath for 3.5 hours and LCMS analysis of an aliquot indicated reaction completion with desired product. The reaction was allowed to cool to ambient temperature, then partitioned between EtOAc (20 mL) and water (60 mL). The EtOAc layer was washed with water (60 mL), dried (Na$_2$SO$_4$), and concentrated to a light yellow foam (6.89 g, 12.1 mmol). A small portion of material was further purified by flash chromatography (SiO$_2$, EtOAc in heptane): LCMS (m/z) 567.3 (MH+), $t_R$=1.03 minutes; $^1$H NMR (CDCl$_3$, 300 MHz) δ −0.09 (s, 9H), 0.80 (t, J=8.2 Hz, 2H), 0.98-1.07 (m, 2H), 1.10-1.18 (m, 2H), 1.21 (t, J=6.5 Hz, 3H), 1.40 (s, 9H), 1.91-2.08 (m, 1H), 3.41 (t, J=8.2 Hz, 2H), 3.44-3.59 (m, 2H), 3.82-4.01 (m, 1H), 4.65-4.87 (m, 1H), 5.41-5.61 (m, 1H), 5.78-5.99 (m, 2H), 7.10 (d, J=5.0 Hz, 1H), 8.33 (d, J=5.2 Hz, 1H).

Preparation of Intermediate (S)-methyl 1-(4-(4-bromo-2-cyclopropyl-1H-imidazol-5-yl)pyrimidin-2-ylamino)propan-2-ylcarbamate (I-1b)

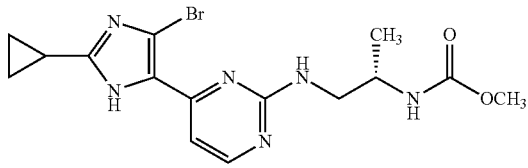

(I-1b)

Step 1. Preparation of (S)—N1-(4-(4-bromo-2-cyclopropyl-1H-imidazol-5-yl)pyrimidin-2-yl)propane-1,2-diamine, hydrogen chloride salt A solution of (S)-tert-butyl 1-(4-(4-bromo-2-cyclopropyl-1-((2-(trimethylsilyl)-ethoxy)methyl)-1H-imidazol-5-yl)pyrimidin-2-ylamino)propan-2-ylcarbamate (15.5 g, 27.3 mmol) in MeOH (60 mL) was treated with aqueous conc. HCl (37%, 10 mL, 122 mmol) at 60° C. for 3.5 hours. LCMS of an aliquot indicated complete conversion. The reaction mixture was concentrated in vacuo to obtain (S)—N1-(4-(4-bromo-2-cyclopropyl-1H-imidazol-5-yl)pyrimidin-2-yl)propane-1,2-diamine as the HCl salt (13.3 g): LCMS (m/z) 337.1 (MH+), $t_R$=0.41 minute.

Step 2. Synthesis of (S)-methyl 1-(4-(4-bromo-2-cyclopropyl-1H-imidazol-5-yl)pyrimidin-2-ylamino)propan-2-ylcarbamate (I-1b)

A mixture of (S)—N1-(4-(4-bromo-2-cyclopropyl-1H-imidazol-5-yl)pyrimidin-2-yl)propane-1,2-diamine (13.3 g, 27.3 mmol, assumed theoretical yield) in 1:1 THF-water (200 mL) was cooled to 0° C. and solid NaHCO$_3$ (20.6 g, 245 mmol) was added in portions. Methyl chloroformate (3.74 mL, 27.3 mmol) was added dropwise over 20 minutes and stirred for an additional 30 minutes. LCMS of an aliquot indicated complete reaction. Water (300 mL) was added and the resulting mixture was extracted with EtOAc (3×500 mL). The EtOAc layer was washed with brine (2×1 L), dried (Na$_2$SO$_4$) and concentrated. The resulting solid was suspended in a mixture of EtOAc (7 mL) and ethyl ether (25 mL) and the resulting suspension was allowed to settle at 0° C. The solids were collected and washed with cold Et$_2$O (20 mL) to afford (S)-methyl 1-(4-(4-bromo-2-cyclopropyl-1H-imidazol-5-yl)pyrimidin-2-ylamino)propan-2-ylcarbamate (9.56 g, 24.1 mmol, 89%) as an off-white solid: LCMS (m/z) 395.1 (MH+), $t_R$=0.61 minute; $^1$H NMR (400 MHz, CDCl$_3$) δ 0.91-1.03 (m, 2H), 1.08-1.19 (m, 2H), 1.22 (d, J=6.6 Hz, 3H), 1.77 (br s, 1H), 2.13-2.26 (m, 1H), 2.70-2.90 (m, 1H), 3.70 (s, 3H), 3.90-4.03 (m, 1H), 4.18-4.32 (m, 1H), 4.46-4.86 (m, 1H), 5.48-5.60 (m, 1H), 7.46 (d, J=5.5 Hz, 1H), 8.24 (d, J=5.4 Hz, 1H).

Preparation of Intermediate 3-(4-(4-bromo-2-cyclopropyl-1-((2-(trimethylsilyl)ethoxy)methyl)-1H-imidazol-5-yl)pyrimidin-2-ylamino)propanenitrile (I-1c)

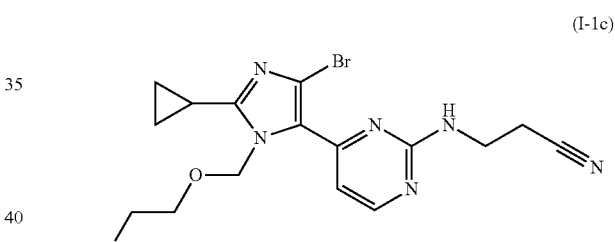

(I-1c)

A mixture of 4-(4-bromo-2-cyclopropyl-1-((2-(trimethylsilyl)ethoxy)methyl)-1H-imidazol-5-yl)-2-chloropyrimidine (I-1a, step 5, 3.50 g, 8.14 mmol), 3-aminopropionitrile (1.79 mL, 24.4 mmol), diisopropylethylamine (2.84 ml, 16.3 mmol) and Na$_2$CO$_3$ (1.73 g, 16.3 mmol) in dry NMP (4 mL) was heated at 90° C. for 8 hours. The reaction was cooled to room temperature, and then partitioned between EtOAc (100 mL) and water (100 mL), and the layers separated. The organic portion was washed with water (100 mL), saturated aqueous NaHCO$_3$ solution (100 ml), brine (100 mL), dried (Na$_2$SO$_4$) and concentrated. The crude residue was purified by flash chromatography (SiO$_2$, 0-50% EtOAc in heptane) to furnish 3-(4-(4-bromo-2-cyclopropyl-1-((2-(trimethylsilyl)ethoxy)methyl)-1H-imidazol-5-yl)pyrimidin-2-yl)propanenitrile as a pale yellow foam (2.91 g, 6.28 mmol). LCMS (m/z) 463.1 (MH+), $t_R$=0.98 minute, $^1$H NMR (CDCl$_3$) δ ppm −0.09 (s, 9H) 0.73-0.85 (m, 2H) 0.99-1.11 (m, 2H) 1.12-1.21 (m, 2H) 1.90-2.05 (m, 1H) 2.75 (t, J=6.7 Hz, 2H) 3.36-3.48 (m, 2H) 3.76 (q, J=6.5 Hz, 3H) 5.50 (br s, 1H) 5.85 (s, 2H) 7.20 (d, J=5.1 Hz, 1H) 8.37 (d, J=5.1 Hz, 1H).

Preparation of Intermediate 3-(4-(4-bromo-2-cyclopropyl-1-((2-(trimethylsilyl) ethoxy)methyl)-1H-imidazol-5-yl)pyrimidin-2-ylamino)-2-methylpropanenitrile (I-1d)

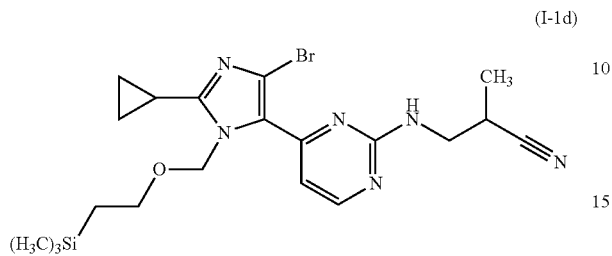

(I-1d)

A solution of 4-(4-bromo-2-cyclopropyl-1-((2-(trimethylsilyl)ethoxy)methyl)-1H-imidazol-5-yl)-2-chloropyrimidine (2.5 g, 5.8 mmol), DIEA (2.0 mL, 11.6 mmol), and 3-amino-2-methylpropanenitrile (1.49 g, 17.7 mmol) in NMP (10 mL) was treated with Na$_2$CO$_3$ (1.23 g, 11.6 mmol) and the resulting reaction mixture heated at 90° C. overnight. The reaction was allowed to cool to room temperature and was partitioned between EtOAc (75 mL) and water (100 mL). The layers were separated and the organic portion was washed with saturated aqueous NaHCO$_3$ solution (100 mL), brine (150 mL), dried (Na$_2$SO$_4$) and concentrated to a brown residue. Purification by flash chromatography (0-50% EtOAc-heptane) afforded 3-(4-(4-bromo-2-cyclopropyl-1-((2-(trimethylsilyl)ethoxy)methyl)-1H-imidazol-5-yl)pyrimidin-2-ylamino)-2-methylpropanenitrile (2.79 g, 5.8 mmol) as a white solid: LCMS (m/z) 477.1 (MH$^+$), $t_R$=0.98 minute.

Preparation of Intermediate 1-((4-(4-Bromo-2-cyclopropyl-1-((2-(trimethylsilyl)ethoxy)methyl)-1H-imidazol-5-yl)pyrimidin-2-ylamino)methyl)cyclopropanecarbonitrile (I-1e)

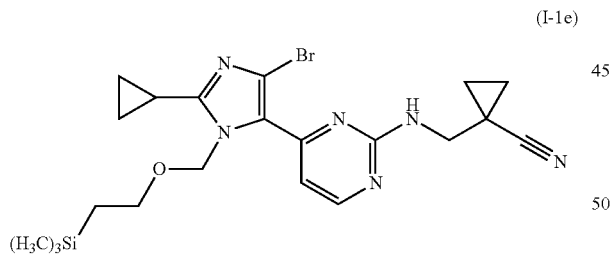

(I-1e)

A mixture of 1-(aminomethyl)cyclopropanecarbonitrile (0.67 g, 7.0 mmol), 4-(4-bromo-2-cyclopropyl-1-((2-(trimethylsilyl)ethoxy)methyl)-1H-imidazol-5-yl)-2-chloropyrimidine (2.01 g, 4.7 mmol), DIEA (1.64 ml, 9.35 mmol), Na$_2$CO$_3$ (0.99 g, 9.4 mmol) and NMP (2 mL) was heated at 110° C. for 25 hours. The reaction mixture was allowed to cool to room temperature and partitioned between EtOAc (10 mL) and water (20 mL). The layers were separated and the organic portion was sequentially washed with water (20 mL), brine (10 mL), and concentrated. The resulting residue was purified by flash chromatography on silica gel eluting with an EtOAc-heptane (0-50%) gradient to provide 1-((4-(4-bromo-2-cyclopropyl-1-((2-(trimethylsilyl)ethoxy)methyl)-1H-imidazol-5-yl)pyrimidin-2-ylamino)methyl)cyclopropanecarbonitrile (1.50 g, 3.06 mmol, 66%) as a white foam. LCMS (m/z) 491.1 (MH$^+$), $t_R$=0.99 minute.

Preparation of Intermediate 4-(4-bromo-2-cyclopropyl-1-((2-(trimethylsilyl)ethoxy)methyl)-1H-imidazol-5-yl)pyrimidin-2-amine (I-1g)

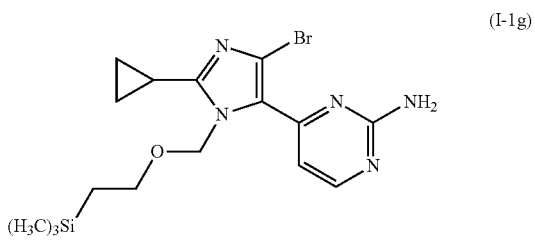

(I-1g)

4-(4-bromo-2-cyclopropyl-1-((2-(trimethylsilyl)ethoxy)methyl)-1H-imidazol-5-yl)-2-chloropyrimidine (1 g, 2.4 mmol) was combined with aqueous 28% NH$_4$OH solution (8 mL) in 1,4-dioxane (8 mL) and the resulting mixture was split evenly between two reaction vials. Each was irradiated in a microwave reactor for 40 minutes at 130° C. TLC analysis indicated complete reaction. The combined reactions were then diluted with water (100 mL) followed by extraction with EtOAc (100 mL). The EtOAc layer was washed with brine then dried (Na$_2$SO$_4$), and concentrated. Purification of the resulting residue by flash chromatography on silica gel using an EtOAc-hexanes gradient (0 to 60%) provided 0.87 g of (2.1 mmol, 91%) of 4-(4-bromo-2-cyclopropyl-1-((2-(trimethylsilyl)ethoxy)methyl)-1H-imidazol-5-yl)pyrimidin-2-amine as a white solid: LCMS (m/z): 410.0 (MH$^+$), $t_R$=0.81 minute.

Preparation of intermediate 4-(4-bromo-2-cyclopropyl-1-((2-(trimethylsilyl)ethoxy)methyl)-1H-imidazol-5-yl)pyrimidine (I-1h)

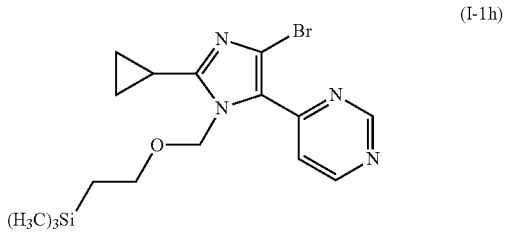

(I-1h)

Step 1. Preparation of 4-(2-cyclopropyl-1-((2-(trimethylsilyl)ethoxy)methyl)-1H-imidazol-4-yl)pyrimidine A solution of 4-(4-bromo-2-cyclopropyl-1-((2-(trimethylsilyl)ethoxy)methyl)-1H-imidazol-5-yl)-2-chloropyrimidine and ammonium formate (12.12 g, 192 mmol) in MeOH (20 mL) was sparged with Argon for 5 minutes. Pd/C (200 mg, 4.80 mmol) was added into the mixture and it was the reaction was stirred at room temperature for 5 hours. LCMS analysis of an aliquot indicated complete conversion. The reaction mixture was filtered through a pad of Celite and the filter cake was washed thoroughly with EtOAc. The combined filtrates were concentrated and the resulting residue was purified by flash chromatography using an EtOAc-hexanes gradient (0-100%) to furnish 4-(2-cyclopropyl-1-((2-(trimethylsilyl)ethoxy)methyl)-1H-imidazol-4-yl)pyrimidine (1.36 g, 4.30 mmol, 89% yield) as a light yellow sticky oil: LCMS (m/z) 317.3 (MH+), $t_R$=0.71 minute.

Step 2. Preparation of 4-(4-bromo-2-cyclopropyl-1-((2-(trimethylsilylethoxy)methyl)-1H-imidazol-5-yl)pyrimidine (I-1h)

Bromine was added to a cooled solution of 4-(2-cyclopropyl-1-((2-(trimethylsilyl)ethoxy)methyl)-1H-imidazol-4-yl)pyrimidine (1.36 g, 4.30 mmol) in DCM at 0° C. followed by saturated aqueous $Na_2CO_3$ solution (16 mL, 4.30 mmol). The reaction mixture was stirred for 3 hours at room temperature. After the reaction was judged complete by LCMS analysis, the reaction mixture was allowed to stand and partition. The resulting layers were separated and the aqueous layer was extracted with EtOAc (2×). The combine organic layers were washed with brine, dried ($Na_2SO_4$), and concentrated. The resulting residue was by flash chromatography using an EtOAc-hexanes gradient (20-80%) to give 4-(5-bromo-2-cyclopropyl-1-((2-(trimethylsilyl)ethoxy)methyl)-1H-imidazol-4-yl)pyrimidine (1.07 g, 2.71 mmol, 63%) as a yellow oil: LCMS (m/z): 395.0 (MH+), $t_R$=1.09 minutes; $^1$H NMR (400 MHz, $CDCl_3$) δ 0.00 (s, 9H) 0.80-1.50 (m, 4H) 2.06-2.25 (m, 1H) 3.49-3.65 (m, 2H) 6.05 (s, 2H) 7.95-8.07 (m, 1H) 8.82-8.94 (m, 1H) 9.27-9.34 (m, 1H).

Preparation of intermediate 3-(5-(2-chloropyrimidin-4-yl)-2-cyclopropyl-1-((2-(trimethylsilyl) ethoxy)methyl)-1H-imidazol-4-yl)-2-fluoroaniline (I-1i)

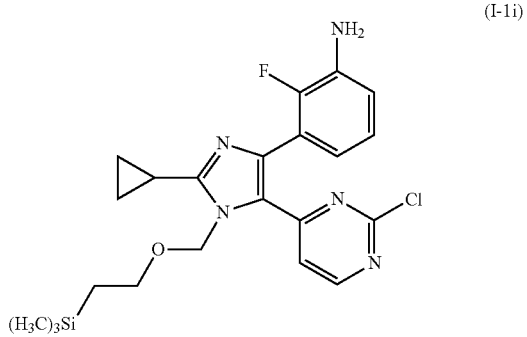

To a microwave vial with stir bar was added 4-(4-bromo-2-cyclopropyl-1-((2-(trimethylsilyl)ethoxy) methyl)-1H-imidazol-5-yl)-2-chloropyrimidine (I-1a, step 5, 0.55 g, 1.3 mmol), 2-fluoro-3-(4,4,5,5-tetramethyl-1,3,2-dioxaborolan-2-yl)aniline (0.61 g, 2.6 mmol), 2.0 M aqueous sodium carbonate solution (3.2 mL, 6.4 mmol) and DME (6.4 mL). The resulting mixture was sparged with nitrogen followed by the addition of $PdCl_2$(dppf).DCM adduct (0.052 g, 0.06 mmol). The reaction was sealed and irradiated in microwave reactor for 20 minutes at 120° C. The reaction mixture was diluted with a saturated aqueous $NH_4Cl$ solution and extracted with EtOAc. The organic phase was washed with water, brine, dried ($Na_2SO_4$), filtered, concentrated, and adsorbed onto silica gel. Purification by flash chromatography ($SiO_2$, 0-100% EtOAc in heptane) yielded 3-(5-(2-chloropyrimidin-4-yl)-2-cyclopropyl-1-((2-(trimethylsilyl)ethoxy) methyl)-1H-imidazol-4-yl)-2-fluoroaniline (223 mg, 0.48 mmol, 38%) as a viscous yellow oil: LCMS (m/z) 460.1 (MH+), $t_R$=0.95 minute.

Preparation of intermediate (S)-methyl 1-(4-(4-bromo-2-tert-butyl-1H-imidazol-5-yl)pyrimidin-2-ylamino)propan-2-ylcarbamate (I-2a)

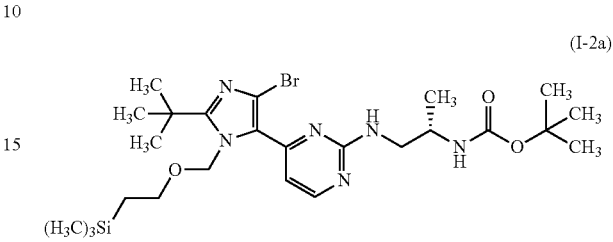

Step 1. Preparation of 2-tert-butylimidazole

A solution of glyoxal (40% in water, 16.4 g, 113.4 mmol) in water (180 mL) was added to trimethylacetaldehyde (12.4 ml, 112.6 mmol) and the resulting solution was cooled to 10° C. in an ice/water bath. To this solution was added ammonium hydroxide solution (28% in water, 56 mL) with stirring. The reaction mixture was stirred overnight and the resulting precipitate was filtered and dried to afford 12.1 g of the title compound as a white crystalline solid. LCMS (m/z): 125.10 (MH+), $t_R$=0.26 minute; $^1$H NMR (300 MHz, $CD_3OD$) δ 6.86 (2H, s), 1.32 (9H, s).

Step 2. Preparation of 4,5-dibromo-2-tert-butyl-1H-imidazole

Bromine (8.4 g, 52.42 mmol) was added dropwise to a mixture of 2-t-butylimidazole (2.6 grams, 20.97 mmol) and potassium bicarbonate (5.4 g, 52.42 mmol) in dry DMF (25 mL). The reaction mixture was then stirred at 70° C. for 4 hours. The reaction was allowed to cool to room temperature and was then filtered through a sintered funnel. The collected filtrate was cooled in an ice bath and diluted with cold water (100 mL) with stirring. The resultant precipitate was collected by filtration, washed with cold water (3×) and dried under vacuum to furnish 2.79 g of 4,5-dibromo-2-tert-butyl-1H-imidazole as a light yellow solid: LCMS (m/z): 281.0 (MH+), $t_R$=0.63 minute; $^1$H NMR (300 MHz, DMSO-$d_6$) δ 1.23 (9H, s).

Step 3. Preparation of 4,5-Dibromo-2-tert-butyl-1-((2-(trimethylsilyl)ethoxy)methyl)-1H-imidazole To a cooled solution of 2-t-butyl-4,5-dibromoimidazole (1.4 grams, 5.0 mmol; Example 5, Step 2) in dry THF (10 mL) at 0° C. was added sodium hydride (95%, 0.15 grams, 6.0 mmol) portion wise. The reaction mixture was stirred for 10 minutes at 0° C., at room temperature for 40 minutes. The reaction was re-cooled to 0° C. and SEM-chloride (0.97 ml, 5.5 mmol) was added in dropwise. The reaction mixture was stirred overnight allowing the ice bath to expire and poured into a mixture of water (30 mL) and EtOAc (50 mL). The resulting layers were partitioned and separated. The organic portion was washed with brine, then water, dried ($Na_2SO_4$), and concentrated. The remaining residue was purified by flash chromatography ($SiO_2$, 0-10% EtOAc in hexanes) to provide 2.1 g of 4,5-dibromo-2-tert-butyl-1-((2-(trimethylsilyl)ethoxy)methyl)-1H-imidazole: LCMS (m/z): 412.9 (MH⁺), $t_R$=1.320 minutes; ¹H NMR (400 MHz, CDCl₃) δ 8.75 (dd, 1H,), 7.92 (dd, 1H,), 5.90 (s, 2H), 3.51 (m, 2H), 1.55 (s, 9H), 0.82 (m, 2H), 0.08 (s, 9H).

Step 4. Preparation of 4-(4-bromo-2-tert-butyl-1-((2-(trimethylsilyl)ethoxy)methyl)-1H-imidazol-5-yl)-2-chloropyrimidine n-BuLi (1.5 M in hexane, 40 mL, 60 mmol) was added dropwise to a cooled solution of 4,5-dibromo-2-tert-butyl-1-((2-(trimethylsilyl)ethoxy)methyl)-1H-imidazole (23.6 g, 57.2 mmol) in anhydrous THF (250 mL) at −78° C. After 30 minutes at −78° C., a solution of 2-chloropyrimidine (7.21 g, 63.0 mmol) in anhydrous THF (2 mL) was added dropwise and the reaction was stirred at −78° C. for 1 hour. The reaction was quenched by the addition of saturated aqueous NH₄Cl solution and allowed to warm to room temperature. The mixture was partitioned with EtOAc and the layers separated. The aqueous portion was extracted with EtOAc (3×) and the combine organic layers were washed with water, brine, dried (MgSO₄), and concentrated. The resulting residue was dissolved in EtOAc, treated with MnO₂ (5.2 g, 60 mmol), and heated to reflux for 3 hours. The reaction was allowed to cool to room temperature and filtered through Celite. The filter cake was washed thoroughly with EtOAc and the combine filtrates were concentrated. The remaining residue was purified by flash chromatography (SiO₂, 0-10% EtOAc in hexanes) to give 10 g (37%) of 4-(4-bromo-2-tert-butyl-1-((2-(trimethylsilyl)ethoxy)methyl)-1H-imidazol-5-yl)-2-chloropyrimidine: LCMS (m/z): 445.0 (MH⁺), $t_R$=1.35 minutes. ¹H NMR (400 MHz, CDCl₃) δ 8.64 (d, J=5.3 Hz, 1H), 7.83 (d, J=5.3 Hz, 1H), 5.85 (s, 2H), 3.45 (m, 2H), 1.49 (s, 9H), 0.76 (m, 2H), −0.08 (s, 9H).

Step 5. Preparation of (S)-tert-butyl 1-(4-(4-bromo-2-tert-butyl-1-((2-(trimethylsilyl)ethoxy)methyl)-1H-imidazol-5-yl)pyrimidin-2-ylamino)propan-2-ylcarbamate (I-2a)

A mixture of 4-(4-bromo-2-tert-butyl-1-((2-(trimethylsilyl)ethoxy)methyl)-1H-imidazol-5-yl)-2-chloropyrimidine (2.0 g, 4.5 mmol;), (S)-tert-butyl-1-aminopropan-2-ylcarbamate (SM-1, 1.0 g, 5.8 mmol), and diisopropylethyl amine (2.4 mL, 13.5 mmol) in dry acetonitrile was heated at 85° C. for 16 hours. An additional charge of (S)-tert-butyl-1-aminopropan-2-ylcarbamate (145 mg, 0.8 mmol, SM-1) was added and the reaction was maintained at 85° C. for 5 hours. After allowing to cool to room temperature, the reaction was diluted with EtOAc (40 mL), washed with water (2×15 mL), dried (Na₂SO₄), and concentrated to provide 2.6 g of (S)-tert-butyl (5)-tert-butyl 1-(4-(4-bromo-2-tert-butyl-1-((2-(trimethylsilyl)ethoxy)methyl)-1H-imidazol-5-yl)pyrimidin-2-ylamino)propan-2-ylcarbamate which was carried forward without further purification: LCMS (m/z): 583.0 (MH⁺), $t_R$=1.18 minutes.

Preparation of intermediate (S)-methyl 1-(4-(4-bromo-2-tert-butyl-1H-imidazol-5-yl)pyrimidin-2-ylamino)propan-2-ylcarbamate (I-2b)

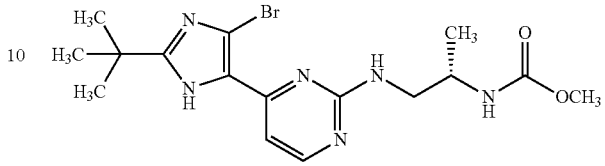

(I-2b)

To a solution of (S)-tert-butyl 1-(4-(4-bromo-2-tert-butyl-1-((2-(trimethylsilyl)ethoxy) methyl)-1H-imidazol-5-yl)pyrimidin-2-ylamino)propan-2-ylcarbamate (2.66 g, 3.94 mmol, Example 7, Step 1) in MeOH (17 mL) was added aqueous concentrated HCl (1.97 mL, 23.65 mmol) and the resulting reaction was stirred at 60° C. for 1 hour. The reaction was allowed to cool to room temperature and concentrated in vacuo to give 2.28 g of crude residue. This material was then suspended in 1:1 THF-water (100 mL) followed by the addition of NaHCO₃ (1.66 g, 19.70 mmol). The mixture was cooled to 5° C. and methyl chloroformate (1.0 M in THF, 4.33 mL, 4.33 mmol) was added dropwise. After 50 minutes, an additional charge of methyl chloroformate (1.0 M in THF, 4.33 mL, 4.33 mmol) was added and the reaction maintained for 45 minutes at 0° C. The reaction was quenched with water (300 mL) and the resulting layers were separated. The aqueous phase was extracted with EtOAc (2×200 mL) and the combined organic portions were washed with brine (2×400 mL), dried (Na₂SO₄), and concentrated. The resulting residue was triturated with 1:4 EtOAc-hexanes (10 mL) and washed with ether to provide 958 mg of (5)-methyl 1-(4-(4-bromo-2-tert-butyl-1H-imidazol-5-yl)pyrimidin-2-ylamino)propan-2-ylcarbamate: LCMS (m/z) 411.0 (MH⁺), $t_R$=0.65 minute.

Preparation of intermediate (S)-methyl 1-(4-(4-bromo-2-(1-methylcyclopropyl)-1H-imidazol-5-yl)pyrimidin-2-ylamino)propan-2-ylcarbamate (I-3a)

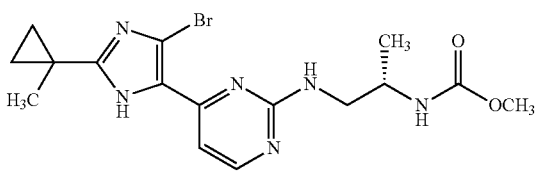

(I-3a)

Step 1. Preparation of 2-(1-methylcyclopropyl)-1H-imidazole

Pyridinium chlorochromate (PCC, 28.95 g, 134.0 mmol) was added to (1-methylcyclopropyl)methanol (9.62 g, 112.0 mmol) in THF (90 mL). The thick, black reaction mixture was stirred at room temperature for 2 hours. The reaction was filtered through Celite, and the filter pad was washed with THF (15 mL). Methanol, glyoxal and ammonium hydroxide added sequentially to the filtrate, and the reaction was stirred at room temperature overnight. The reaction mixture was concentrated until what remained was the water layer which contained solids. The solids were filtered and washed with water (10 mL). The tan solids were air dried and then dried under high vacuum to give the product as a light brown solid (3.74 g). The aqueous filtrate was extracted with EtOAc (3×500 mL). The organic layers were combined, dried ($Na_2SO_4$) and concentrated to give additional product as a brown solid (2.92 g) which was used without further purification: LCMS (m/z) 123.0 ($MH^+$), $t_R$=0.26 minute.

Step 2. Preparation of
4,5-dibromo-2-(1-methylcyclopropyl)-1H-imidazole

To a mixture of 2-(1-methylcyclopropyl)-1H-imidazole (6.66 g, 54.5 mmol) and potassium carbonate (18.83 g, 136.0 mmol) in THF (100 mL) at room temperature was added NBS (19.40 g, 109 mmol) portionwise. The reaction mixture became warm so a dry ice-acetone bath was used to cool the reaction during the addition. The resultant mixture was allowed to warm to room temperature and stirred for 3.5 hours. The reaction mixture was then diluted with EtOAc, washed sequentially with aqueous 50% $Na_2S_2O_3$ solution (2 X), water, brine, dried ($Na_2SO_4$) and concentrated to a light tan solid. The crude material was purified by dissolving in EtOAc and filtering through a pad of silica gel. The ethyl acetate fraction was concentrated and further purified by trituration with $Et_2O$ to give 4,5-dibromo-2-(1-methylcyclopropyl)-1H-imidazole as a white solid (10.44 g): LCMS (m/z) 279.0 ($MH^+$), $t_R$=0.56 minute.

Step 3. Preparation of 4,5-dibromo-2-(1-methylcyclopropyl)-1-((2-(trimethylsilyl)ethoxy)methyl)-1H-imidazole A 250 mL round-bottom flask was purged with $N_2$ and charged with NaH (95%, 0.33 g, 13.1 mmol). THF (15 mL) added, and the mixture cooled to 0° C. After 5 minutes, a solution of 4,5-dibromo-2-(1-methylcyclopropyl)-1H-imidazole (3.0 g, 10.7 mmol) in THF (20 mL) was added dropwise from an addition funnel over 5 minutes. The light tan solution was stirred at 0° C. for 25 minutes and SEMCl (2.1 mL, 11.8 mmol) was then added dropwise over 2 minutes. After 5 minutes, ice bath was removed, and the reaction stirred at room temperature. After stirring 2 hours, LCMS indicated 90% conversion. Another 0.3 mL of SEMCl (0.3 mL, 1.7 mmol) was added. LCMS indicates that the reaction has not proceeded; additional NaH (95%, 51 mg, 2.0 mmol) was added with concomitant gas evolution. After 15 minutes, LCMS indicated complete reaction. The reaction was quenched with water (1 mL). Heptane (250 mL) was added and organic layer was washed with water (200 mL). The aqueous layer was extracted with heptane (100 mL), and the combined organic layers were washed with water and brine, dried ($Na_2SO_4$), and concentrated to give 4.46 g of crude material. The crude material was purified by flash chromatography ($SiO_2$; 0-25% EtOAc in heptane) to give the product (3.45 g) as a light yellow oil: LCMS (m/z) 409.0 ($MH^+$), $t_R$=1.27 minutes.

Step 4. Preparation of 4-(4-bromo-2-(1-methylcyclopropyl)-1-((2-(trimethylsilyl) ethoxy)methyl)-1H-imidazol-5-yl)-2-chloropyrimidine To a solution of 4,5-dibromo-2-(1-methylcyclopropyl)-1-((2-(trimethylsilyl)ethoxy)methyl)-1H-imidazole (3.45 g, 6.7 mmol) in THF (50 mL) at −78° C. under nitrogen was added n-BuLi (2.0 M in pentane, 4.5 mL, 9.0 mmol), dropwise over 5 minutes. After 10 minutes, LCMS indicated complete lithiation. A solution of 2-chloropyrimidine (1.07 g, 9.3 mmol) in THF (20 mL) was added quickly from an addition funnel over one minute. The reaction was stirred at −78° C. for 1 hour and LCMS indicated complete reaction. The reaction was slowly quenched with 1:1 water-THF solution (50 mL) from an addition funnel, keeping the temperature between −40° C. and −35° C. After 15 minutes of stirring, a solution of DDQ (2.31 g, 10.2 mmol) in THF (100 mL) was added slowly, and the mixture was stirred for 15 minutes under ice water cooling. Aqueous 2.0 N NaOH solution (50 mL) was then added followed by 1:1 water-THF solution (50 mL). The resulting mixture was partitioned with EtOAc and the layers separated. The organic layer was washed with water (2×), brine (2×), dried ($Na_2SO_4$), and concentrated to give a brown oil (5.2 g). The crude material was purified by flash chromatography ($SiO_2$, 0-100% of EtOAc in heptane) to furnish 4-(4-bromo-2-(1-methylcyclopropyl)-1-((2-(trimethylsilyl)ethoxy)methyl)-1H-imidazol-5-yl)-2-chloropyrimidine (2.55 g, ~80% purity by LCMS): LCMS (m/z) 443.0 ($MH^+$), $t_R$=1.18 minutes.

Step 5. Preparation of (S)-tert-butyl 1-(4-(4-bromo-2-(1-methylcyclopropyl)-1-(2-(trimethylsilyl)ethoxy)methyl)-1H-imidazol-5-yl)pyrimidin-2-ylamino) propan-2-ylcarbamate A mixture of 4-(4-bromo-2-(1-methylcyclopropyl)-1-((2-(trimethylsilyl)-ethoxy)methyl)-1H-imidazol-5-yl)-2-chloropyrimidine (2.55 g, 5.75 mmol), (S)-tert-butyl 1-aminopropan-2-ylcarbamate (1.95 g, 11.2 mmol) and diisopropyl ethylamine (3.3 mL, 18.6 mmol) in dry ACN (10 mL) was stirred at 80° C. for 18 hours, and then at room temperature over 2 days. The reaction mixture was diluted with EtOAc, washed with water (2×), brine, dried ($Na_2SO_4$), and concentrated to give a yellow oil (4.68 g). The crude material was purified by flash chromatography ($SiO_2$, 0-60% EtOAc in heptane) to provide (S)-tert-butyl 1-(4-(4-bromo-2-(1-methylcyclopropyl)-1-((2-(trimethylsilyl)ethoxy)methyl)-1H-imidazol-5-yl)pyrimidin-2-ylamino)propan-2-ylcarbamate (2.46 g, 5.5 mmol) as a white foam: LCMS (m/z) 581.1 ($MH^+$), $t_R$=1.00 minute.

Step 6. Preparation of (S)—N1-(4-(4-bromo-2-(1-methylcyclopropyl)-1H-imidazol-5-yl)pyrimidin-2-yl)propane-1,2-diamine A mixture of (S)-tert-butyl 1-(4-(4-bromo-2-(1-methylcyclopropyl)-1-((2-(trimethylsilyl)ethoxy)methyl)-1H-imidazol-5-yl)pyrimidin-2-ylamino)propan-2-ylcarbamate (2.46 g, 4.23 mmol) in concentrated HCl (1.3 mL) and MeOH (20 mL) was stirred at room temperature overnight. LCMS indicated only 30% conversion; the reaction was then heated at 60° C. for 4 hours and stirred overnight at room temperature. LCMS indicated complete conversion and the reaction mixture was concentrated to a yellow solid to afford the crude (S)—N1-(4-(4-bromo-2-(1-methylcyclopropyl)-1H-imidazol-2-yl)pyrimidin-2-yl)propane-1,2-diamine (2.02 g) as the HCl salt which is used in next step without purification: LCMS (m/z) 351.1 ($MH^+$), $t_R$=0.45 minute.

Step 7. Preparation of (S)-methyl 1-(4-(4-bromo-2-(1-methylcyclopropyl)-1H-imidazol-5-pyrimidin-2-ylamino)propan-2-ylcarbamate (I-3a)

A solution of (S)—N1-(4-(4-bromo-2-(1-methylcyclopropyl)-1H-imidazol-5-yl)pyrimidin-2-yl)propane-1,2-diamine (2.02 g, 5.8 mmol) in THF-water (1:1, 60 mL) was cooled to 0° C. and then solid NaHCO$_3$ (2.5 g, 30 mmol) was added with concomitant frothing. After 5 minutes a THF solution of methyl chloroformate (0.35 mL, 0.44 g, 4.60 mmol, freshly prepared 1.0 M solution) was added dropwise to the mixture. After 20 minutes, LCMS indicated only ~70% conversion. Additional methylchloroformate solution (0.3 M in THF, 5 mL, 1.5 mmol) was added over 5 minutes. The reaction was maintained overnight, allowing the cooling bath to expire. LCMS indicated ~90% conversion and additional methylchloroformate solution (0.3 M in THF, 5 mL, 1.5 mmol) at 0° C. over 5 minutes. After stirring at room temperature for 1 hour, LCMS indicated complete reaction. The reaction mixture was extracted with EtOAc. The organic phase was washed with brine and dried (Na$_2$SO$_4$), and concentrated to give (S)-methyl 1-(4-(4-bromo-2-(1-methylcyclopropyl)-1H-imidazol-5-yl)pyrimidin-2-ylamino)propan-2-ylcarbamate as a yellow solid (1.65 g): LCMS (m/z) 409.1 (MH$^+$), t$_R$=0.62 minute.

Preparation of intermediate 3-(4-(4-bromo-2-(1-methylcyclopropyl)-1H-imidazol-5-yl)pyrimidin-2-ylamino)propanenitrile (I-3b)

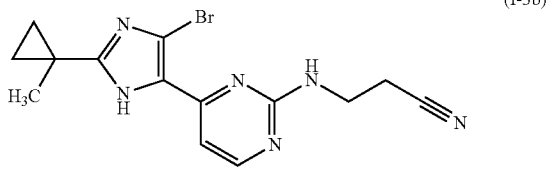

(I-3b)

Step 1. Preparation of 3-(4-(4-bromo-2-(1-methylcyclopropyl)-1-((2-(trimethylsilyl)ethoxy)methyl)-1H-imidazol-5-yl)pyrimidin-2-ylamino)propanenitrile Solid Na$_2$CO$_3$ (1.11 g, 10.5 mmol) was added to a solution of 4-(4-bromo-2-(1-methylcyclopropyl)-1-((2-(trimethylsilyl)ethoxy)methyl)-1H-imidazol-5-yl)-2-chloropyrimidine (I-3a, step 4, 2.33 g, 5.2 mmol), DIEA (1.8 mL, 10.5 mmol), and 3-aminopropionitrile (1.2 mL, 15.7 mmol) in NMP (3 mL) and the resulting reaction mixture was heated to 90° C. After 5 hours, LCMS indicated complete reaction and the reaction was allowed to cool to room temperature. EtOAc (75 mL) was added the organic phase was washed with water (100 mL), dilute aqueous NaHCO$_3$ solution (100 mL), brine (150 mL), dried (Na$_2$SO$_4$), and concentrated. Purification of the resulting residue by flash chromatography (SiO$_2$, 0-50% EtOAc in heptane) provided 3-(4-(4-bromo-2-(1-methylcyclopropyl)-1-((2-(trimethylsilyl)ethoxy)methyl)-1H-imidazol-5-yl)pyrimidin-2-ylamino)propanenitrile (2.47 g, 5.2 mmol, 99% yield) as a foamy off-white solid: LCMS (m/z) 477.1 (MH$^+$), t$_R$=0.98 minute.

Step 2. Preparation of 3-(4-(4-bromo-2-(1-methylcyclopropyl)-1H-imidazol-5-yl)pyrimidin-2-ylamino)propanenitrile (I-3b)

To a 200 mL round-bottom flask containing 3-(4-(4-bromo-2-(1-methylcyclopropyl)-1-((2-(trimethylsilyl)ethoxy)methyl)-1H-imidazol-5-yl)pyrimidin-2-ylamino)propanenitrile (2.46 g, 5.2 mmol) were added 2-propanol (10 mL) and PPTS (1.94 g, 7.7 mmol). The reaction was heated to 90° C. in an oil bath for 3 hours, LCMS indicated 90% conversion. Additional pyridine (100 µL) and the reaction was maintained at 90° C. for another 5 hours. The reaction was allowed to cool to room temperature and to an yellow gum. Added water (100 mL), adjusted to pH 7 with saturated aqueous NaHCO$_3$ solution, and extracted with EtOAc (2×100 mL). Combined EtOAc, washed with saturated NaHCO$_3$ (1×100 mL), brine (1×100 mL), dried (Na$_2$SO$_4$), filtered, and concentrated to obtain tacky yellow solids. The residue was triturated in EtOAc-Et$_2$O (1 mL, 10 mL) to furnish 3-(4-(4-bromo-2-(1-methylcyclopropyl)-1H-imidazol-5-yl)pyrimidin-2-ylamino)propanenitrile (1.50 g, 4.10 mmol, 95% purity by LCMS) as off-white solids: LCMS (m/z) 347.0 (MH$^+$), t$_R$=0.59 minute; $^1$H NMR (400 MHz, CDCl$_3$) δ 8.31 (d, J=6.3 Hz, 1H), 7.54 (d, J=6.3 Hz, 1H), 3.88 (t, J=6.3 Hz, 2H), 2.75 (t, J=6.5 Hz, 2H), 1.47 (s, 3H), 1.22 (m, 2H), 0.84 (m, 2H).

Preparation of intermediate (S)-methyl 1-(4-(4-bromo-2-cyclobutyl-1H-imidazol-5-yl)pyrimidin-2-ylamino)propan-2-ylcarbamate (I-4a)

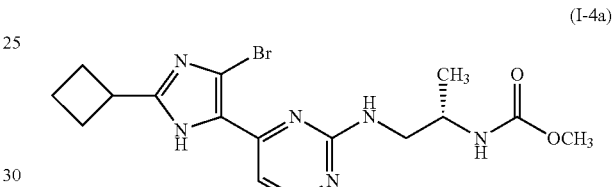

(I-4a)

Step 1. Preparation of 2-cyclobutyl-1H-imidazole

Pyridinium chlorochromate (PCC, 28.3 g, 131.0 mmol) was added to cyclobutanemethanol (10.3 mL, 109.0 mmol) in THF (90 mL). The thick, black reaction mixture was stirred at room temperature for 2 hours. The reaction was filtered through Celite, and the filter pad was washed with THF (15 mL). MeOH, glyoxal and ammonium hydroxide added sequentially to the filtrate, and the reaction was stirred at room temperature overnight. The reaction mixture was concentrated until what remained was the water layer which contained solids. The solids were filtered and washed with water (10 mL). The tan solids were air dried and then dried under high vacuum to give the product as a light brown solid (7.15 g). The aqueous filtrate was extracted with EtOAc (3×500 mL). The organic layers were combined, dried (Na$_2$SO$_4$) and concentrated to give additional product as a brown solid (2.85 g) which was used without further purification: LCMS (m/z) 123.0 (MH$^+$), t$_R$=0.28 minute.

Step 2. Preparation of 4,5-dibromo-2-cyclobutyl-1H-imidazole

To a mixture of 2-cyclobutyl-1H-imidazole (10.0 g, 82.0 mmol) and K$_2$CO$_3$ (28.32 g, 205.0 mmol) in THF (150 mL) at room temperature was added NBS (29.14 g, 164 mmol) portionwise. The reaction mixture became warm so a dry ice/acetone bath was used to cool the reaction during the addition. The resultant mixture was allowed to warm to room temperature and stirred for 3.5 hours. The reaction mixture was then diluted with EtOAc, washed sequentially with aqueous 50% Na$_2$S$_2$O$_3$ solution (2×), water, brine, dried (Na$_2$SO$_4$) and concentrated to a dark brown solid. Purification by flash chromatography (SiO$_2$, EtOAc in heptanes) gave 4,5-dibromo-2- cyclobutyl-1H-imidazole as a white solid (1.76 g, ~40 purity): LCMS (m/z) 278.8 (MH$^+$), $t_R$=0.56 minute.

Step 3. Preparation of 4,5-dibromo-2-cyclobutyl-1-((2-(trimethylsilyl) ethoxy)methyl)-1H-imidazole A 250 mL round-bottom flask was purged with nitrogen and charged with NaH (95%, 0.2 g, 8.3 mmol). THF (10 mL) added, and the mixture cooled to 0° C. After 5 minutes, a solution of 4,5-dibromo-2-cyclobutyl-1H-imidazole (1.76 g, 6.29 mmol, ~40% purity) in THF (20 mL) was added dropwise from an addition funnel over 5 minutes. The reaction was stirred at 0° C. for 35 minutes and SEMCl (1.8 mL, 10.2 mmol) was then added dropwise over 2 minutes. After 5 minutes, ice bath was removed, and the reaction stirred at room temperature for 4 hours. LCMS indicated complete reaction. The reaction was then carefully quenched with water (1.5 mL). Heptane (250 mL) was added and organic layer was washed with water (200 mL). The aqueous layer was extracted with heptane (100 mL), and the combined organic layers were washed with water and brine, dried (Na$_2$SO$_4$), and concentrated to give 2.14 g of crude material. The crude material was purified by flash chromatography (SiO$_2$; EtOAc in heptane) to afford 4,5-dibromo-2-cyclobutyl-1-((2-(trimethylsilyl)ethoxy)methyl)-1H-imidazole (0.43 g) as a yellow oil: LCMS (m/z) 408.9 (MH$^+$), $t_R$=1.25 minutes.

Step 4. Preparation of 4-(4-bromo-2-cyclobutyl-1-((2-(trimethylsilyl)ethoxy)methyl)-1H-imidazol-5-yl)-2-chloropyrimidine To a solution of 4,5-dibromo-2-cyclobutyl-1-((2-(trimethylsilyl)ethoxy)methyl)-1H-imidazole (0.43 g, 1.0 mmol) in THF (5 mL) at −78° C. under nitrogen was added n-BuLi (2.0 M in pentane, 0.68 mL, 1.36 mmol), dropwise over 5 minutes. After 40 minutes, a solution of 2-chloropyrimidine (0.17 g, 1.47 mmol) in THF (5 mL) was added dropwise over one minute. The reaction was stirred at −78° C. for 1 hour and LCMS indicated complete reaction. The reaction was slowly quenched with 1:1 water-THF solution (50 mL) from an addition funnel, keeping the temperature between −40° C. and −35° C. After 15 minutes of stirring, a solution of DDQ (0.36 g, 1.61 mmol) in THF (20 mL) was added slowly, and the mixture was stirred for 15 minutes under ice water cooling. Aqueous 2.0 N NaOH solution (12 mL) was then added followed by 1:1 water-THF solution (12 mL). The resulting mixture was partitioned with EtOAc and the layers separated. The organic layer was washed with water (2×), brine (2×), dried (Na$_2$SO$_4$), and concentrated to give a brown oil (0.45 g) as 4-(4-bromo-2-cyclobutyl-1-((2-(trimethylsilyl)ethoxy)methyl)-1H-imidazol-5-yl)-2-chloropyrimidine which was carried forward without further purification: LCMS (m/z) 443.1 (MH$^+$), $t_R$=1.27 minutes.

Step 5. Preparation of (S)-tert-butyl 1-(4-(4-bromo-2-cyclobutyl-1-((2-(trimethylsilyl)ethoxy)methyl)-1H-imidazol-5-yl)pyrimidin-2-ylamino)propan-2-ylcarbamate A mixture of 4-(4-bromo-2-cyclobutyl-1-((2-(trimethylsilyl)ethoxy)methyl)-1H-imidazol-5-yl)-2-chloropyrimidine (0.45 g, 1.01 mmol), (S)-tert-butyl 1-aminopropan-2-ylcarbamate (0.41 g, 2.35 mmol) and diisopropyl ethylamine (0.55 mL, 3.15 mmol) in dry ACN (5 mL) was stirred at 80° C. for 36 hours. The reaction mixture was allowed to cool to room temperature and diluted with EtOAc, washed with water (2×), brine, dried (Na$_2$SO$_4$), and concentrated to give a yellow oil (4.68 g). The crude material was purified by flash chromatography (SiO$_2$, 0-60% EtOAc in heptane) to provide (S)-tert-butyl 1-(4-(4-bromo-2-cyclobutyl-1-((2-(trimethylsilyl) ethoxy)methyl)-1H-imidazol-5-yl)pyrimidin-2-ylamino) propan-2-ylcarbamate (0.27 g, 5.5 mmol) as a white foam: LCMS (m/z) 581.2 (MH$^+$), $t_R$=1.10 minutes.

Step 6. Preparation of (S)—N1-(4-(4-bromo-2-cyclobutyl-1H-imidazol-5-yl)pyrimidin-2-yl)propane-1,2-diamine A mixture of ((S)-tert-butyl 1-(4-(4-bromo-2-cyclobutyl-1-((2-(trimethylsilyl)ethoxy)methyl)-1H-imidazol-5-yl)pyrimidin-2-ylamino)propan-2-ylcarbamate (0.27 g, 0.47 mmol) in concentrated HCl (0.14 mL) and MeOH (4 mL) was heated to 80° C. for 5 hours. The reaction mixture was allowed to cool to room temperature and concentrated to a yellow solid to afford the crude (S)—N1-(4-(4-bromo-2-cyclobutyl-1H-imidazol-5-yl)pyrimidin-2-yl)propane-1,2-diamine (0.25 g) as the HCl salt which is used in next step without purification: LCMS (m/z) 351.0 (MH$^+$), $t_R$=0.45 minute.

Step 7. Preparation of (S)-methyl 1-(4-(4-bromo-2-cyclobutyl-1H-imidazol-5-yl)pyrimidin-2-ylamino)propan-2-ylcarbamate (I-4a)

A solution of S)—N1-(4-(4-bromo-2-cyclobutyl-1H-imidazol-5-yl)pyrimidin-2-yl)propane-1,2-diamine (0.25 g, 0.72 mmol) in THF-water (1:1, 8 mL) was cooled to 0° C. and then solid NaHCO$_3$ (0.10 g, 1.2 mmol) was added with concomitant frothing. After 5 minutes, a THF solution of methyl chloroformate (0.1 M in THF, 4.3 mL, 0.43 mmol) was added dropwise to the mixture and the reaction was maintained overnight allowing the cooling bath to expire. LCMS indicate incomplete reaction and addition methyl chloroformate solution and NaHCO$_3$ was added. After the reaction was deemed complete by LCMS, the reaction mixture was extracted with EtOAc. The organic phase was washed with brine and dried (Na$_2$SO$_4$), and concentrated to give (S)-methyl 1-(4-(4-bromo-2-cyclobutyl-1H-imidazol-5-yl)pyrimidin-2-ylamino)propan-2-ylcarbamate as a yellow solid (0.19 g): LCMS (m/z) 409.0 (MH$^+$), $t_R$=0.63 minute.

Preparation of intermediate (S)-methyl 1-(2-(4-bromo-2-(4-(trifluoromethyl)phenyl)-1H-imidazol-5-yl)pyrimidin-4-ylamino)propan-2-ylcarbamate (I-5a)

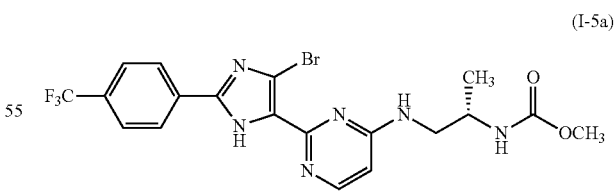

(I-5a)

Step 1. Preparation of 2,4,5-tribromo-1-((2-(trimethylsilyl)ethoxy)methyl)-1H-imidazole A dried 500 mL round bottom flask was charged with 2,4,5-tribromoimidazole (20.0 g, 65.6 mmol) and anhydrous DMF (100 mL), the resulting solution was cooled to 0° C. To this cold solution was added NaH (60% in mineral oil, 2.80 g, 70.0 mmol) portionwise with gas evolution under control and an internal temperature maintained below 10° C. After addition, the cold bath was removed and the resulting mixture was stirred at ambient temperature for 30 minutes. The reaction mixture was cooled back to 0° C., and SEMCl (12.2 mL, 69.5 mmol) was added to the reaction via syringe pump over 30 minutes. The reaction was stirred at 0° C. for an additional 30 minutes and at room temperature for another 30 minutes. The reaction was deemed complete by LCMS and the mixture was partitioned between EtOAc (150 mL) and water (300 mL), and the layers separated. The organic phase was sequentially washed with dilute aqueous NaCl (5% w/w) twice, then brine (100 mL), dried (Na$_2$SO$_4$), concentrated and a light yellow solid was obtained. The crude material was recrystallized from hot petroleum ether (30 mL) and the solids were harvested from the mother liquor at 0° C. The product was washed with cold petroleum ether (30 mL) and dried under vacuum to afford 2,4,5-tribromo-1-((2-(trimethylsilyl)ethoxy)methyl)-1H-imidazole (26.3 g, 92% yield): $^1$H NMR (400 MHz, CDCl$_3$) δ 5.31 (s, 2H), 3.59 (t, J=7.2 Hz, 2H), 0.92 (t, J=7.2 Hz, 2H), −0.01 (s, 9H).

Step 2. Preparation of 4,5-dibromo-2-(4-(trifluoromethyl)phenyl)-1-((2-(trimethylsilyl)ethoxy)methyl)-1H-imidazole In a 200 mL round-bottomed flask, 2,4,5-tribromo-1-((2-(trimethylsilyl)ethoxy)methyl)-1H-imidazole (10.2 g, 23.45 mmol), 4-(trifluoromethyl)-phenylboronic acid (5.43 g, 28.6 mmol), and aqueous 2.0 M Na$_2$CO$_3$ solution (20 mL, 40 mmol) in DME (70 mL) to give a colorless solution. The solution was sparged with Ar (3 X), Pd(PPh$_3$)$_4$ (400 mg, 0.646 mmol) was added, and the mixture was again sparged with Ar (3×). The reaction was heated to and maintained at 95° C. for 16 hours. LCMS analysis of an aliquot indicated 70% conversion. Additional 4-(trifluoromethyl)phenylboronic acid (2 g, 10.5 mmol) was added and the reaction mixture was sparged with Ar (3×). The reaction was stirred under Ar at 95° C. for another 24 hours. LCMS analysis indicated near complete conversion. The reaction was allowed to cool to room temperature and the reaction mixture partitioned upon standing. The layers were separated and the aqueous phase was extracted with EtOAc (2×20 mL). The organic layers were combined dried (Na$_2$SO$_4$), and concentrated. The resulting residue was purified by flash chromatography (SiO$_2$, 0-50% EtOAc in hexanes) to furnish 9.87 g of 4,5-dibromo-2-(4-(trifluoromethyl)phenyl)-1-((2-(trimethylsilyl)ethoxy)methyl)-1H-imidazole: LCMS (m/z) 498.9 (MH$^+$), t$_R$=1.33 minutes; NMR δ 7.98 (d, J=9.0 Hz, 2H), 7.72 (d, J=9.0 Hz, 2H), 5.32 (s, 2H), 3.74 (t, J=7.2 Hz, 2H), 0.99 (t, J=7.2 Hz, 2H), 0.03 (s, 9H).

Step 3. Preparation of 4-(4-bromo-2-(4-(trifluoromethyl)phenyl)-1-((2-(trimethylsilyl)ethoxy)methyl)-1H-imidazol-5-yl)-2-chloropyrimidine A solution of 4,5-dibromo-2-(4-(trifluoromethyl)phenyl)-1-((2-(trimethylsilyl)ethoxy)methyl)-1H-imidazole (1.0 g, 2.0 mmol) in dry THF (10 mL) was cooled to −78° C. under Argon. n-BuLi (1.0 mL, 2.5 M in hexane, 2.5 mmol) was added dropwise, afterwards the reaction was maintained below −70° C. for an additional 45 minutes. A solution of 2-chloropyrimidine (0.29 g, 2.5 mmol) in dry THF (2 mL) was added dropwise at −78° C. After addition, the reaction was allowed to warm to −40° C. over 25 minutes and maintained at −40° C. for 20 minutes. The reaction was then warmed to −5° C. in a brine-ice bath, quenched with water (30 mL), and stirred at room temperature for 30 minutes. The reaction mixture was concentrated and partitioned between EtOAc and water. The organic phase was separated, dried (Na$_2$SO$_4$), and concentrated. The resulting residue was further purified by flash chromatography (SiO$_2$, 0-20% EtOAc in hexanes) to afford 1.1 g (2.05 mmol, 82%) of 6-(4-bromo-2-(4-(trifluoromethyl)phenyl)-1-((2-(trimethylsilyl)ethoxy)methyl)-1H-imidazol-5-yl)-2-chloro-1,6-dihydropyrimidine. A solution of 6-(4-bromo-2-(4-(trifluoromethyl)phenyl)-1-((2-(trimethylsilyl)ethoxy)methyl)-1H-imidazol-5-yl)-2-chloro-1,6-dihydropyrimidine (410 mg, 0.8 mmol) in EtOAc (20 mL) was treated with MnO$_2$ (920 mg, 10.6 mmol) and the resulting reaction mixture was heated to and maintained at reflux for 18 hours. The reaction was allowed to cool to room temperature and was then filtered through Celite. The filter cake was washed with EtOAc (2×20 mL) and the combined filtrates were concentrated to give 400 mg (0.75 mmol, 98%) of 4-(4-bromo-2-(4-(trifluoromethyl)phenyl)-1-((2-(trimethylsilyl)ethoxy)methyl)-1H-imidazol-5-yl)-2-chloropyrimidine: $^1$H NMR (400 MHz, CDCl$_3$) δ 8.71 (d, J=5.4 Hz, 1H), 8.02 (d, J=5.4 Hz, 1H), 7.96 (d, J=8.1 Hz, 2H), 7.77 (d, J=8.1 Hz, 2H), 5.77 (s, 2H), 3.49 (t, J=7.5 Hz, 2H), 0.83 (t, J=7.5 Hz, 2H), 0.01 (s, 9H).

Step 3. Preparation of (S)-tert-butyl 1-(2-(4-bromo-2-(4-(trifluoromethyl)phenyl)-1-((2-(trimethylsilyl)ethoxy)methyl)-1H-imidazol-5-yl)pyrimidin-4-ylamino)propan-2-ylcarbamate:

A solution of 4-(4-bromo-2-(4-trifluoromethyl)phenyl)-1-((2-(trimethylsilyl)ethoxy)methyl)-1H-imidazol-5-yl)-2-chloropyrimidine (4.1 g, 7.7 mmol) in dry NMP (10 mL) was treated with (S)-tert-butyl-1-aminopropan-2-ylcarbamate (1.9 g, 11.0 mmol), followed by Na$_2$CO$_3$ (0.82 g, 7.7 mmol). The resulting mixture was heated to 80° C. for 4 hours whereupon the reaction was deemed complete by LCMS, and allowed to cool to room temperature. Water was added and the resulting suspension was compacted by centrifugation. The filtrate was decanted, the remaining solids were washed with water, and dried under vacuum to provide 4.6 g (6.9 mmol, 90%) as (S)-tert-butyl 1-(2-(4-bromo-2-(4-(trifluoromethyl)phenyl)-1-((2-(trimethylsilyl)ethoxy)methyl)-1H-imidazol-5-yl)pyrimidin-4-ylamino)propan-2-ylcarbamate, which was carried forward without further purification: LCMS (m/z) 671.1 (MH$^+$), t$_R$=1.21 minutes.

Step 4. Preparation of (S)—N1-(4-(4-Bromo-2-cyclobutyl-1H-imidazol-5-yl)pyrimidin-2-propane-1,2-diamine The mixture of (S)-tert-butyl 1-(2-(4-bromo-2-(4-(trifluoromethyl)phenyl)-1-((2-(trimethylsilyl)ethoxy)methyl)-1H-imidazol-5-yl)pyrimidin-4-ylamino)propan-2-ylcarbamate (0.14 g, 0.21 mmol) in concentrated HCl (0.24 mL) and MeOH (5 mL) was heated at 80° C. for 3 hours, then stirred at room temperature overnight. The reaction mixture was concentrated to a yellow solid to afford crude (S)—N1-(2-(4-bromo-2-(4-(trifluoromethyl)phenyl)-1H-imidazol-5-yl)pyrimidin-4-yl)propane-1,2-diamine (0.12 g) as the HCl salt, which is used in next step without purification: LCMS (m/z) 441.0 (MH$^+$), t$_R$=0.68 minute.

Step 5. Preparation of (S)-methyl 1-(2-(4-bromo-2-(4-(trifluoromethyl)phenyl)-1H-imidazol-5-yl)pyrimidin-4-ylamino)propan-2-ylcarbamate(I-5a)

A solution of (S)—N1-(4-(4-bromo-2-(4-(trifluoromethyl)phenyl)-1H-imidazol-5-yl)pyrimidin-2-yl)propane-1, 2-diamine (0.12 g, 0.27 mmol) in THF (6 mL) and water (4 mL) was cooled to 0° C. and then NaHCO$_3$ (0.12 g, 1.4 mmol) was added. After 5 minutes, a solution of methyl chloroformate (0.12 M in THF, 2 mL, 2.4 mmol) was added dropwise to the reaction mixture. Over 2 hours, the reaction warmed to room temperature and was extracted with EtOAc. The organic phase was washed with brine and dried (Na$_2$SO$_4$), and concentrated to give (S)-methyl 1-(2-(4-bromo-2-(4-(trifluoromethyl)phenyl)-1H-imidazol-5-yl)pyrimidin-4-ylamino)propan-2-ylcarbamate as a yellow solid (0.10 g): LCMS (m/z) 499.1 (MH$^+$), $t_R$=0.89 minute.

Preparation of intermediate (S)-methyl 1-(2-(4-bromo-2-(2,4-difluorophenyl)-1H-imidazol-5-yl)pyrimidin-4-ylamino)propan-2-ylcarbamate (I-6a)

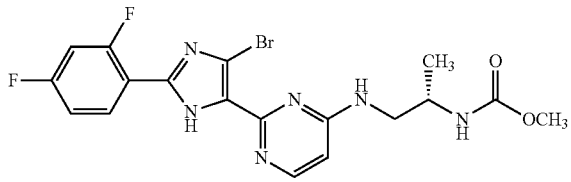 [SMILES: COC(=O)N[C@@H](C)CNc1ccnc(-c2[nH]c(-c3ccc(F)cc3F)nc2Br)n1]

(S)-methyl 1-(2-(4-bromo-2-(2,4-difluorophenyl)-1H-imidazol-5-yl)pyrimidin-4-ylamino)propan-2-ylcarbamate was prepared in a similar manner as described above: LCMS (m/z) 467.1 (MH$^+$), $t_R$=0.65 minute.

Example 1

Preparation of (S)-methyl 1-(4-(4-(5-chloro-2-fluoro-3-(methylsulfonamido)phenyl)-2-cyclopropyl-1H-imidazol-5-yl)pyrimidin-2-ylamino)propan-2-ylcarbamate, hydrogen chloride salt (1A)

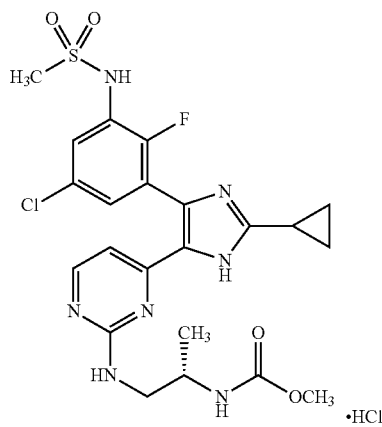

(1A)

To a solution of (S)-methyl 1-(4-(4-bromo-2-cyclopropyl-1H-imidazol-4-yl)pyrimidin-2-ylamino)propan-2-ylcarbamate (I-1b, 0.59 g, 1.5 mmol) in DME (15 mL) was added a solution of 5-chloro-2-fluoro-3-(4,4,5,5-tetramethyl-1,3,2-dioxaborolan-2-yl)aniline (SM-5, ~12 mL, 0.25 M solution in dioxane; 3.0 mmol) and aqueous Na$_2$CO$_3$ solution (6 mL, 2.0 M, 12.0 mL). The resulting mixture was sparged with nitrogen, and Pd(PPh$_3$)$_4$ (87 mg, 0.075 mmol) was added. The reaction mixture was sealed and subjected to microwave irradiation at 120° C. for about 20 minutes. The reaction was allowed to cool to room temperature and partitioned upon standing. The layers were separated and the organic portion was concentrated, dissolved in EtOAc (150 mL), washed with water (50 mL), followed by extraction with aqueous 0.01 M HCl solution (2×100 mL) and aqueous 0.02 M HCl solution (2×100 mL). The combined acidic aqueous portions were neutralized with saturated aqueous NaHCO$_3$ solution, and extracted with EtOAc (2×225 mL). The combined organic portions were washed with brine, dried (Na$_2$SO$_4$), and concentrated to yield (S)-methyl 1-(4-(4-(3-amino-5-chloro-2-fluorophenyl)-2-cyclopropyl-1H-imidazol-5-yl)pyrimidin-2-ylamino)propan-2-ylcarbamate (530 mg) which was carried forward without further purification. LCMS (m/z) 460.2 (MH$^+$), $t_R$=0.57 minute.

To a cooled solution of (S)-methyl 1-(4-(4-(3-amino-5-chloro-2-fluorophenyl)-2-cyclopropyl-1H-imidazol-5-yl)pyrimidin-2-ylamino)propan-2-ylcarbamate (530 mg, 1.2 mmol) in dry pyridine (1.2 mL) at 0-5° C., was slowly added methanesulfonyl chloride (71 µL, 0.92 mmol). After 2.5 hours, the reaction was allowed to warm to room temperature over 30 minutes after which the reaction was partitioned between EtOAc (100 mL) and water (75 mL). The layers were separated and the aqueous portion was back-extracted with EtOAc (20 mL). The combined organics were then extracted with 0.05 M NaOH (2×75 mL) and the combined basic aqueous extracts were neutralized with aqueous 0.1 M HCl solution and extracted with EtOAc (2×125 mL). The organic portion was washed with brine, dried (Na$_2$SO$_4$) and concentrated to give a brown residue which was purified by reverse phase HPLC. The combined product fractions were concentrated in vacuo. The remaining acidic aqueous solution was neutralized with saturated aqueous NaHCO$_3$ solution and extracted with EtOAc (2×100 mL). The combined organic portion was then washed with brine, dried (Na$_2$SO$_4$), and concentrated. The resulting solid was then dissolved in a solution of ACN and water and treated with one equivalent of 1.0 N aqueous HCl solution. Lyophilization afforded (S)-methyl 1-(4-(4-(5-chloro-2-fluoro-3-(methylsulfonamido)-phenyl)-2-cyclopropyl-1H-imidazol-5-yl)pyrimidin-2-ylamino)propan-2-ylcarbamate as the HCl salt (1A): LCMS (m/z): 538.1 (MH$^+$), $t_R$=0.63 minute; $^1$H NMR (400 MHz, CD$_3$CO$_2$D) δ ppm 8.27 (d, J=6.3 Hz, 1H), 7.78 (d, J=5.1, 1H), 7.51 (d, J=2.4, 1H), 6.81 (d, J=5.9, 1H), 4.06 (d, J=4.7 Hz, 1H), 3.74-3.87 (m, 1H), 3.71 (s, 3H), 3.2-3.28 (m, 1H), 3.17 (s, 3H), 2.60 (br. s., 1H), 1.50 (br s, 2H), 1.34 (d, J=7.0 Hz, 2H), 1.21 (d, J=6.7 Hz, 3H).

The compounds listed below were prepared using procedures analogous to those described above for the preparation of Example 1A using the appropriate starting materials and isolated as either their free base or salt form (generally, the trifluoroacetate or hydrogen chloride salt).

(S)-methyl 1-(4-(2-cyclopropyl-4-(2-fluoro-5-methyl-3-(methylsulfonamido)phenyl)-1H-imidazol-5-yl)pyrimidin-2-ylamino)propan-2-ylcarbamate (1B)

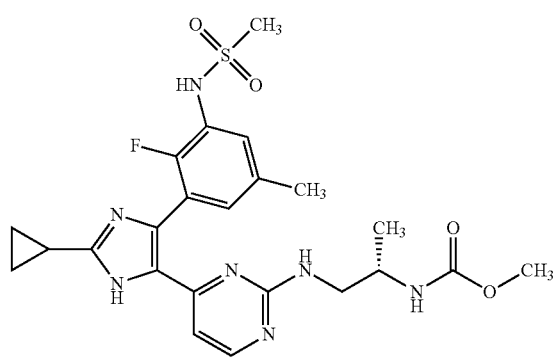

(1B)

¹H NMR (300 MHz, CD₃CO₂D) δ 1.01-1.51 (m, 7H) 2.39 (s, 3H) 2.52 (m, 1H) 3.09 (s, 3H) 3.17 (dd, J=12.9, 9.4 Hz, 1H) 3.71 (s, 3H) 3.80 (d, J=9.7 Hz, 1H) 3.98-4.22 (m, 1H) 6.63 (d, J=5.6 Hz, 1H) 7.30 (d, J=4.4 Hz, 1H) 7.53 (d, J=6.2 Hz, 1H) 8.17 (d, J=6.5 Hz, 1H). LCMS (m/z) (M+H)=518.2, Retention time (t$_R$)=0.59 minute.

(S)-Methyl 1-(4-(2-tert-butyl-4-(3-chloro-5-(methylsulfonamido)phenyl)-1H-imidazol-5-yl)pyrimidin-2-ylamino)propan-2-ylcarbamate (1C)

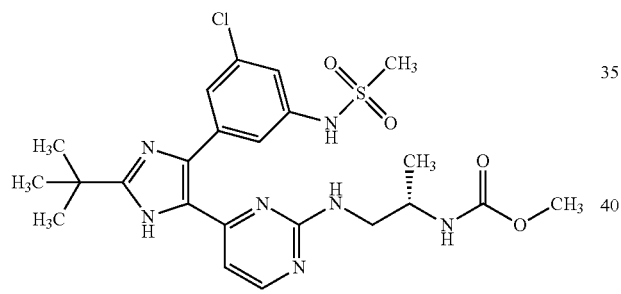

(1C)

LCMS (m/z) (M+H)=536.2, Retention time (tR)=0.50 minute.

(S)-methyl 1-(4-(2-tert-butyl-4-(3-chloro-5-(trifluoroethylsulfonamido)phenyl)-1H-imidazol-5-yl)pyrimidin-2-ylamino)propan-2-ylcarbamate (1D)

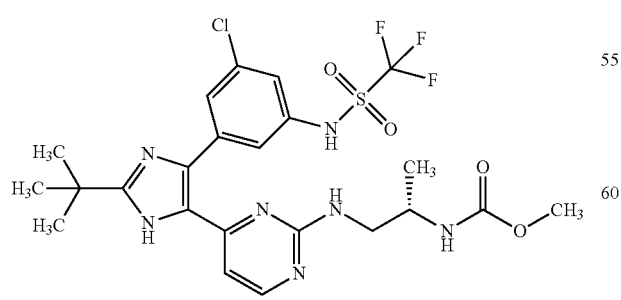

(1D)

LCMS (m/z) (M+H)=590.3, Retention time (tR)=0.87 minute.

(S)-methyl 1-(4-(2-tert-butyl-4-(3-chloro-5-(propylsulfonamido)phenyl)-1H-imidazol-5-yl)pyrimidin-2-ylamino)propan-2-ylcarbamate (1E)

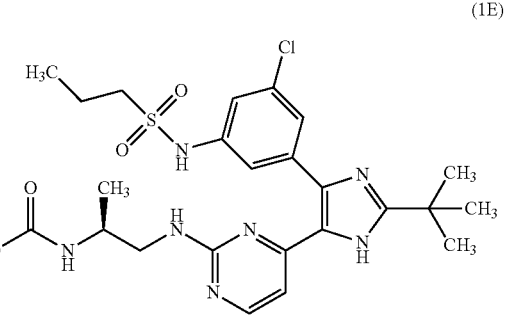

(1E)

LCMS (m/z) (M+H)=564.1, Retention time (tR)=0.72 minute.

(S)-methyl 1-(4-(2-tert-butyl-4-(3-chloro-5-(cyclopropanesulfonamido)phenyl)-1H-imidazol-5-yl)pyrimidin-2-ylamino)propan-2-ylcarbamate (1F)

(1F)

LCMS (m/z) (M+H)=562.1, Retention time (tR)=0.69 minute.

(S)-methyl 1-(4-(2-tert-butyl-4-(3-chloro-5-(2-methylpropylsulfonamido)phenyl)-1H-imidazol-5-yl)pyrimidin-2-ylamino)propan-2-ylcarbamate (1G)

(1G)

LCMS (m/z) (M+H)=578.1, Retention time (tR)=0.76 minute.

61

Methyl (2S)-1-(4-(2-tert-butyl-4-(3-chloro-5-(1-methylpropylsulfonamido)phenyl)-1H-imidazol-5-yl)pyrimidin-2-ylamino)propan-2-ylcarbamate (1H)

(1H)

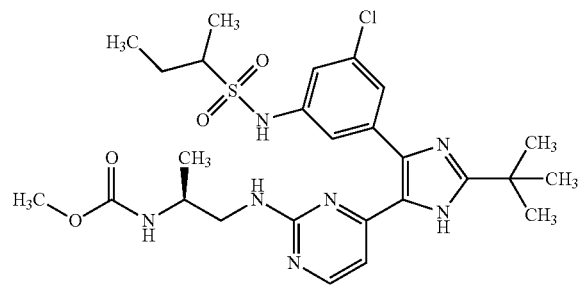

LCMS (m/z) (M+H)=578.2, Retention time (tR)=0.75 minute.

(S)-Methyl 1-(4-(2-tert-butyl-4-(3-chloro-5-(ethylsulfonamido)phenyl)-1H-imidazol-5-yl)pyrimidin-2-ylamino)propan-2-ylcarbamate (1I)

(1I)

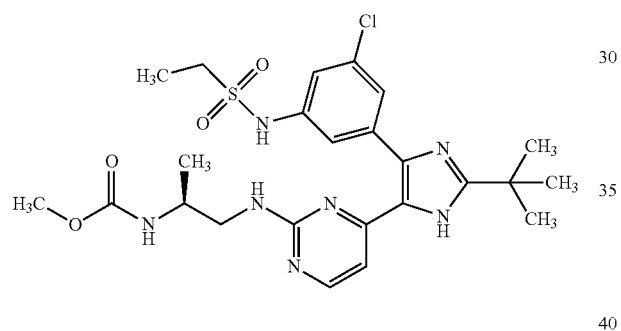

LCMS (m/z) (M+H)=550.1, Retention time (tR)=0.67 minute.

(S)-Methyl 1-(4-(2-tert-butyl-4-(3-chloro-5-(1-methylethylsulfonamido)phenyl)-1H-imidazol-5-yl)pyrimidin-2-ylamino)propan-2-ylcarbamate (1J)

(1J)

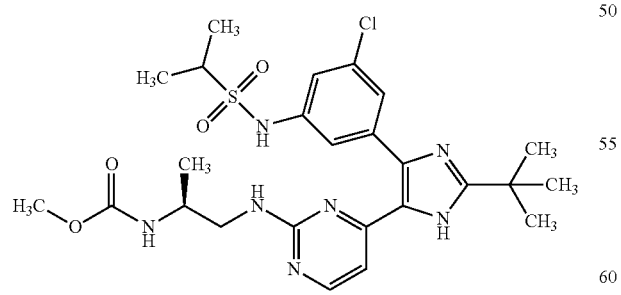

$^1$H NMR (400 MHz, CD$_3$OD) δ 0.97-1.19 (m, 3H) 1.21-1.38 (m, 6H) 1.47 (br s, 9H) 2.92-3.21 (m, 2H) 3.60 (br s, 3H) 3.75-4.13 (m, 2H) 6.39-6.77 (m, 1H) 7.27 (m, 3H) 7.90-8.34 (m, 1H). LCMS (m/z) (M+H)=564.2, Retention time (t$_R$)=0.73 minute.

62

(S)-Methyl 1-(4-(2-tert-butyl-4-(3-methoxy-4-methyl-5-(1-methylethylsulfonamido)phenyl)-1H-imidazol-5-yl)pyrimidin-2-ylamino)propan-2-ylcarbamate (1K)

(1K)

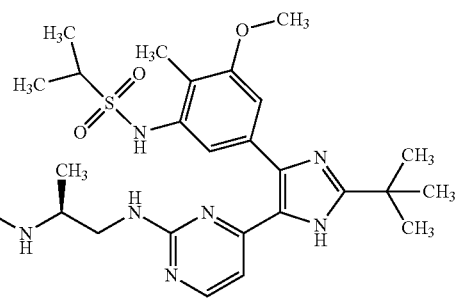

LCMS (m/z) (M+H)=574.2, Retention time (tR)=0.68 minute.

(S)-Methyl 1-(4-(2-tert-butyl-4-(3-(cyclopropanesulfonamido)-5-methoxy-4-methylphenyl)-1H-imidazol-5-yl)pyrimidin-2-ylamino)propan-2-ylcarbamate (1L)

(1L)

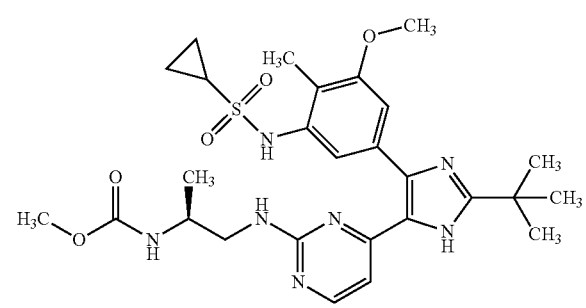

LCMS (m/z) (M+H)=572.2, Retention time (tR)=0.66 minute.

(S)-Methyl 1-(4-(4-(3-chloro-5-(1-methylethylsulfonamido)phenyl)-2-cyclopropyl-1H-imidazol-5-yl)pyrimidin-2-ylamino)propan-2-ylcarbamate (1M)

(1M)

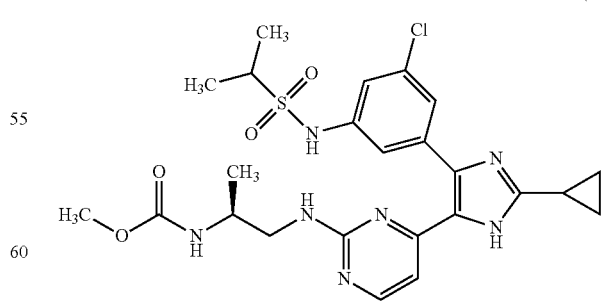

$^1$H NMR (400 MHz, CD$_3$OD) δ 1.03-1.59 (m, 13H) 2.37-2.70 (m, 1H) 3.30 (m, 6H) 3.83-4.04 (m, 1H) 6.31-6.85 (m, 1H) 7.21-7.50 (m, 3H) 8.00-8.37 (m, 1H). LCMS (m/z) (M+H)=548.3, Retention time (t$_R$)=0.66 minute.

(S)-Methyl 1-(4-(2-tert-butyl-4-(5-chloro-3-(cyclo-propanesulfonamido)-2-methylphenyl)-1H-imidazol-5-yl)pyrimidin-2-ylamino)propan-2-ylcarbamate (1N)

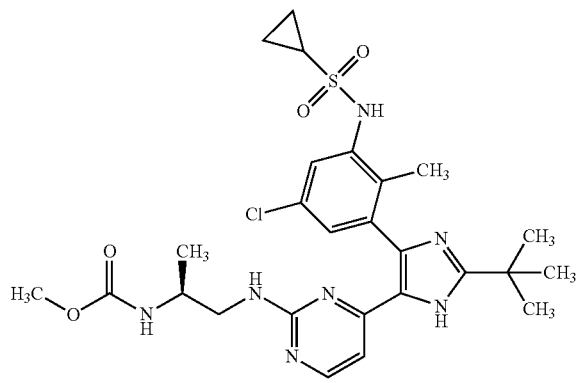

LCMS (m/z) (M+H)=576.1, Retention time (t$_R$)=0.68 minute.

(S)-Methyl 1-(4-(2-tert-butyl-4-(5-chloro-2-methyl-3-(1-methylethylsulfonamido)phenyl)-1H-imidazol-5-yl)pyrimidin-2-ylamino)propan-2-ylcarbamate (1O)

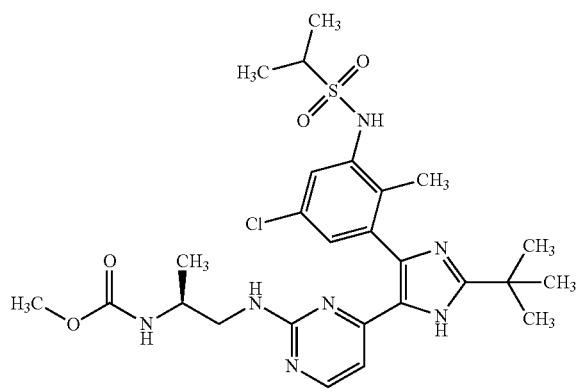

LCMS (m/z) (M+H)=578.2, Retention time (t$_R$)=0.7 minute.

(S)-Methyl 1-(4-(2-tert-butyl-5-(3-(difluoromethoxy)-5-(1-methylethylsulfonamido)phenyl)-1H-imidazol-4-yl)pyrimidin-2-ylamino)propan-2-ylcarbamate (1P)

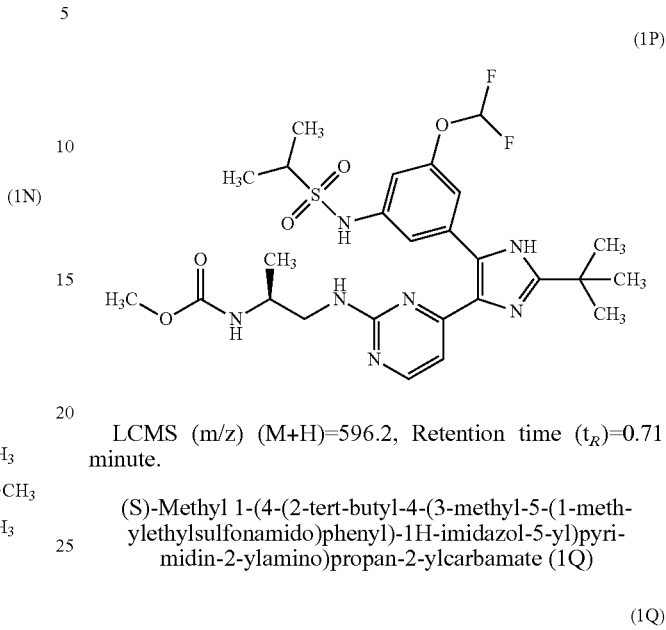

LCMS (m/z) (M+H)=596.2, Retention time (t$_R$)=0.71 minute.

(S)-Methyl 1-(4-(2-tert-butyl-4-(3-methyl-5-(1-methylethylsulfonamido)phenyl)-1H-imidazol-5-yl)pyrimidin-2-ylamino)propan-2-ylcarbamate (1Q)

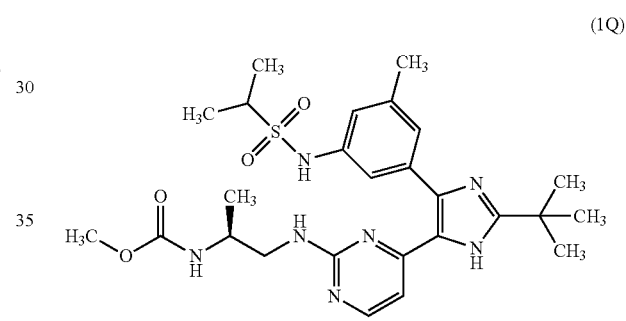

$^1$H NMR (300 MHz, CD$_3$OD) δ 1.02-1.23 (m, 3H) 1.25-1.40 (m, 6H) 1.59 (s, 9H) 2.33-2.47 (m, 3H) 3.18-3.38 (m, 2H) 3.56-3.72 (m, 4H) 3.78-4.03 (m, 1H) 6.61-6.84 (m, 1H) 7.12-7.19 (m, 1H) 7.19-7.26 (m, 1H) 7.26-7.34 (m, 1H) 7.99-8.33 (m, 1H). LCMS (m/z) (M+H)=544.4, Retention time (t$_R$)=0.65 minute.

(S)-Methyl 1-(4-(2-tert-butyl-4-(3-(methylsulfonamido)phenyl)-1H-imidazol-5-yl)pyrimidin-2-ylamino)propan-2-ylcarbamate (1R)

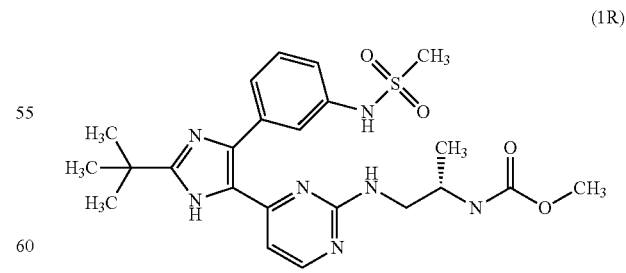

$^1$H NMR (400 MHz, CD$_3$OD) δ 1.11 (br s, 3H) 1.49-1.69 (s, 9H) 3.02 (s, 3H) 3.35-3.54 (m, 1H) 3.62 (s, 3H) 3.88 (m, 1H) 6.73 (br s, 1H) 7.32-7.44 (m, 3H) 7.49 (m, 1H) 7.55 (m, 1H) 8.17 (br s, 1H). LCMS (m/z) (M+H)=502.2, Retention time (t$_R$)=0.57 minute.

(S)-Methyl 1-(4-(4-(3-chloro-5-(methylsulfonamido)phenyl)-2-cyclopropyl-1H-imidazol-5-yl)pyrimidin-2-ylamino)propan-2-ylcarbamate (1S)

(S)-Methyl 1-(4-(2-cyclopropyl-4-(2-fluoro-3-(methylsulfonamido)phenyl)-1H-imidazol-5-yl)pyrimidin-2-ylamino)propan-2-ylcarbamate (1U)

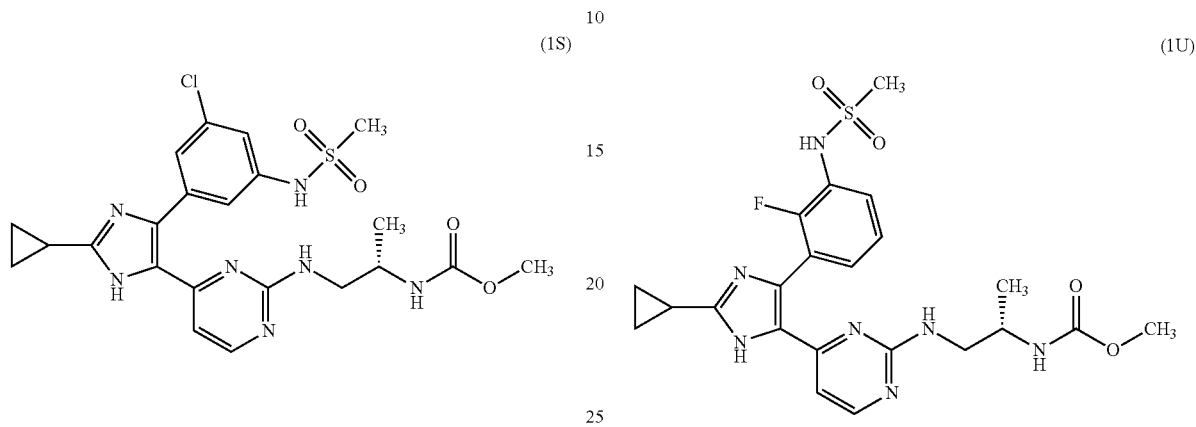

LCMS (m/z) (M+H)=520, Retention time ($t_R$)=0.59 minute.

$^1$H NMR (400 MHz, CD$_3$CO$_2$D) δ 1.21 (d, J=6.7 Hz, 3H) 1.36 (d, J=6.3 Hz, 2H) 1.54 (br s, 2H) 2.63 (d, J=4.3 Hz, 1H) 3.13 (s, 3H) 3.20 (m, 1H) 3.72 (s, 3H) 3.81 (d, J=10.6 Hz, 1H) 4.07 (d, J=3.5 Hz, 1H) 6.71 (d, J=5.9 Hz, 1H) 7.39 (m, 1H) 7.53 (m, 1H) 7.78 (m, 1H) 8.23 (d, J=6.3 Hz, 1H). LCMS (m/z) (M+H)=504, Retention time ($t_R$)=0.52 minute.

(S)-Methyl 1-(4-(4-(2-chloro-3-(methylsulfonamido)phenyl)-2-cyclopropyl-1H-imidazol-5-yl)pyrimidin-2-ylamino)propan-2-ylcarbamate (1T)

Methyl (2S)-1-(4-(2-cyclopropyl-4-(2,5-difluoro-3-(methylsulfonamido)phenyl)-1H-imidazol-5-yl)pyrimidin-2-ylamino)propan-2-ylcarbamate (1V)

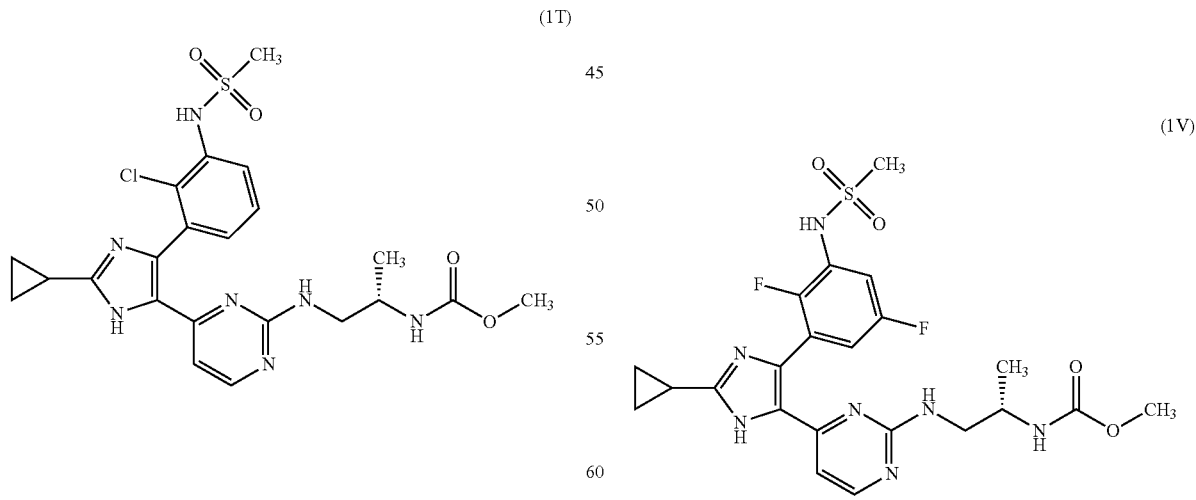

1H NMR (400 MHz, CD$_3$CO$_2$D) δ 1.21 (d, J=6.7 Hz, 3H) 1.35 (app d, J=7.8 Hz, 2H) 1.52 (br s, 2H) 2.62 (br s, 1H) 3.12 (s, 3H) 3.18 (m, 1H) 3.72 (s, 3H) 3.79 (m, 1H) 4.09 (br s, 1H) 6.46 (d, J=5.9 Hz, 1H) 7.46-7.59 (m, 2H) 7.86 (d, J=7.8 Hz, 1H) 8.18 (d, J=5.9 Hz, 1H). LCMS (m/z) (M+H)=520.2, Retention time ($t_R$)=0.53 minute.

$^1$H NMR (400 MHz, CD$_3$CO$_2$D) δ 1.11-1.36 (m, 7H) 2.39-2.54 (m, 1H) 3.07-3.29 (m, 4H) 3.60-3.85 (m, 4H) 4.06 (m, 1H) 6.3 (d, J=6.26 Hz, 1H) 7.19 (m, 1H) 7.51 (m, 1H) 8.19 (d, J=6.3 Hz, 1H). LCMS (m/z) (M+H)=522.1, Retention time ($t_R$)=0.57 minute.

67

(S)-Methyl 1-(4-(5-(5-chloro-2-fluoro-3-(propylsulfonamido)phenyl)-2-cyclopropyl-1H-imidazol-4-yl)pyrimidin-2-ylamino)propan-2-ylcarbamate (1W)

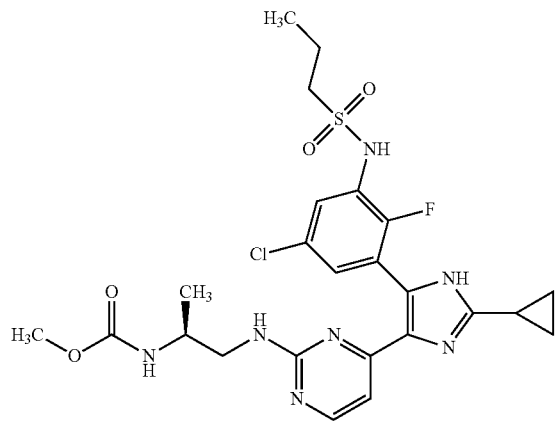

LCMS (m/z) (M+H)=566.2, Retention time (t$_R$)=0.7 minute.

(S)-Methyl 1-(4-(2-cyclopropyl-4-(2,5-dichloro-3-(methylsulfonamido)phenyl)-1H-imidazol-5-yl)pyrimidin-2-ylamino)propan-2-ylcarbamate (1X)

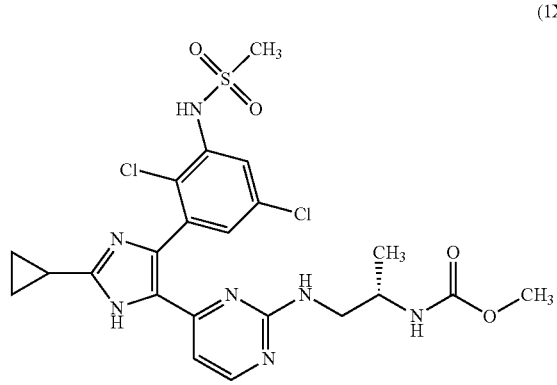

$^1$H NMR 300 MHz, CD$_3$CO$_2$D) δ 1.20 (app d, J=6.7 Hz, 5H) 1.31 (br s, 2H) 2.42-2.53 (m, 1H) 3.13 (s, 3H) 3.15-3.24 (m, 1H), 3.71 (s, 3H) 3.74-3.77 (m, 1H) 4.08 (br s, 1H) 6.45 (d, J=6.3 Hz, 1H) 7.47 (app d, J=1.6 Hz, 1H) 7.83 (d, J=2.0 Hz, 1H) 8.17 (d, J=6.7 Hz, 1H). LCMS (m/z) (M+H)=554.1, Retention time (t$_R$)=0.62 minute.

68

(S)-Methyl 1-(4-(5-(5-chloro-3-(cyclopropanesulfonamido)-2-fluorophenyl)-2-cyclopropyl-1H-imidazol-4-yl)pyrimidin-2-ylamino)propan-2-ylcarbamate (1Y)

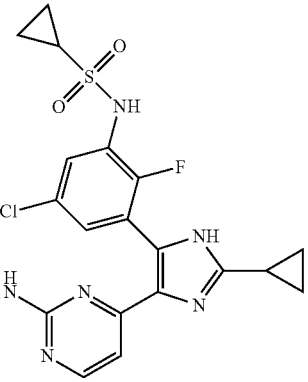

LCMS (m/z) (M+H)=564.1, Retention time (t$_R$)=0.68 minute.

(S)-Methyl 1-(4-(5-(5-chloro-3-(ethylsulfonamido)-2-fluorophenyl)-2-cyclopropyl-1H-imidazol-4-yl)pyrimidin-2-ylamino)propan-2-ylcarbamate (1Z)

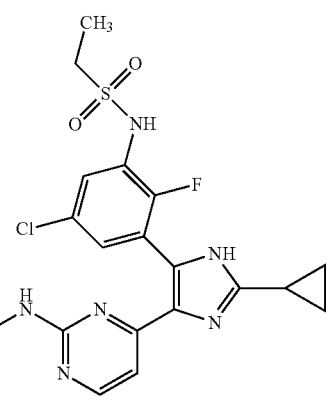

LCMS (m/z) (M+H)=552.1, Retention time (t$_R$)=0.66 minute.

(S)-Methyl 1-(4-(5-(5-chloro-2-fluoro-3-(3,3,3-trifluoropropylsulfonamido)phenyl)-2-cyclopropyl-1H-imidazol-4-yl)pyrimidin-2-ylamino)propan-2-ylcarbamate (1AA)

(S)-Methyl 1-(4-(5-(5-chloro-3-(cyclopropylmethylsulfonamido)-2-fluorophenyl)-2-cyclopropyl-1H-imidazol-4-yl)pyrimidin-2-ylamino)propan-2-ylcarbamate (1AC)

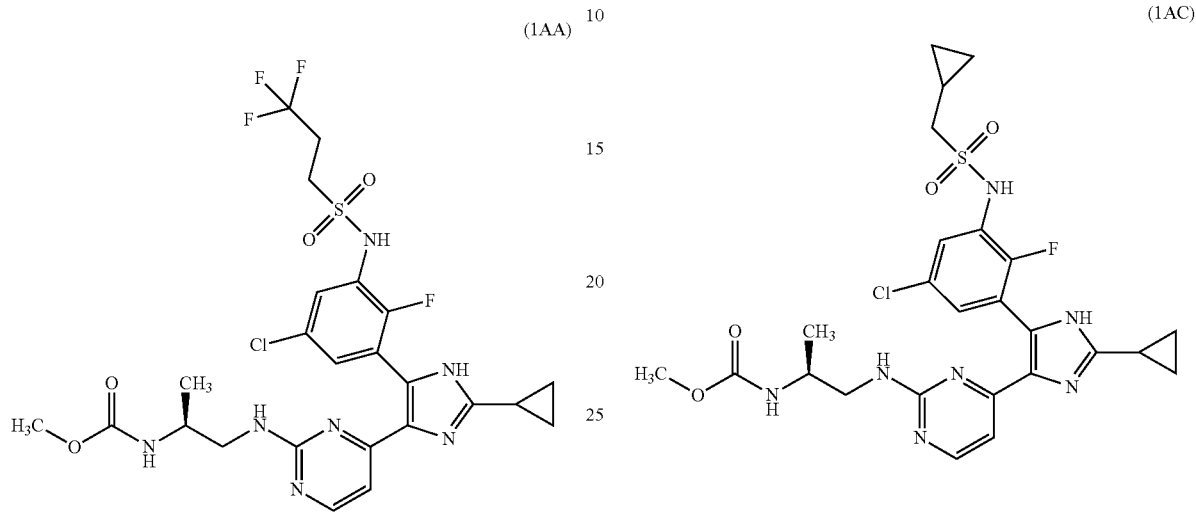

LCMS (m/z) (M+H)=620.1, Retention time ($t_R$)=0.76 minute.

LCMS (m/z) (M+H)=578.2, Retention time ($t_R$)=0.66 minute.

(S)-Methyl 1-(4-(4-(2-chloro-5-methyl-3-(methylsulfonamido)phenyl)-2-cyclopropyl-1H-imidazol-5-yl)pyrimidin-2-ylamino)propan-2-ylcarbamate (1AB)

(S)-Methyl 1-(4-(4-(2-chloro-3-(ethylsulfonamido)-5-fluorophenyl)-2-cyclopropyl-1H-imidazol-5-yl)pyrimidin-2-ylamino)propan-2-ylcarbamate (1AD)

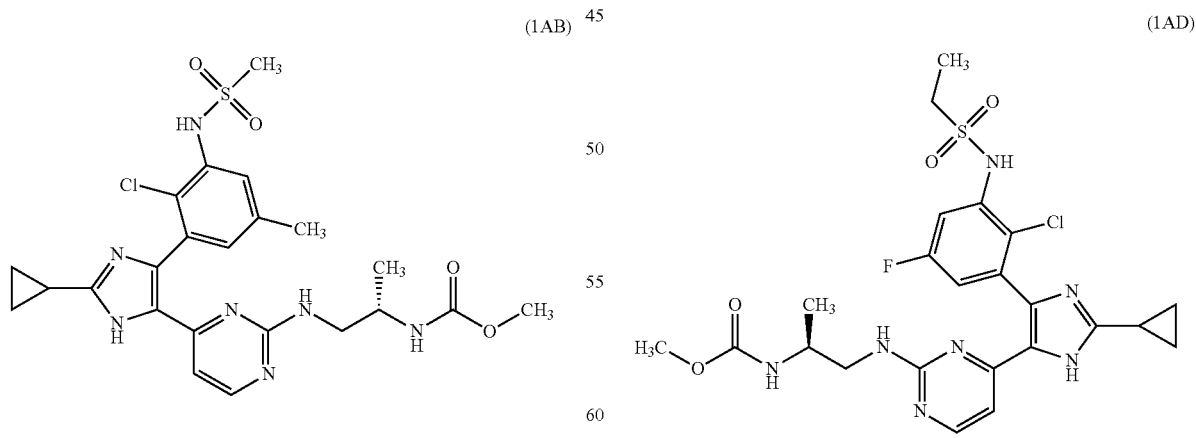

$^1$H NMR (400 MHz, $CD_3CO_2D$) δ 1.13-1.47 (m, 7H) 2.41 (s, 3H) 2.46-2.55 (m, 1H) 3.08 (s, 3H) 3.17 (dd, J=12.7, 9.6 Hz, 1H) 3.63-3.85 (m, 4H) 4.02-4.18 (m, 1H) 6.41 (d, J=6.3 Hz, 1H) 7.30 (br s, 1H) 7.64 (s, 1H) 8.14 (d, J=6.3 Hz, 1H). LCMS (m/z) (M+H)=534.4, Retention time ($t_R$)=0.55 minute.

$^1$H NMR (400 MHz, $CD_3CO_2D$) δ 1.20 (d, J=7.0 Hz, 7H) 1.33-1.40 (m, 3H) 2.41-2.55 (m, 1H) 3.13-3.33 (m, 3H) 3.71 (s, 4H) 4.03-4.17 (m, 1H) 6.35-6.45 (m, 1H) 7.16-7.26 (m, 1H) 7.61-7.71 (m, 1H) 8.12-8.24 (m, 1H). LCMS (m/z) (M+H)=552.1, Retention time ($t_R$)=0.59 minute.

(S)-Methyl 1-(4-(4-(2-chloro-3-(cyclopropane-sulfonamido)-5-fluorophenyl)-2-cyclopropyl-1H-imidazol-5-yl)pyrimidin-2-ylamino)propan-2-ylcarbamate (1AE)

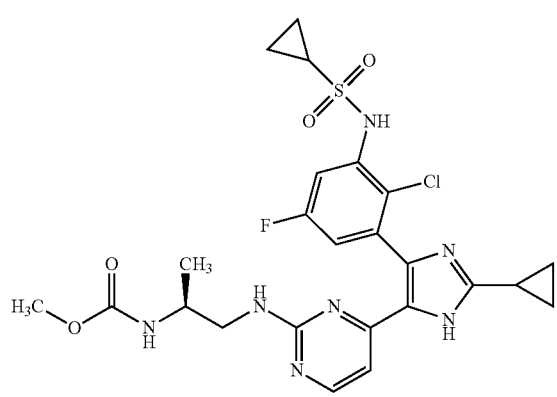

(1AE)

$^1$H NMR (400 MHz, CD$_3$CO$_2$D) δ 0.99-1.06 (m, 2H) 1.10-1.17 (m, 2H) 1.17-1.26 (m, 4H) 1.27-1.38 (m, 3H) 2.42-2.54 (m, 1H) 2.64-2.75 (m, 1H) 3.12-3.25 (m, 1H) 3.72 (s, 4H) 4.03-4.17 (m, 1H) 6.33-6.44 (m, 1H) 7.19-7.28 (m, 1H) 7.59-7.69 (m, 1H) 8.13-8.20 (m, 1H). LCMS (m/z) (M+H)=564.2, Retention time (t$_R$)=0.61 minute.

Methyl (2S)-1-(4-(4-(2-chloro-6-fluoro-3-(propylsul-fonamido)phenyl)-2-cyclopropyl-1H-imidazol-5-yl)pyrimidin-2-ylamino)propan-2-ylcarbamate (1AF)

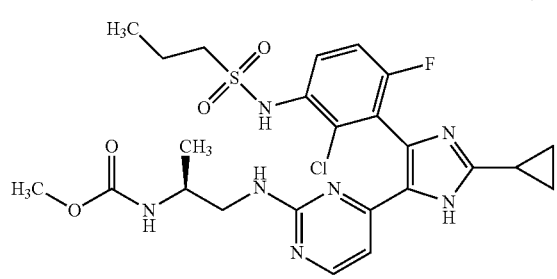

(1AF)

LCMS (m/z) (M+H)=566.2, Retention time (t$_R$)=0.618 minute.

(S)-Methyl 1-(4-(2-tert-butyl-4-(2-chloro-5-fluoro-3-(methylsulfonamido)phenyl)-1H-imidazol-5-yl)pyrimidin-2-ylamino)propan-2-ylcarbamate (1AG)

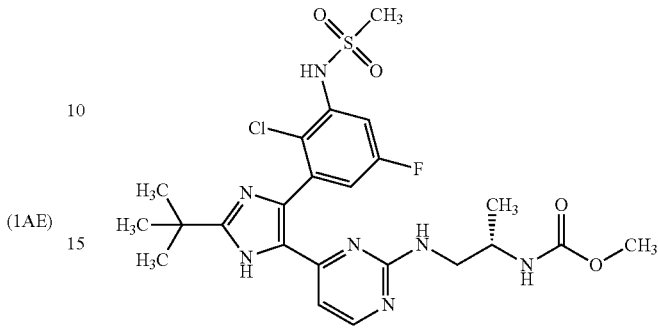

(1AG)

LCMS (m/z) (M+H)=554.1, Retention time (t$_R$)=0.63 minute.

(S)-Methyl 1-(4-(2-tert-butyl-4-(2-chloro-5-fluoro-3-(propylsulfonamido)phenyl)-1H-imidazol-5-yl)pyrimidin-2-ylamino)propan-2-ylcarbamate (1AH)

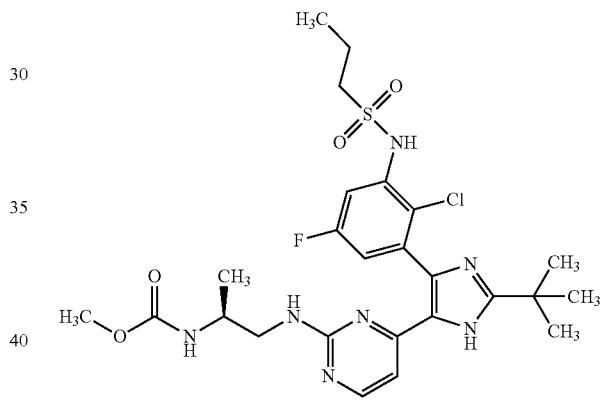

(1AH)

LCMS (m/z) (M+H)=582.2, Retention time (t$_R$)=0.70 minute.

(S)-Methyl 1-(4-(2-tert-butyl-4-(5-chloro-2-fluoro-3-(methylsulfonamido)phenyl)-1H-imidazol-5-yl)pyrimidin-2-ylamino)propan-2-ylcarbamate (1AI)

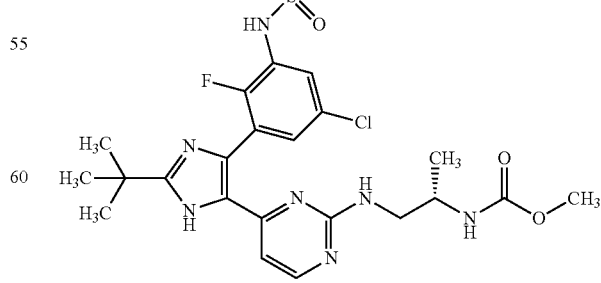

(1AI)

LCMS (m/z) (M+H)=554.2, Retention time (t$_R$)=0.67 minute.

(S)-Methyl 1-(4-(2-tert-butyl-4-(5-chloro-3-(ethyl-sulfonamido)-2-fluorophenyl)-1H-imidazol-5-yl)pyrimidin-2-ylamino)propan-2-ylcarbamate (1AJ)

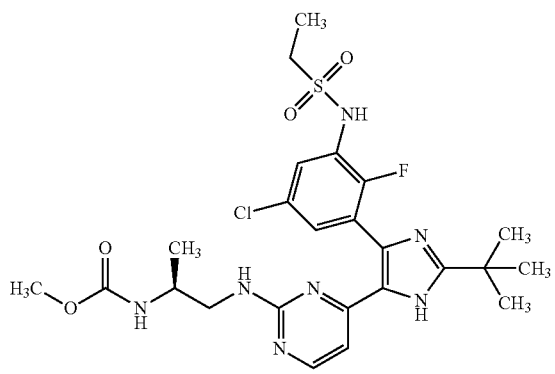

LCMS (m/z) (M+H)=568.2, Retention time (t$_R$)=0.70 minute.

N-(2-Chloro-3-(5-(2-(2-cyanopropylamino)pyrimidin-4-yl)-2-cyclopropyl-1H-imidazol-4-yl)phenyl)methanesulfonamide (1AK)

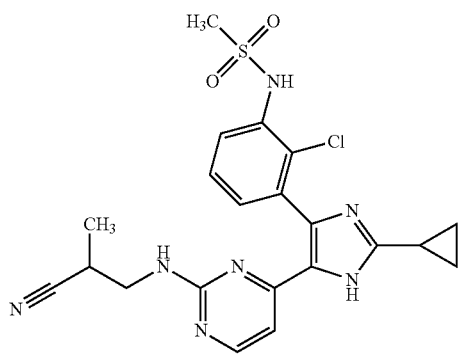

LCMS (m/z) (M+H)=472.1, Retention time (t$_R$)=0.51 minute.

(S)-Methyl 1-(4-(5-(5-chloro-2-fluoro-3-(methylsulfonamido)phenyl)-2-(1-methylcyclopropyl)-1H-imidazol-4-yl)pyrimidin-2-ylamino)propan-2-ylcarbamate (1AL)

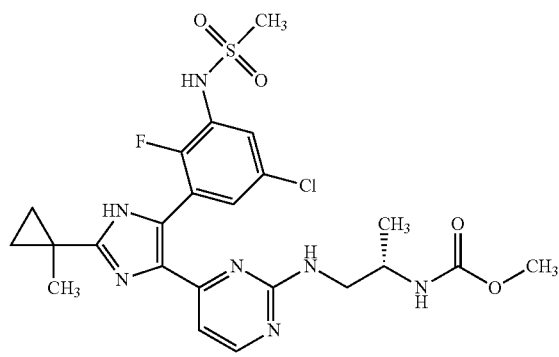

LCMS (m/z) (M+H)=552.2, Retention time (t$_R$)=0.65 minute.

(S)-Methyl 1-(4-(5-(2-fluoro-5-methyl-3-(methylsulfonamido)phenyl)-2-(1-methylcyclopropyl)-1H-imidazol-4-yl)pyrimidin-2-ylamino)propan-2-ylcarbamate (1AM)

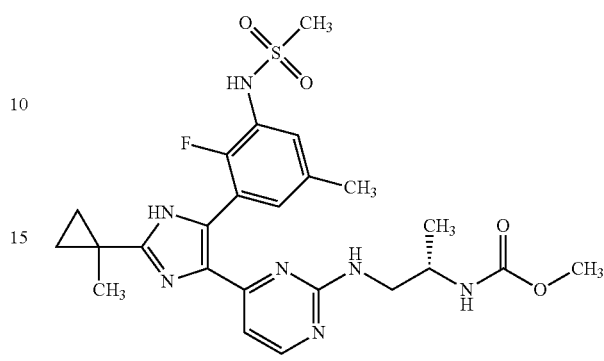

LCMS (m/z) (M+H)=532.2, Retention time (t$_R$)=0.60 minute.

N-(2-Chloro-3-(2-cyclopropyl-5-(2-(propylamino)pyrimidin-4-yl)-1H-imidazol-4-yl)-5-fluorophenyl)propane-1-sulfonamide (1AN)

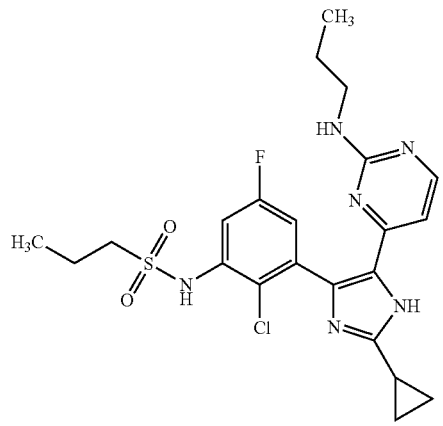

LCMS (m/z) (M+H)=493.0, Retention time (t$_R$)=0.70 minute.

(S)-Methyl 1-(4-(5-(2-chloro-3-(methylsulfonamido)phenyl)-2-(1-methylcyclopropyl)-1H-imidazol-4-yl)pyrimidin-2-ylamino)propan-2-ylcarbamate (1AO)

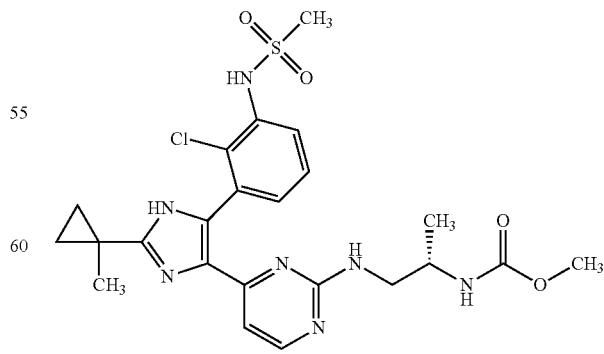

LCMS (m/z) (M+H)=534.2, Retention time (t$_R$)=0.57 minute.

N-(2-Chloro-3-(2-cyclopropyl-5-(2-(propylamino)pyrimidin-4-yl)-1H-imidazol-4-yl)-5-fluorophenyl)methanesulfonamide (1AP)

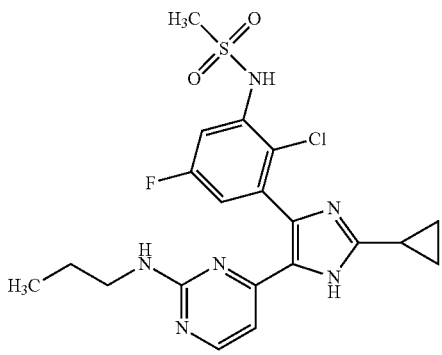

LCMS (m/z) (M+H)=465.0, Retention time ($t_R$)=0.59 minute.

N-(2-Chloro-3-(2-cyclopropyl-5-(2-(ethylamino)pyrimidin-4-yl)-1H-imidazol-4-yl)-5-fluorophenyl)methanesulfonamide (1AQ)

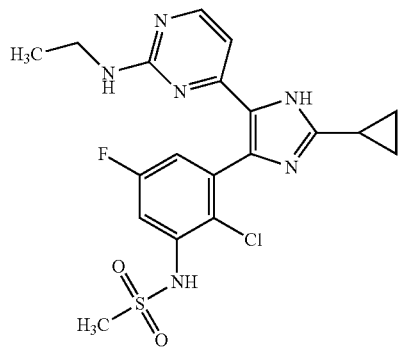

LCMS (m/z) (M+H)=451.0, Retention time ($t_R$)=0.53 minute.

N-(2-Chloro-3-(2-cyclopropyl-5-(2-(isobutylamino)pyrimidin-4-yl)-1H-imidazol-4-yl)-5-fluorophenyl)methanesulfonamide (1AR)

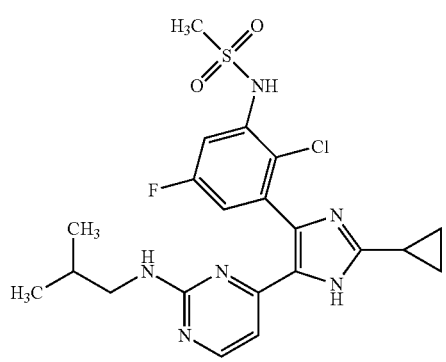

LCMS (m/z) (M+H)=479.1, Retention time ($t_R$)=0.63 minute.

N-(2-Chloro-3-(2-cyclopropyl-5-(2-(ethylamino)pyrimidin-4-yl)-1H-imidazol-4-yl)-5-fluorophenyl)propane-1-sulfonamide (1AS)

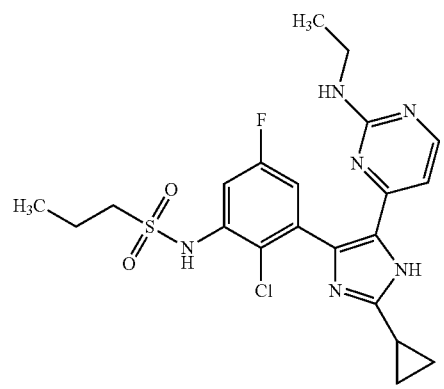

LCMS (m/z) (M+H)=479.1, Retention time ($t_R$)=0.63 minute.

N-(2-Chloro-3-(2-cyclopropyl-5-(2-(isopropylamino)pyrimidin-4-yl)-1H-imidazol-4-yl)-5-fluorophenyl)methanesulfonamide (1AT)

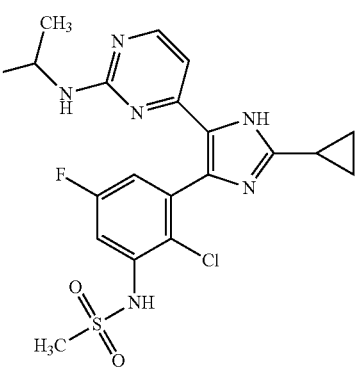

LCMS (m/z) (M+H)=465.1, Retention time ($t_R$)=0.57 minute.

N-(2-Chloro-3-(2-cyclopropyl-5-(2-(isopropylamino)pyrimidin-4-yl)-1H-imidazol-4-yl)-5-fluorophenyl)propane-1-sulfonamide (1AU)

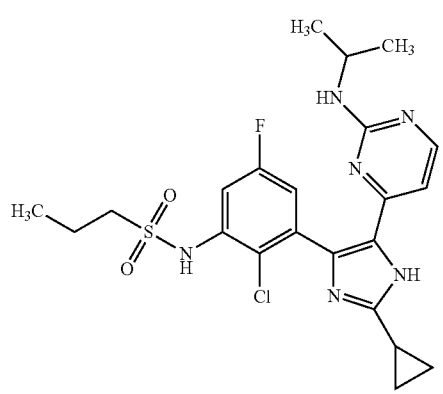

LCMS (m/z) (M+H)=493.1, Retention time ($t_R$)=0.67 minute.

77

(R)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate (1AV)

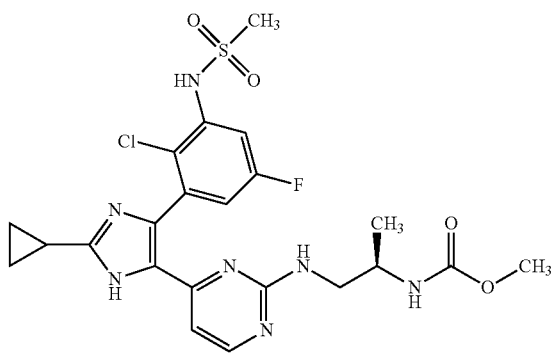

(1AV)

$^1$H NMR (400 MHz, CD$_3$CO$_2$D) δ 1.20 (d, J=6.3 Hz, 5H) 1.25-1.40 (m, 2H) 2.30-2.57 (m, 1H) 3.15 (s, 3H) 3.18-3.36 (m, 1H) 3.71 (s, 4H) 3.93-4.21 (m, 1H) 6.31-6.61 (m, 1H) 7.21 (dd, J=7.8, 2.7 Hz, 1H) 7.53-7.68 (m, 1H) 8.03-8.23 (m, 1H).

LCMS (m/z) (M+H)=538.1, Retention time (t$_R$)=0.57 minute.

(S)-Methyl 1-(4-(5-(5-chloro-2-fluoro-3-(4-fluorophenylsulfonamido)phenyl)-2-cyclopropyl-1H-imidazol-4-yl)pyrimidin-2-ylamino)propan-2-ylcarbamate (1AW)

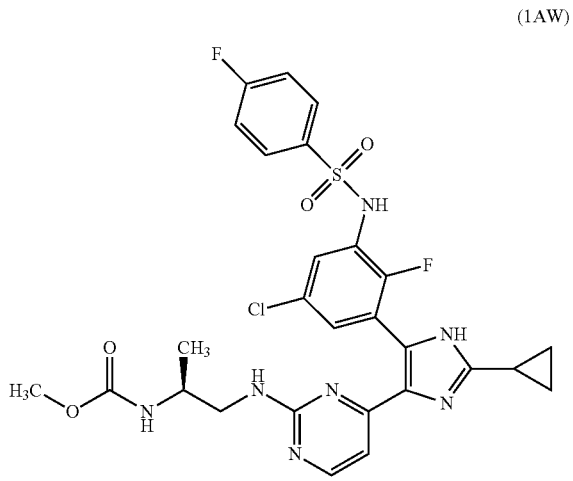 [SMILES: COC(=O)N[C@@H](C)CNc1nccc(-c2nc(C3CC3)[nH]c2-c2cc(Cl)cc(NS(=O)(=O)c3ccc(F)cc3)c2F)n1]

(1AW)

LCMS (m/z) (M+H)=618.2, Retention time (t$_R$)=0.76 minute.

78

(S)-Methyl 1-(4-(5-(5-chloro-2-fluoro-3-(3-fluorophenylsulfonamido)phenyl)-2-cyclopropyl-1H-imidazol-4-yl)pyrimidin-2-ylamino)propan-2-ylcarbamate (1AX)

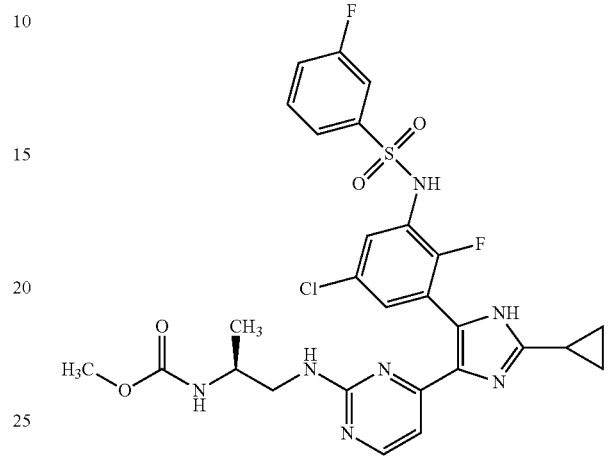

(1AX)

LCMS (m/z) (M+H)=618.2, Retention time (t$_R$)=0.75 minute.

N-(2-Chloro-3-(5-(2-(2-cyanoethylamino)pyrimidin-4-yl)-2-(1-methylcyclopropyl)-1H-imidazol-4-yl)-5-fluorophenyl)methanesulfonamide (1AY)

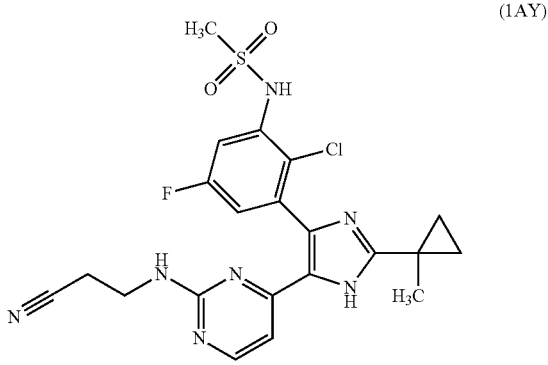 [SMILES: CC1(c2nc(-c3cc(F)cc(NS(C)(=O)=O)c3Cl)c(-c3ccnc(NCCC#N)n3)[nH]2)CC1]

(1AY)

$^1$H NMR (400 MHz, CDCl$_3$) δ 0.87-0.94 (m, 2H) 1.26-1.34 (m, 2H) 1.60 (s, 3H) 2.73 (t, J=6.1 Hz, 2H) 3.07 (s, 3H) 3.79 (t, J=6.1 Hz, 2H) 5.59 (br s, 1H) 6.13 (d, J=5.5 Hz, 1H) 7.05 (m, 1H) 7.53 (m, 1H) 8.06 (d, J=5.5 Hz, 1H) 10.05 (br s, 1H). LCMS (m/z) (M+H)=490.0, Retention time (t$_R$)=0.55 minute.

methylcyclopropyl)-1H-imidazol-4-yl)-5-methylphenyl)methanesulfonamide (1AZ)

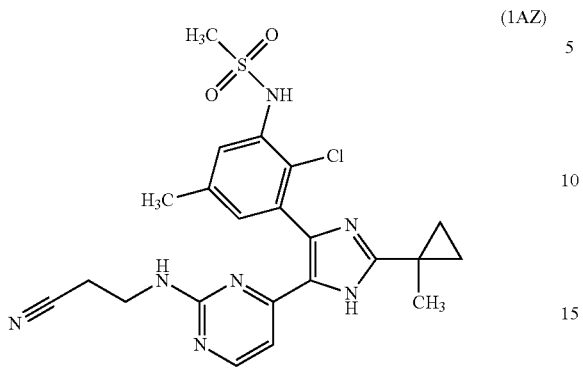

(1AZ)

¹H NMR (400 MHz, CDCl₃) δ 0.85-0.94 (m, 2H) 1.26-1.35 (m, 2H) 1.60 (s, 3H) 1.63 (br s, 1H) 2.38 (s, 3H) 2.73 (t, J=5.9 Hz, 2H) 3.02 (s, 3H) 3.78 (d, J=5.9 Hz, 2H) 5.65 (br s, 1H) 6.11 (d, J=5.5 Hz, 1H) 7.14 (s, 1H) 7.55 (s, 1H) 8.01 (d, J=5.1 Hz, 1H) 10.02 (br s, 1H). LCMS (m/z) (M+H)=486.1, Retention time (t$_R$)=0.55 minute.

N-(3-(5-(2-(2-Cyanoethylamino)pyrimidin-4-yl)-2-(1-methylcyclopropyl)-1H-imidazol-4-yl)-2-fluoro-5-methylphenyl)methanesulfonamide (1BA):

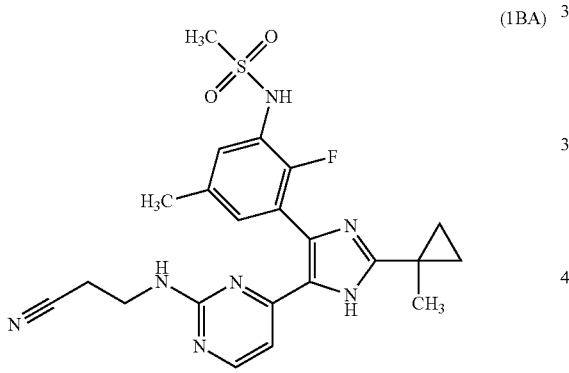

(1BA)

LCMS (m/z) (M+H)=470.1, Retention time (t$_R$)=0.55 minute.

N-(5-Chloro-3-(5-(2-(2-cyanoethylamino)pyrimidin-4-yl)-2-(1-methylcyclopropyl)-1H-imidazol-4-yl)-2-fluorophenyl)methanesulfonamide (1BB)

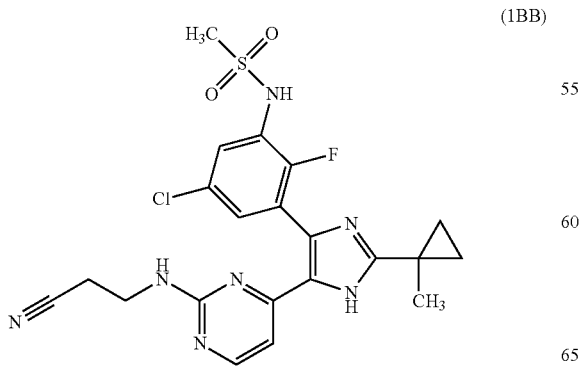

(1BB)

LCMS (m/z) (M+H)=490.2, Retention time (t$_R$)=0.62 minute.

N-(2-Chloro-3-(5-(2-(2-cyanoethylamino)pyrimidin-4-yl)-2-(1-methylcyclopropyl)-1H-imidazol-4-yl)phenyl)methanesulfonamide (1BC)

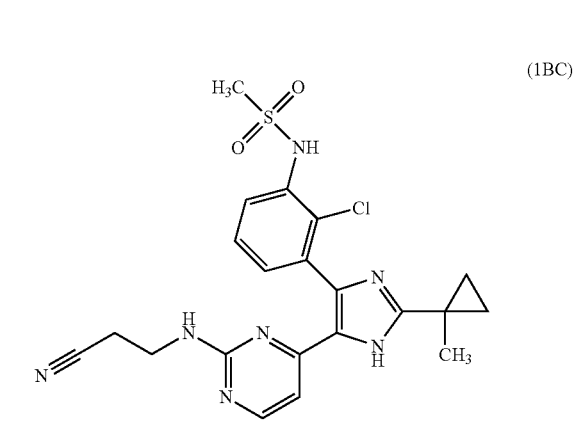 [SMILES: CC1(c2nc(-c3cccc(NS(C)(=O)=O)c3Cl)c(-c3ccnc(NCCC#N)n3)[nH]2)CC1]

(1BC)

¹H NMR (400 MHz, CDCl₃) δ 0.81-1.01 (m, 2H) 1.28-1.39 (m, 2H) 1.61 (s, 3H) 2.11-2.44 (m, 1H) 2.70 (br s, 2H) 3.05 (s, 3H) 3.75 (br s, 2H) 5.83 (br s, 1H) 6.14 (br s, 1H) 7.31 (d, J=7.4 Hz, 1H) 7.40 (m, 1H) 7.74 (d, J=7.8 Hz, 1H) 8.02 (d, J=3.9 Hz, 1H) 9.82-10.39 (br s, 1H). LCMS (m/z) (M+H)=472.2, Retention time (t$_R$)=0.53 minute.

N-(3-(5-(2-Aminopyrimidin-4-yl)-2-tert-butyl-1H-imidazol-4-yl)-5-chloro-2-fluorophenyl)methanesulfonamide (1BD)

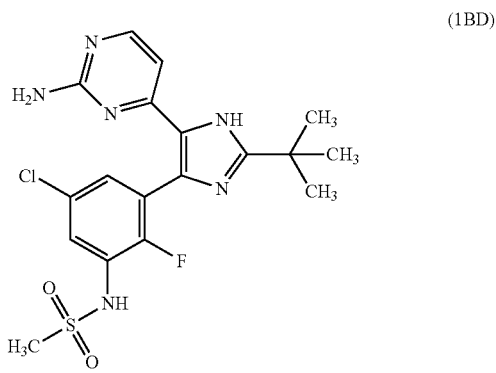 [SMILES: CC(C)(C)c1nc(-c2cc(Cl)cc(NS(C)(=O)=O)c2F)c(-c2ccnc(N)n2)[nH]1]

(1BD)

¹H NMR (400 MHz, CDCl₃) δ 1.50 (s, 9H) 3.15 (s, 3H) 6.66-6.81 (m, 1H) 7.35-7.42 (m, 1H) 7.60-7.69 (m, 1H) 7.93-8.02 (m, 1H). LCMS (m/z) (M+H)=439.0, Retention time (t$_R$)=0.57 minute.

N-(3-(5-(2-Aminopyrimidin-4-yl)-2-tert-butyl-1H-imidazol-4-yl)-5-chloro-2-fluorophenyl)-2,6-difluorobenzenesulfonamide (1BE)

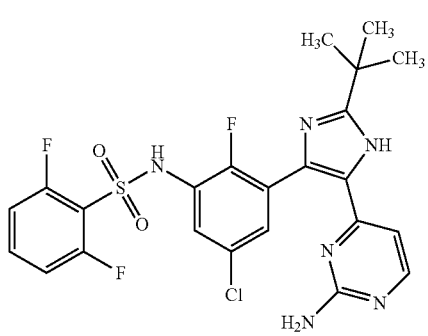

1H NMR (400 MHz, CDCl₃) δ 1.50 (s, 9H) 6.56-6.66 (m, 1H) 7.06 (m, 2H) 7.31-7.37 (m, 1H) 7.38-7.48 (m, 1H) 7.50-7.62 (m, 1H) 7.63-7.68 (m, 1H) 7.90-7.96 (m, 1H).
LCMS (m/z) (M+H)=537.1, Retention time (t_R)=0.70 minute.

N-(3-(5-(2-Aminopyrimidin-4-yl)-2-cyclopropyl-1H-imidazol-4-yl)-5-chloro-2-fluorophenyl)-2,6-difluorobenzenesulfonamide (1BF)

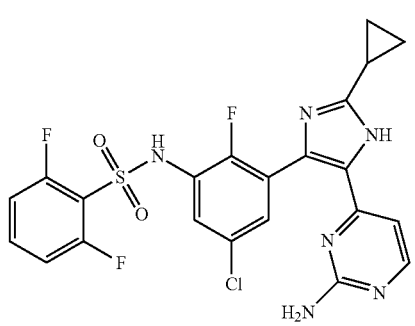

¹H NMR (400 MHz, CD₃CO₂D) δ 1.05-1.20 (m, 4H), 2.16-2.28 (m, 1H) 6.61-6.70 (m, 1H) 6.91-7.04 (m, 2H) 7.28-7.36 (m, 1H) 7.44-7.54 (m, 1H) 7.54-7.62 (m, 1H) 8.08-8.20 (m, 1H). LCMS (m/z) (M+H)=521.1, Retention time (t_R)=0.65 minute.

N-(3-(5-(2-Aminopyrimidin-4-yl)-2-cyclopropyl-1H-imidazol-4-yl)-5-chloro-2-fluorophenyl)methanesulfonamide (1BG)

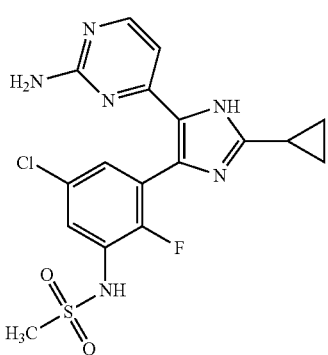

¹H NMR (400 MHz, CD₃CO₂D) δ 1.20-1.38 (m, 4H) 2.32-2.44 (m, 1H) 3.14 (s, 3H) 6.90-6.99 (m, 1H) 7.42-7.52 (m, 1H) 7.67-7.77 (m, 1H) 8.25-8.36 (m, 1H). LCMS (m/z) (M+H)=423.1, Retention time (t_R)=0.51 minute.

N-(3-(5-(2-Aminopyrimidin-4-yl)-2-tert-butyl-1H-imidazol-4-yl)-5-chloro-2-fluorophenyl)propane-1-sulfonamide (1BH)

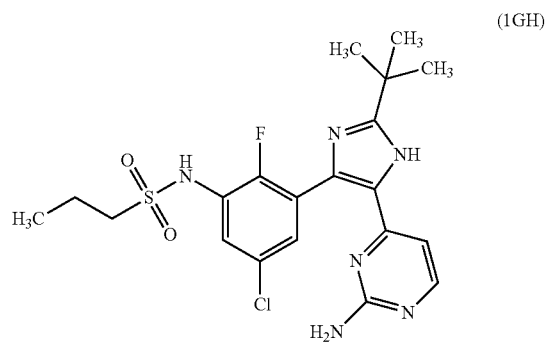 [SMILES: CCCS(=O)(=O)Nc1cc(Cl)cc(-c2nc(C(C)(C)C)[nH]c2-c2ccnc(N)n2)c1F]

¹H NMR (400 MHz, CD₃CO₂D) δ 0.96-1.08 (m, 3H) 1.55 (s, 9H) 1.78-1.92 (m, 2H) 3.16-3.27 (m, 2H) 6.99-7.07 (m, 1H) 7.44-7.52 (m, 1H) 7.70-7.79 (m, 1H) 8.30-8.40 (m, 1H). LCMS (m/z) (M+H)=467.1, Retention time (t_R)=0.65 minute.

(S)-Methyl 1-(4-(4-(2-chloro-3-(2,6-difluorophenylsulfonamido)-5-fluorophenyl)-2-cyclopropyl-1H-imidazol-5-yl)pyrimidin-2-ylamino)propan-2-ylcarbamate (1BI)

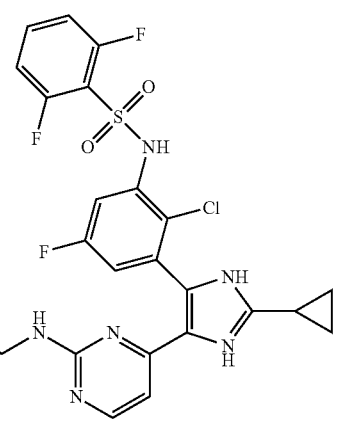

¹H NMR (400 MHz, CD₃CO₂D) δ 1.19 (d, J=7.0 Hz, 3H) 1.22-1.28 (m, 2H) 1.33 (br s, 2H) 2.41-2.57 (m, 1H) 3.16 (m, 1H) 3.70 (s, 3H) 3.76 (m, 1H) 3.99-4.18 (m, 1H) 6.26 (d, J=6.3 Hz, 1H) 7.12 (m, 2H) 7.22 (dd, J=7.8, 2.4 Hz, 1H) 7.56-7.76 (m, 2H) 8.15 (d, J=6.3 Hz, 1H). LCMS (m/z) (M+H)=636.1, Retention time (t_R)=0.72 minute.

N-(3-(5-(2-Aminopyrimidin-4-yl)-2-tert-butyl-1H-imidazol-4-yl)-2-chloro-5-fluorophenyl)methanesulfonamide (1BJ)

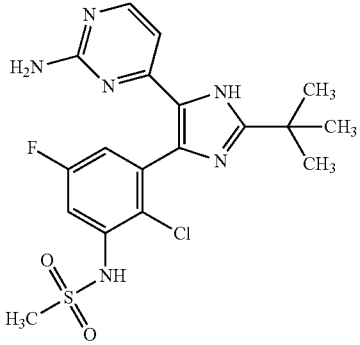

$^1$H NMR (400 MHz, CD$_3$CO$_2$D) δ 1.56 (s, 9H) 3.14 (s, 3H) 6.75-6.85 (m, 1H) 7.24-7.33 (m, 1H) 7.57-7.68 (m, 1H) 8.22-8.32 (m, 1H). LCMS (m/z) (M+H)=439.0, Retention time (t$_R$)=0.50 minute.

N-(3-(5-(2-Aminopyrimidin-4-yl)-2-tert-butyl-1H-imidazol-4-yl)-2-chlorophenyl)-2,6-difluorobenzenesulfonamide (1BK)

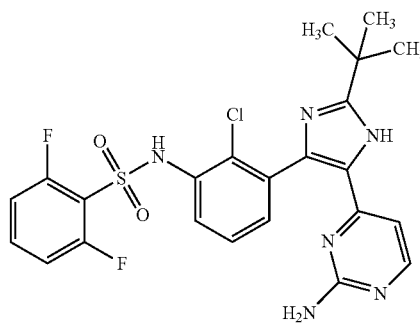

$^1$H NMR (400 MHz, CD$_3$CO$_2$D) δ1.54 (s, 9H) 6.35-6.46 (m, 1H) 7.03-7.14 (m, 2H) 7.48 (s, 2H) 7.56-7.69 (m, 1H) 7.78-7.88 (m, 1H) 8.11-8.22 (m, 1H). LCMS (m/z) (M+H)=519.0, Retention time (t$_R$)=0.59 minute.

N-(3-(5-(2-Aminopyrimidin-4-yl)-2-tert-butyl-1H-imidazol-4-yl)-2-chlorophenyl)methanesulfonamide (1BL)

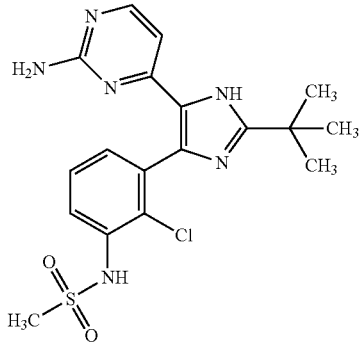

$^1$H NMR (400 MHz, CD$_3$CO$_2$D) δ 1.57 (s, 9H) 3.10 (s, 3H) 6.58-6.69 (m, 1H) 7.45-7.57 (m, 2H) 7.76-7.89 (m, 1H) 8.16-8.27 (m, 1H). LCMS (m/z) (M+H)=421.0, Retention time (t$_R$)=0.43 minute.

(S)-Methyl 1-(4-(4-(5-chloro-3-(3,5-difluorophenylsulfonamido)-2-fluorophenyl)-2-cyclopropyl-1H-imidazol-5-yl)pyrimidin-2-ylamino)propan-2-ylcarbamate (1BM)

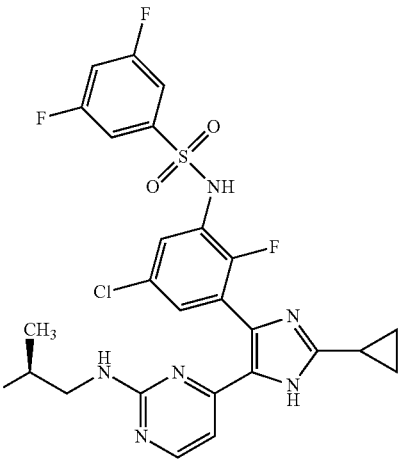

LCMS (m/z) (M+H)=636.2, Retention time (t$_R$)=0.81 minute.

(S)-Methyl 1-(4-(4-(5-chloro-2-fluoro-3-(4-(trifluoromethyl)phenylsulfonamido)phenyl)-2-cyclopropyl-1H-imidazol-5-yl)pyrimidin-2-ylamino)propan-2-ylcarbamate (1BN)

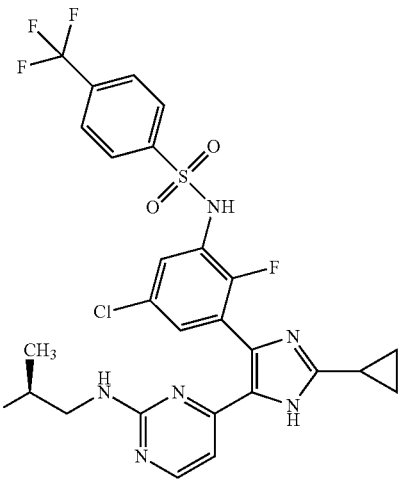

LCMS (m/z) (M+H)=668.2, Retention time (t$_R$)=0.85 minute.

(S)-Methyl 1-(4-(2-cyclopropyl-4-(2-fluoro-5-methyl-3-(2,2,2-trifluoroethylsulfonamido)phenyl)-1H-imidazol-5-yl)pyrimidin-2-ylamino)propan-2-ylcarbamate (1BO)

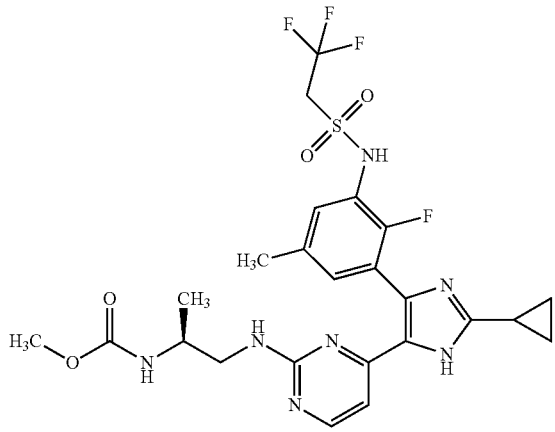

(1BO)

$^1$H NMR (400 MHz, CD$_3$CO$_2$D) δ 0.99-1.57 (m, 7H) 2.26-2.64 (m, 4H) 3.03-3.29 (m, 1H) 3.56-3.90 (m, 4H) 4.07 (br s, 1H) 4.20 (m, 2H) 6.61 (m, 1H) 7.34 (d, J=3.9 Hz, 1H) 7.53 (d, J=5.5 Hz, 1H) 8.15 (d, J=5.9 Hz, 1H). LCMS (m/z) (M+H)=586.2, Retention time (t$_R$)=0.67 minute.

N-(3-(5-(2-Aminopyrimidin-4-yl)-2-tert-butyl-1H-imidazol-4-yl)-2-chloro-5-fluorophenyl)-2,6-difluorobenzenesulfonamide (1BP)

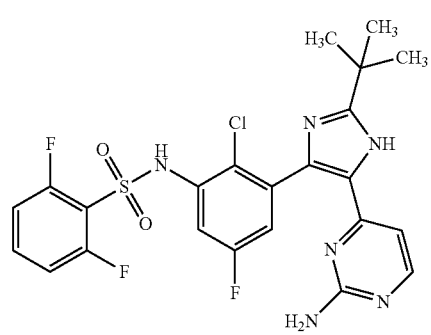

(1BP)

$^1$H NMR (400 MHz, CD$_3$CO$_2$D) δ 1.52 (s, 9H) 6.52-6.59 (m, 1H) 7.07-7.16 (m, 2H) 7.22-7.29 (m, 1H) 7.59-7.70 (m, 2H) 8.20 (d, J=6.3 Hz, 1H). LCMS (m/z) (M+H)=537.0, Retention time (t$_R$)=0.65 minute.

N-(3-(5-(2-Aminopyrimidin-4-yl)-2-cyclopropyl-1H-imidazol-4-yl)-2-chloro-5-fluorophenyl)methanesulfonamide (1BQ)

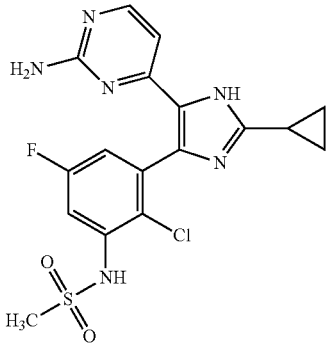

(1BQ)

$^1$H NMR (400 MHz, CD$_3$CO$_2$D) δ 1.22-1.41 (m, 4H) 2.34-2.47 (m, 1H) 3.14 (s, 3H) 6.64-6.74 (m, 1H) 7.22-7.31 (m, 1H) 7.57-7.70 (m, 1H) 8.22-8.34 (m, 1H). LCMS (m/z) (M+H)=423.0, Retention time (t$_R$)=0.43 minute.

N-(3-(5-(2-Aminopyrimidin-4-yl)-2-cyclopropyl-1H-imidazol-4-yl)-2-chloro-5-fluorophenyl)-2,6-difluorobenzenesulfonamide (1BR)

(1BR)

$^1$H NMR (400 MHz, CD$_3$CO$_2$D) δ 1.05-1.22 (m, 4H) 2.16-2.30 (m, 1H) 6.27-6.38 (m, 1H) 6.92-7.03 (m, 2H) 7.05-7.14 (m, 1H) 7.45-7.57 (m, 2H) 8.02-8.13 (m, 1H). LCMS (m/z) (M+H)=521.1, Retention time (t$_R$)=0.59 minute.

N-(3-(5-(2-Aminopyrimidin-4-yl)-2-cyclopropyl-1H-imidazol-4-yl)-2-chloro-5-fluorophenyl)propane-1-sulfonamide (1BS)

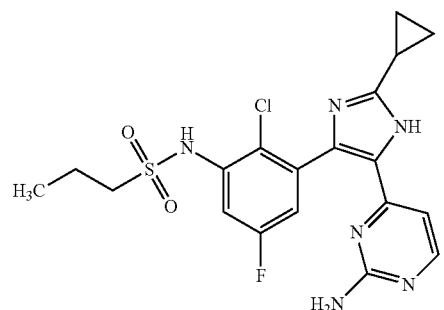

(1BS)

$^1$H NMR (400 MHz, CD$_3$CO$_2$D) δ 1.02 (s, 3H) 1.21-1.40 (m, 4H) 1.77-1.93 (m, 2H) 2.32-2.48 (m, 1H) 3.17-3.29 (m, 2H) 6.62-6.71 (m, 1H) 7.17-7.28 (m, 1H) 7.61-7.73 (m, 1H) 8.21-8.31 (m, 1H). LCMS (m/z) (M+H)=451.0, Retention time (t$_R$)=0.56 minute.

(S)-Methyl 1-(4-(4-(5-chloro-2-fluoro-3-(methylsulfonamido)phenyl)-2-cyclobutyl-1H-imidazol-5-yl)pyrimidin-2-ylamino)propan-2-ylcarbamate (1BT)

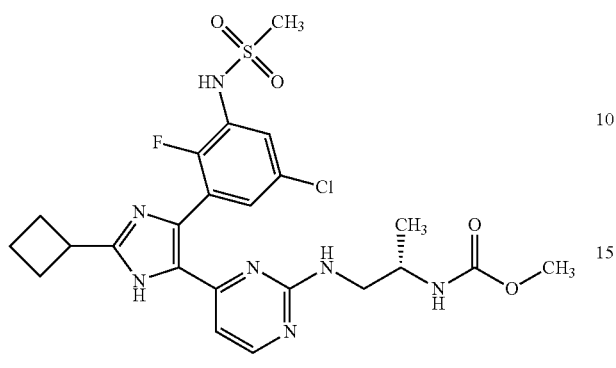
(1BT)

LCMS (m/z) (M+H)=552.3, Retention time (t$_R$)=0.66 minute.

(S)-Methyl 1-(4-(4-(2-chloro-5-fluoro-3-(methylsulfonamido)phenyl)-2-cyclobutyl-1H-imidazol-5-yl)pyrimidin-2-ylamino)propan-2-ylcarbamate (1BU):

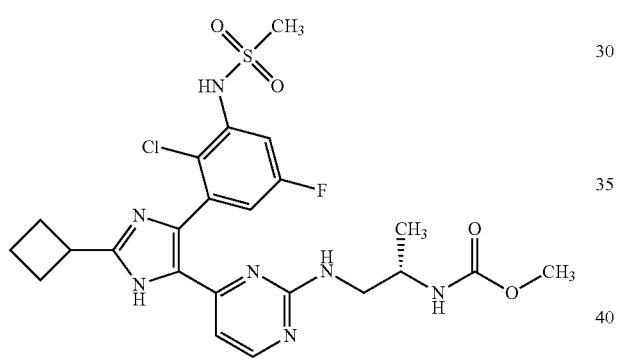
(1BU)

LCMS (m/z) (M+H)=552.2, Retention time (t$_R$)=0.63 minute.

N-(2-Chloro-3-(2-cyclopropyl-5-(2-(methylamino)pyrimidin-4-yl)-1H-imidazol-4-yl)-5-fluorophenyl)-2,6-difluorobenzenesulfonamide (1BV):

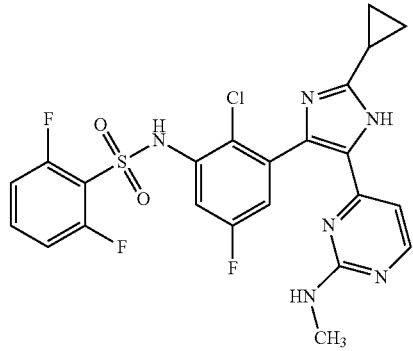
(1BV)

$^1$H NMR (300 MHz, CD$_3$CO$_2$D) δ 1.07-1.09 (m, 4H) 2.17-2.21 (m, 1H) 2.49 (s, 3H) 6.64 (m, 1H) 6.96-7.08 (m, 3H) 7.47-7.55 (m, 2H) 8.08-8.11 (d, 1H). LCMS (m/z) (M+H)=535.1, Retention time (t$_R$)=0.64 minute.

N-(2-Chloro-3-(2-cyclopropyl-5-(2-(methylamino)pyrimidin-4-yl)-1H-imidazol-4-yl)-5-fluorophenyl)methanesulfonamide (1BW)

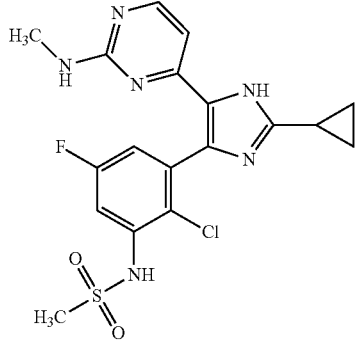
(1BW)

$^1$H NMR (300 MHz, CD$_3$CO$_2$D) δ 1.31 (br. s., 4H) 2.30-2.50 (m, 1H) 2.80 (br s, 3H) 3.15 (s, 3H) 6.84-6.98 (m, 1H) 7.20-7.35 (m, 1H) 7.63 (m, 1H) 8.32 (br s, 1H). LCMS (m/z) (M+H)=437.1, Retention time (t$_R$)=0.49 minute.

N-(2-Chloro-3-(2-cyclopropyl-5-(2-(methylamino)pyrimidin-4-yl)-1H-imidazol-4-yl)-5-fluorophenyl)propane-1-sulfonamide (1BX)

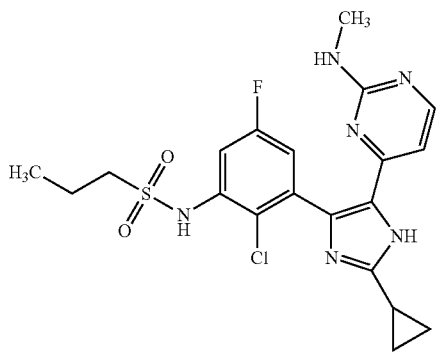
(1BX)

$^1$H NMR (400 MHz, CD$_3$CO$_2$D) δ1.02 (t, J=7.4 Hz, 3H) 1.20 (br s, 4H) 1.78-1.93 (m, 2H) 2.23-2.39 (m, 1H) 2.75 (s, 3H) 3.15-3.29 (m, 2H) 6.72-6.86 (m, 1H) 7.12-7.25 (m, 1H) 7.54-7.67 (m, 1H) 8.17-8.28 (m, 1H). LCMS (m/z) (M+H)=465.2, Retention time (t$_R$)=0.58 minute.

(S)-Methyl 1-(4-(4-(2-chloro-5-fluoro-3-(methylsulfonamido)phenyl)-2-(2,4-difluorophenyl)-1H-imidazol-5-yl)pyrimidin-2-ylamino)propan-2-ylcarbamate (1BY)

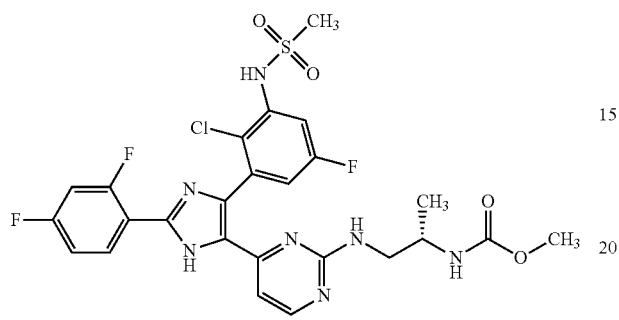

(1BY)

LCMS (m/z) (M+H)=610.0, Retention time ($t_R$)=0.62 minute.

(S)-Methyl 1-(4-(4-(2-chloro-5-fluoro-3-(methylsulfonamido)phenyl)-2-(4-(trifluoromethyl)phenyl)-1H-imidazol-5-yl)pyrimidin-2-ylamino)propan-2-ylcarbamate (1BZ)

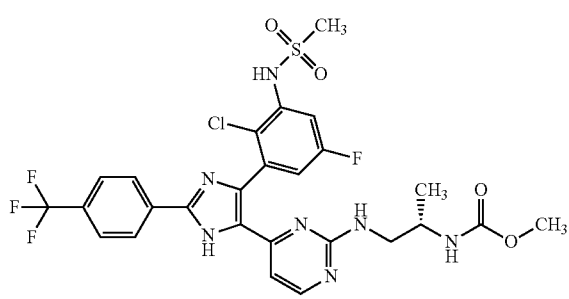

(1BZ)

LCMS (m/z) (M+H)=642.1, Retention time ($t_R$)=0.82 minute.

Example 2

Preparation of N-(5-chloro-3-(5-(2-(2-cyanoethylamino)pyrimidin-4-O-2-cyclopropyl-1H-imidazol-4-yl)-2-fluorophenyl)methanesulfonamide, free base and hydrogen chloride salt (2A-1 and 2A-2)

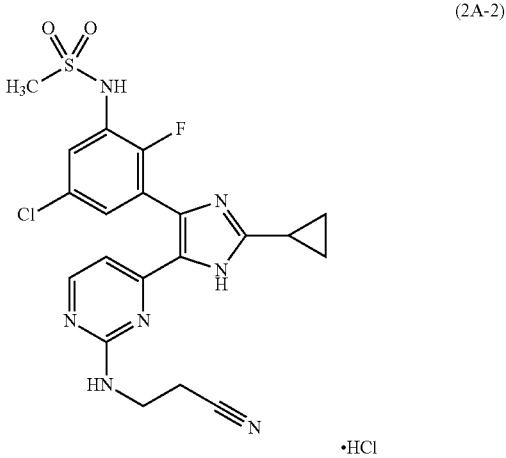 [SMILES: CS(=O)(=O)Nc1cc(Cl)cc(-c2nc(C3CC3)[nH]c2-c2ccnc(NCCC#N)n2)c1F ; Cl]

(2A-2)

Two separate reaction vials were each charged with 3-(4-(4-bromo-2-cyclopropyl-1-((2-(trimethylsilyl)ethoxy)methyl)-1H-imidazol-5-yl)pyrimidin-2-ylamino)propanenitrile (I-1c, ~200 mg, 0.43 mmol), a solution of 5-chloro-2-fluoro-3-(4,4,5,5-tetramethyl-1,3,2-dioxaborolan-2-yl)aniline (0.2 M in dioxane, 8 mL, 1.6 mmol), DME (8 mL) and aqueous 2.0 M $Na_2CO_3$ solution (2.3 mL, 4.6 mmol). The resulting mixture was sparged with Argon and Pd(PPh$_3$)$_4$ was added. The reaction vials were sealed and irradiated at 120° C. for 20 minutes in a microwave reactor. LCMS indicated near complete conversion. Additional 5-chloro-2-fluoro-3-(4,4,5,5-tetramethyl-1,3,2-dioxaborolan-2-yl)aniline (0.2 M in dioxane, 8 mL, 1.6 mmol) was added and the reaction was irradiated at 120° C. for 7 minutes. The reactions were allowed to cool to room temperature which partitioned upon standing. The layers were separated and the organic portions of the two reactions were combined and concentrated. The resulting residue was partitioned between EtOAc (200 mL) and water (20 mL). The layers were separated and the organic portion was washed with aqueous 0.1 N HCl solution (40 mL), brine, dried ($Na_2SO_4$), and concentrated to give 3-(4-(4-(3-amino-5-chloro-2-fluorophenyl)-2-cyclopropyl-1-((2-(trimethylsilyl)ethoxy)methyl)-1H-imidazol-5-yl)pyrimidin-2-ylamino)propanenitrile as a crude residue which was carried forward without further purification: LCMS (m/z) 528.2 (MH$^+$), $t_R$=0.90 minute.

To a solution of 3-(4-(4-(3-amino-5-chloro-2-fluorophenyl)-2-cyclopropyl-1-((2-(trimethylsilyl)ethoxy)methyl)-1H-imidazol-5-yl)pyrimidin-2-ylamino)propanenitrile (0.58 g, 1.1 mmol) in EtOH (10 mL) was added concentrated HCl (1 mL). The resulting reaction was maintained at room temperature for 9 hours after which the reaction mixture was concentrated and partitioned between water (60 mL) and EtOAc (250 mL). The layers were separated and the aqueous portion was neutralized with solid NaHCO$_3$, and then extracted with EtOAc (200, 100 mL). The combined organic portions were then extracted with 0.1 M aqueous HCl solution (2×100 mL). The combined acidic aqueous extracts were neutralized with solid NaHCO$_3$ and extracted with EtOAc (2×100 mL). The combined organic phases were washed with brine, dried (Na$_2$SO$_4$), and then concentrated to furnish 3-(4-(4-(3-amino-5-chloro-2-fluorophenyl)-2-cyclopropyl-1H-imidazol-5-yl)pyrimidin-2-ylamino)propanenitrile (328 mg) as an amber residue which was carried forward without further purification: LCMS (m/z) 398.1 (MH$^+$), t$_R$=0.55 minute.

To an ice-bath cooled solution of 3-(4-(4-(3-amino-5-chloro-2-fluorophenyl)-2-cyclopropyl-1H-imidazol-5-yl)pyrimidin-2-ylamino)propanenitrile (328 mg, 0.82 mmol) in dry pyridine (1 mL) was slowly added methanesulfonyl chloride 100 µL, 1.3 mmol). After 6 hours allowing the cooling bath to expire, the reaction was partitioned between EtOAc (60 mL) and water (30 mL). The layers were separated and the aqueous phase was extracted with EtOAc (40 mL). The combined organic phases were washed with brine, dried (Na$_2$SO$_4$) and concentrated to give 430 mg of a reddish-brown residue which was purified by reverse phase HPLC. The combined product fractions were concentrated in vacuo and the remaining aqueous solution was neutralized with aqueous 2.0 M NaOH solution and extracted with EtOAc (3×75 mL). The combined organic phases were then concentrated and dissolved in DCM (150 mL) and extracted with aqueous 0.1 M NaOH solution (2×125 mL). The combined aqueous extracts were neutralized with aqueous 1.0 M HCl solution and then extracted with DCM (3×75 mL). The combined organic extracts were washed with brine, dried (Na$_2$SO$_4$), and concentrated. The resulting free base (2A-1) was converted to the corresponding hydrogen chloride salt by dissolving in acetonitrile-water (7 mL) containing 1 equivalent of HCl and lyophilized to yield 134 mg of the titled compound as the hydrochloride salt (2A-2): LCMS (m/z) 476.1 (MH$^+$), retention time t$_R$=0.57 minute; $^1$H NMR (400 MHz, CD$_3$CO$_2$D) δ 8.34 (d, J=5.9 Hz, 1H), 7.64-7.90 (m, 1H), 7.31-7.59 (m, 1H), 7.12 (d, J=4.3 Hz, 1H), 3.66 (t, J=6.1 Hz, 2H), 3.18 (s, 3H), 2.65 (d, J=5.5 Hz, 2H), 2.50 (dd, J=8.2, 3.9 Hz, 1H), 1.04-1.68 (m, 5H).

The compounds listed below were prepared using procedures analogous to those described above for the preparation of Example 2A using the appropriate starting materials and isolated as either their free base or salt form (generally, the trifluoroacetate or hydrogen chloride salt).

(S)-Methyl 1-(4-(2-tert-butyl-4-(3-(cyclopropanesulfonamido)-2-fluorophenyl)-1H-imidazol-5-yl)pyrimidin-2-ylamino)propan-2-ylcarbamate (2B)

(2B)

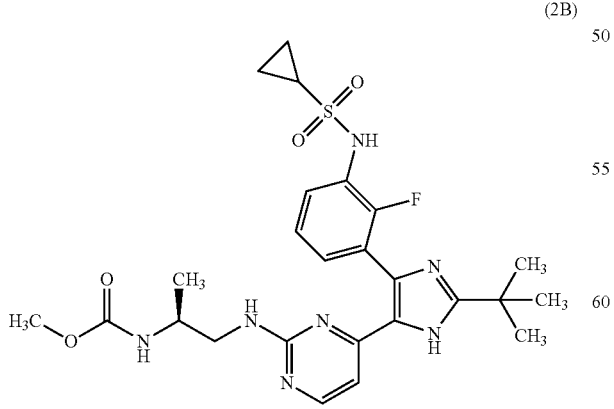

LCMS (m/z) (M+H)=546.2, Retention time (t$_R$)=0.6 minute.

(S)-Methyl 1-(4-(2-tert-butyl-4-(2-fluoro-3-(methylsulfonamido)phenyl)-1H-imidazol-5-yl)pyrimidin-2-ylamino)propan-2-ylcarbamate (2C)

(2C)

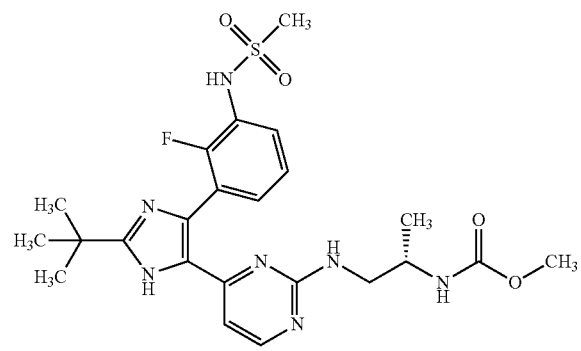

LCMS (m/z) (M+H)=520.1, Retention time (t$_R$)=0.55 minute.

(S)-Methyl 1-(4-(2-tert-butyl-4-(2-fluoro-3-(1-methylethylsulfonamido)phenyl)-1H-imidazol-5-yl)pyrimidin-2-ylamino)propan-2-ylcarbamate (2D)

(2D)

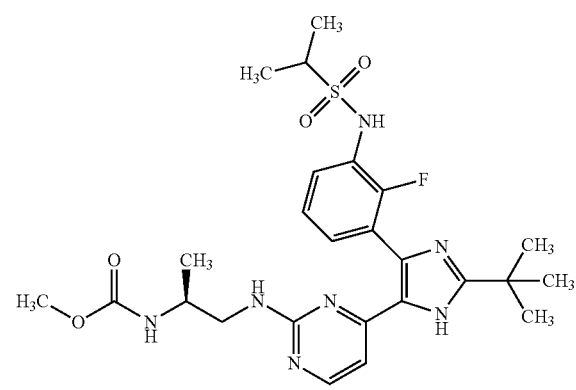

LCMS (m/z) (M+H)=548.2, Retention time (t$_R$)=0.62 minute.

N-(3-(5-(2-(2-Cyanoethylamino)pyrimidin-4-yl)-2-cyclopropyl-1H-imidazol-4-yl)-2-fluorophenyl)methanesulfonamide (2E)

(2E)

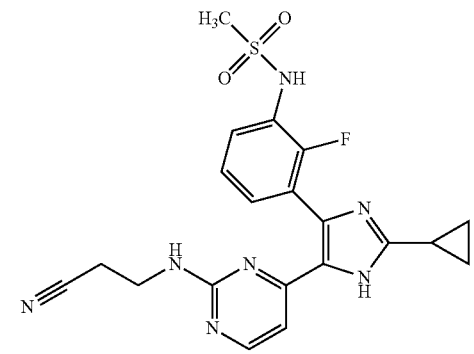

$^1$H NMR (300 MHz, CD$_3$CO$_2$D) δ 1.10-1.36 (m, 4H) 2.26-2.38 (m, 1H) 2.58 (t, J=6.3 Hz, 2H) 3.12 (d, J=2.1 Hz, 3H) 3.58 (t, J=5.9 Hz, 2H) 6.92 (d, J=5.3 Hz, 1H) 7.35 (t, J=8.8 Hz, 1H) 7.45 (app t, J=6.9 Hz, 1H) 7.71 (app t, J=7.8 Hz, 1H) 8.26 (dd, J=5.9, 2.1 Hz, 1H). LCMS (m/z) (M+H)=442.1, Retention time (t$_R$)=0.47 minute.

Methyl (2S) 1 (4 (4 (2 chloro-6-fluoro-3-(methylsulfonamido)phenyl)-2-cyclopropyl-1H-imidazol-5-yl)pyrimidin-2-ylamino)propan-2-ylcarbamate (2F)

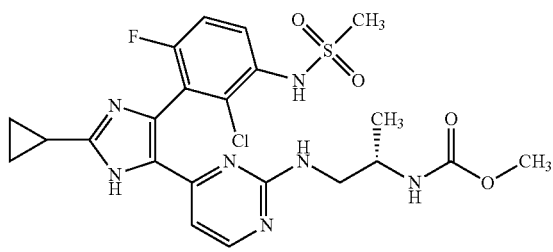

(2F)

LCMS (m/z) (M+H)=538.1, Retention time (t$_R$)=0.57 minute.

N-(2-Chloro-3-(5-(2-((1-cyanocyclopropyl)methylamino)pyrimidin-4-yl)-2-cyclopropyl-1H-imidazol-4-yl)phenyl)methanesulfonamide (2G)

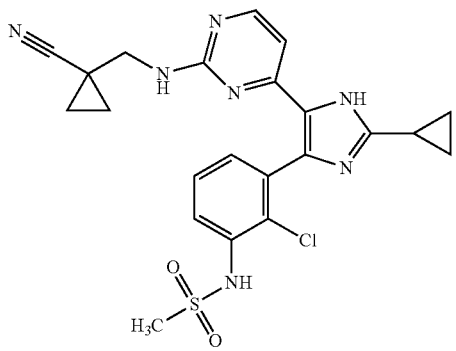

(2G)

$^1$H NMR (300 MHz, CD$_3$OOD) δ 0.98-1.09 (m, 2H) 1.15-1.30 (m, 6H) 2.29-2.42 (m, 1H) 3.10 (s, 3H) 3.40 (s, 2H) 6.79 (d, J=5.9 Hz, 1H) 7.47-7.58 (m, 2H) 7.81 (dd, J=7.8, 1.9 Hz, 1H) 8.22 (d, J=6.2 Hz, 1H). LCMS (m/z) (M+H)=484.1, Retention time (t$_R$)=0.52 minute.

N-(3-(5-(2-aminopyrimidin-4-yl)-2-cyclopropyl-1H-imidazol-4-yl)-2-chlorophenyl)-2,6-difluorobenzenesulfonamide (2H)

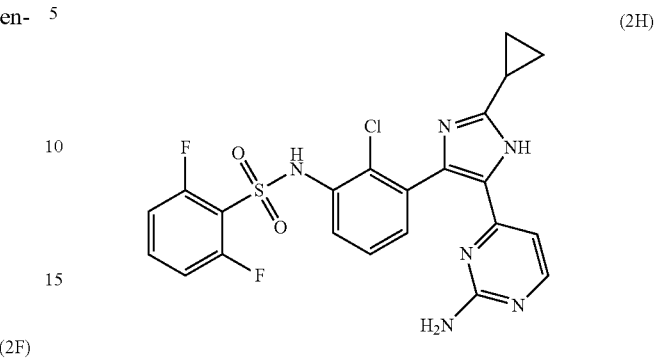

(2H)

LCMS (m/z) (M+H)=503.1, Retention time (t$_R$)=0.57 minute.

N-(2-Chloro-3-(2-cyclopropyl-5-(pyrimidin-4-yl)-1H-imidazol-4-yl)-5-fluorophenyl)-2,6-difluorobenzenesulfonamide (2I)

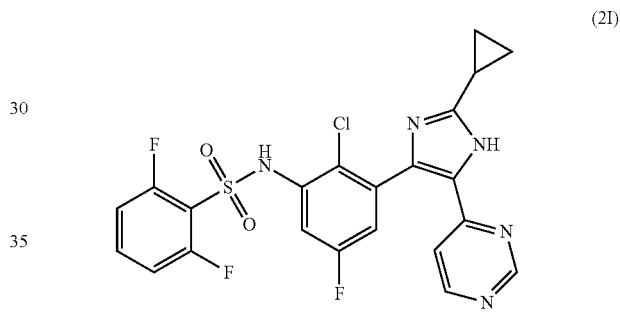

(2I)

$^1$H NMR (300 MHz, CD$_3$CO$_2$D) δ 1.28-1.33 (m, 4H) 2.28-2.42 (m, 1H) 7.08-7.14 (m, 3H) 7.26 (m, 1H) 7.66-7.70 (m, 2H) 8.69 (m, 1H) 9.10 (m, 1H). LCMS (m/z) (M+H)=506, Retention time (t$_R$)=0.63 minute.

N-(2-Chloro-3-(2-cyclopropyl-5-(pyrimidin-4-yl)-1H-imidazol-4-yl)-5-fluorophenyl)methanesulfonamide (2J)

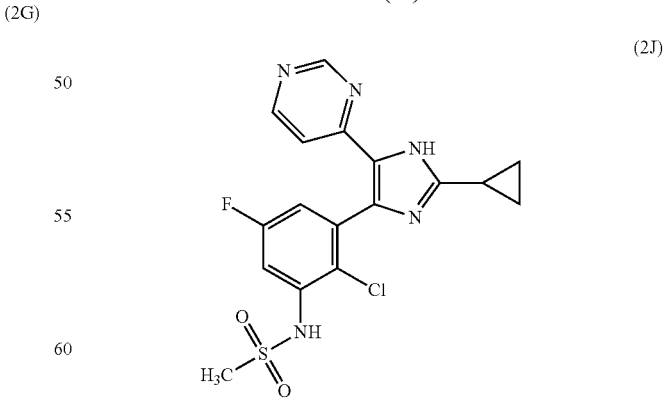

(2J)

$^1$H NMR (300 MHz, CD$_3$CO$_2$D) δ 1.31-1.55 (m, 4H) 2.40-2.60 (m, 1H) 3.15 (s, 3H) 7.26-7.43 (m, 2H) 7.61-7.76 (m, 1H) 8.72-8.84 (m, 1H) 9.23 (s, 1H). LCMS (m/z) (M+H)=408.0, Retention time (t$_R$)=0.48 minute.

N-(2-Chloro-3-(2-cyclopropyl-5-(pyrimidin-4-yl)-1H-imidazol-4-yl)-5-fluorophenyl)propane-1-sulfonamide (2K)

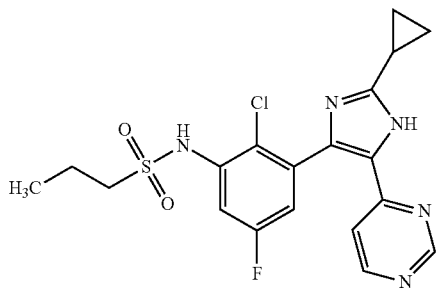

¹H NMR (300 MHz, CD₃CO₂D) δ 1.00-1.05 (t, 3H), 1.34-1.41 (m, 4H) 1.81-1.89 (m, 2H), 2.40-2.60 (m, 1H) 3.20-3.26 (t, 2H) 7.26-7.33 (m, 2H) 7.68-7.72 (m, 1H) 8.76-8.77 (m, 1H) 9.21 (s, 1H). LCMS (m/z) (M+H)=436.1, Retention time ($t_R$)=0.58 minute.

Example 3

Preparation of N-(3-(2-cyclopropyl-5-(2-(methylamino)pyrimidin-4-O-1H-imidazol-4-yl)-2-fluorophenyl)methanesulfonamide, free base (3A-1) and hydrogen chloride salt (3A-2)

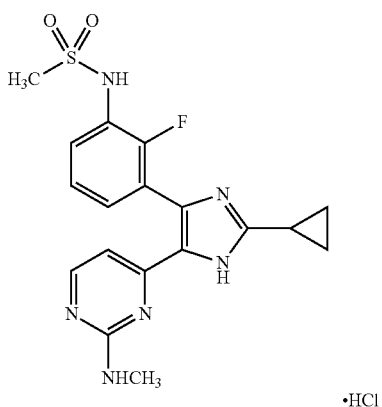

To a solution of 3-(5-(2-chloropyrimidin-4-yl)-2-cyclopropyl-1-((2-(trimethylsilyl)ethoxy) methyl)-1H-imidazol-4-yl)-2-fluoroaniline (I-1i, 81 mg, 0.15 mmol) in dry NMP (2 mL) was added methylamine solution (2.0 M in THF, 0.38 ml, 0.76 mmol). The reaction was then sealed and heated to and maintained at 80° C. for 3 hours. LCMS indicated no conversion. After allowing to cool to room temperature, another solution of methylamine was added (2.0 M in MeOH) and the resulting reaction was heated to and maintained at 80° C. for 2 hours. LCMS indicated complete conversion. The reaction was allowed to cool to room temperature and was diluted with saturated aqueous NH₄Cl solution and extracted with EtOAc (2×). The combined extracts were washed with brine, dried (Na₂SO₄), and concentrated to give N-(3-(2-cyclopropyl-5-(2-(methylamino)pyrimidin-4-yl)-1-((2-(trimethylsilyl)ethoxy)methyl)-1H-imidazol-4-yl)-2-fluorophenyl)methanesulfonamide (78 mg, 0.143 mmol, 95%) as a yellow residue which was carried forward without further purification: LCMS (m/z) 533.2 (MH⁺), $t_R$=0.83 minute.

A solution of N-(3-(2-cyclopropyl-5-(2-(methylamino)pyrimidin-4-yl)-1-((2-(trimethylsilyl)ethoxy)methyl)-1H-imidazol-4-yl)-2-fluorophenyl)methanesulfonamide (78 mg, 0.14 mmol) in EtOH (2 mL) was treated with aqueous 6.0 N HCl solution and the resulting reaction was heated at 60° C. for 1 hour. LCMS indicated complete reaction, and the reaction was allowed to cool to room temperature. The volatiles were removed in vacuo, and the resulting residue was dissolved in DMSO and purified by reverse phase HPLC. Product fractions were combined, neutralized with saturated aqueous NaHCO₃ solution (pH=6), and extracted with DCM (2×). The combined organic portions were dried (Na₂SO₄), and concentrated. The resulting free base (3A-1) was dissolved in ACN, treated with aqueous 1.0 N HCl solution, frozen, and lyophilized to provide N-(3-(2-cyclopropyl-5-(2-(methylamino)pyrimidin-4-yl)-1H-imidazol-4-yl)-2-fluorophenyl)methanesulfonamide (23 mg) as the HCl salt (3A-2): LCMS (m/z) 402.9, (MH⁺), $t_R$=0.44 minute; ¹H NMR (300 MHz, CD₃CO₂D) δ 1.26-1.38 (m, 2H) 1.37-1.52 (m, 2H) 2.41-2.60 (m, 1H) 2.84 (br s, 3H) 3.12 (s, 3H) 7.03 (d, J=6.5 Hz, 1H) 7.29-7.41 (m, 1H) 7.44-7.59 (m, 1H) 7.69-7.84 (m, 1H) 8.29 (d, J=6.5 Hz, 1H).

The following compound was prepared using procedures analogous to the preparation of Example 3A above using the appropriate starting materials.

(S)—N-(3-(2-cyclopropyl-5-(2-(2-hydroxypropylamino)pyrimidin-4-yl)-1H-imidazol-4-yl)-2-fluorophenyl)methanesulfonamide, hydrogen chloride salt (3B)

LCMS (m/z) 447.0 (MH⁺), $t_R$=0.44; ¹H NMR (300 MHz, CD₃CO₂D) δ 1.21 (d, J=5.9 Hz, 3H) 1.38-1.48 (m, 2H) 1.52 (m, 2H) 2.70 (br s, 1H) 3.14 (s, 3H) 3.42-3.61 (m, 2H) 4.04 (br s, 1H) 7.14 (d, J=5.9 Hz, 1H) 7.34-7.47 (m, 1H) 7.49-7.63 (m, 1H) 7.74-7.91 (m, 1H) 8.40 (d, J=6.5 Hz, 1H).

Example 4

Preparation of Methyl (2S)-1-(4-(2-cyclopropyl-4-(2,5-difluoro-3-(methylsulfonamido)-phenyl)-1H-imidazol-5-yl)pyrimidin-2-ylamino)propan-2-ylcarbamate, free base (4A-1), hydrochloride salt (4A-2) and trifluoroacetate salt (4A-3)

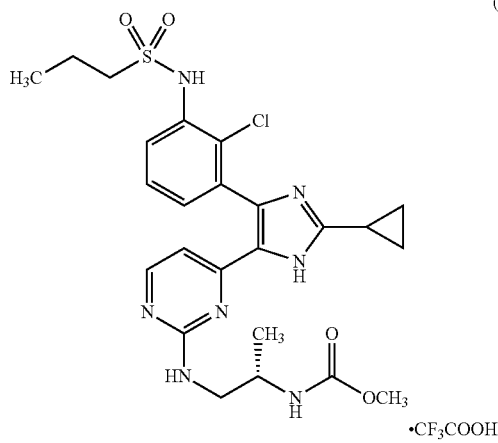

To a mixture of (S)-tert-butyl 1-(4-(4-bromo-2-cyclopropyl-1-((2-(trimethylsilyl)ethoxy)methyl)-1H-imidazol-5-yl)pyrimidin-2-ylamino)propan-2-ylcarbamate (I-1a, 256 mg, 0.45 mmol), N-(2-chloro-3-(4,4,5,5-tetramethyl-1,3,2-dioxaborolan-2-yl)phenyl)propane-1-sulfonamide (SM-10, 292 mg, 0.81 mmol), aqueous 2.0 M Na$_2$CO$_3$ solution in DME (4 mL) was added PdCl$_2$(dppf)•DCM. The reaction vial was sealed and irradiated at 120° C. for 10 minutes in a microwave reactor. LCMS indicated complete conversion and the reaction was allowed to cool to room temperature. The reaction mixture was diluted with water and extracted with EtOAc (2×). The combined organic portions were washed with water, brine, dried (Na$_2$SO$_4$), and concentrated to furnish a dark red oil. Purification by flash chromatography (SiO$_2$, 50-100% EtOAc in heptane) provided (S)-tert-butyl 1-(4-(4-(2-chloro-3-(propylsulfonamido)phenyl)-2-cyclopropyl-1-((2-(trimethylsilyl)ethoxy)methyl)-1H-imidazol-5-yl)pyrimidin-2-ylamino)propan-2-ylcarbamate (4A-1: 116 mg, 0.14 mmol) as a yellow oil: LCMS (m/z) 720.3, (MH), $t_R$=1.03 minutes.

A solution of (S)-tert-butyl 1-(4-(4-(2-chloro-3-(propylsulfonamido)phenyl)-2-cyclopropyl-1-((2-(trimethylsilyl)ethoxy)methyl)-1H-imidazol-5-yl)pyrimidin-2-ylamino)propan-2-ylcarbamate (116 mg, 0.14 mmol) in EtOH (2 mL) was treated with aqueous 6.0 N HCl solution (0.8 mL, 4.8 mmol) and the resulting reaction was heated to 60° C. for 30 minutes, then at room temperature for 40 minutes. The reaction was allowed to cool to room temperature and the volatiles were removed in vacuo. Further drying under high vacuum afforded (S)—N-(3-(5-(2-(2-aminopropylamino)pyrimidin-4-yl)-2-cyclopropyl-1H-imidazol-4-yl)-2-chlorophenyl)propane-1-sulfonamide (80 mg, 0.15 mmol) as the HCl salt (4A-2) which was used without further purification: LCMS (m/z) 490.2 (MH$^+$), $t_R$=0.48 minute.

To a mixture of (S)—N-(3-(5-(2-(2-aminopropylamino)pyrimidin-4-yl)-2-cyclopropyl-1H-imidazol-4-yl)-2-chlorophenyl)propane-1-sulfonamide in THF-water (1:1, 2 mL) at 0° C. was added solid NaHCO$_3$ (137 mg, 1.6 mmol) and the resulting mixture was stirred for 5 minutes. Methyl chloroformate (14 μL, 0.18 mmol) was added and the reaction mixture was stirred at 0° C. for 15 minutes. The reaction was diluted with water and extracted with EtOAc (2×). The combined organic portions were washed with water, brine, dried (Na$_2$SO$_4$), and concentrated. The resulting residue was dissolved in DMSO and purified by reverse phase HPLC. Product fractions were combined and lyophilized to give (S)-methyl 1-(4-(4-(2-chloro-3-(propylsulfonamido)phenyl)-2-cyclopropyl-1H-imidazol-5-yl)pyrimidin-2-ylamino)propan-2-ylcarbamate (19.9 mg) as the TFA salt (4A-3): LCMS (m/z) 548.0 (MH$^+$), $t_R$=0.61 minute, $^1$H NMR (400 MHz, CD$_3$OD) δ 1.04 (t, J=7.4 Hz, 3H) 1.14 (d, J=6.6 Hz, 3H) 1.27 (t, J=4.5 Hz, 2H) 1.34-1.44 (m, 2H) 1.80-1.95 (m, 2H) 3.14-3.21 (m, 2H) 3.67 (br s, 3H) 3.97 (br s, 1H) 6.40 (br s, 1H) 7.45 (d, 7.0 Hz, 1H) 7.54 (m, 1H) 7.84 (d, J=7.4 Hz, 1H) 8.13 (d, J=5.1 Hz, 1H).

The compounds listed below were prepared using procedures analogous to the preparation of Example 4A using the appropriate starting materials and isolated as either their free base or salt form (generally, the trifluoroacetate or hydrogen chloride salt).

(S)-Methyl 1-(4-(2-tert-butyl-4-(2-fluoro-3-(propylsulfonamido)phenyl)-1H-imidazol-5-yl)pyrimidin-2-ylamino)propan-2-ylcarbamate (4B)

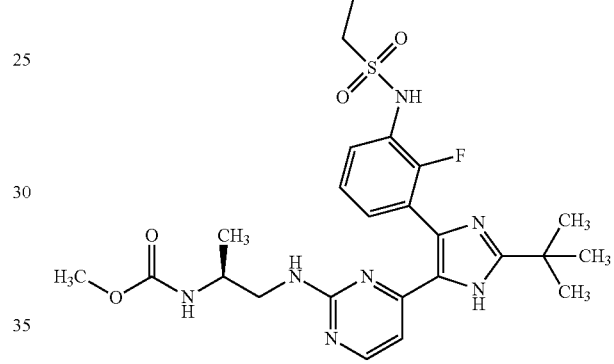

$^1$H NMR (400 MHz, CD$_3$OD) δ1.02 (t, J=7.4 Hz, 6H) 1.56 (s, 9H) 1.77-1.92 (m, 2H) 2.98 (br s, 1H) 3.09-3.16 (m, 2H) 3.25 (br s, 1H) 3.61 (s, 3H) 3.79 (br s, 1H) 6.97 (br s, 1H) 7.30-7.47 (m, 2H) 7.65-7.77 (m, 1H) 8.18 (d, J=3.9 Hz, 1H). LCMS (m/z) (M+H)=548.2, Retention time ($t_R$)=0.65 minute.

(S)-Methyl 1-(4-(2-cyclopropyl-4-(2-fluoro-3-(propylsulfonamido)phenyl)-1H-imidazol-5-yl)pyrimidin-2-ylamino)propan-2-ylcarbamate (4C)

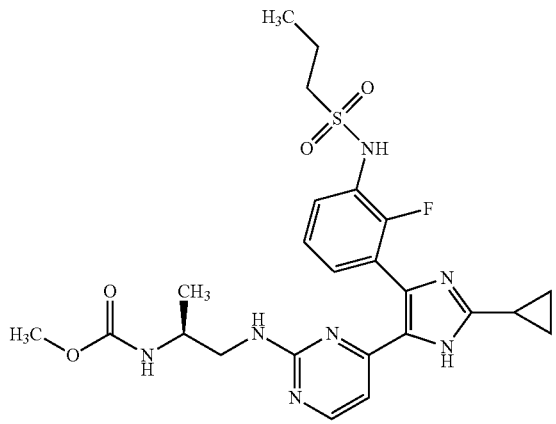

¹H NMR (400 MHz, CD₃OD) δ 1.05 (t, J=7.4 Hz, 3H) 1.09-1.19 (m, 3H) 1.38 (t, J=4.3 Hz, 2H) 1.43-1.54 (m, 2H) 1.80-1.93 (m, 2H) 2.58 (br s, 1H) 3.15-3.23 (m, 2H) 3.53-3.63 (m, 1H) 3.65 (s, 4H) 3.95 (d, J=7.0 Hz, 1H) 6.74-6.86 (m, 1H) 7.38-7.51 (m, 2H) 7.78 (m, 1H) 8.27 (d, J=6.3 Hz, 1H). LCMS (m/z) (M+H)=532.2, Retention time (t$_R$)=0.62 minute.

(S)-Methyl 1-(4-(2-cyclopropyl-4-(3-methyl-5-(1-methylethylsulfonamido)phenyl)-1H-imidazol-5-yl)pyrimidin-2-ylamino)propan-2-ylcarbamate (4D)

(4D)

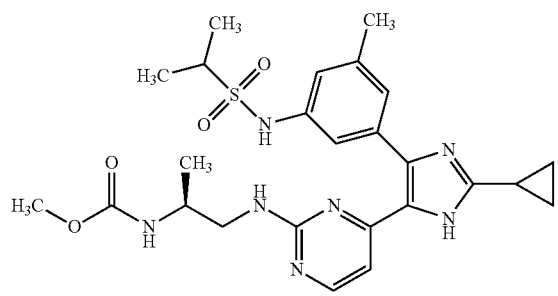

¹H NMR (400 MHz, CD₃OD) δ 1.06 (d, J=6.3 Hz, 3H) 1.24 (m, 10H) 2.31 (s, 3H) 2.38-2.55 (m, 1H) 2.76-3.07 (m, 1H) 3.43-3.74 (m, 5H) 3.78-4.03 (m, 1H) 6.37-6.65 (m, 1H) 7.07 (s, 1H) 7.14 (br s, 1H) 7.21 (br s, 1H) 7.92-8.24 (m, 1H). LCMS (m/z) (M+H)=528.2, Retention time (t$_R$)=0.62 minute.

(S)-Methyl 1-(4-(2-tert-butyl-4-(2-fluoro-3-(3,3,3-trifluoropropylsulfonamido)phenyl)-1H-imidazol-5-yl)pyrimidin-2-ylamino)propan-2-ylcarbamate (4E)

(4E)

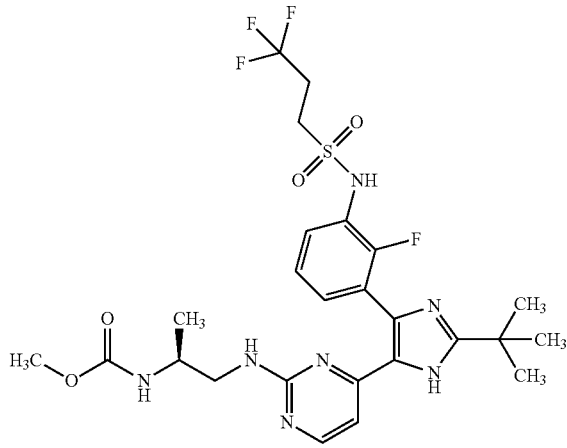

¹H NMR (400 MHz, CD₃OD) δ 1.04 (br. s., 3H) 1.56 (s, 9H) 2.62-2.86 (m, 2H) 2.91-3.05 (m, 1H) 3.36-3.46 (m, 3H) 3.61 (s, 3H) 3.78 (br s, 1H) 6.96-7.10 (m, 1H) 7.40 (m, 1H) 7.47 (m, 1H) 7.71 (m, 1H) 8.18 (d, J=3.5 Hz, 1H). LCMS (m/z) (M+H)=602.2, Retention time (t$_R$)=0.68 minute.

(S)-Methyl 1-(4-(2-tert-butyl-5-(5-chloro-2-fluoro-3-(propylsulfonamido)phenyl)-1H-imidazol-4-yl)pyrimidin-2-ylamino)propan-2-ylcarbamate (4F)

(4F)

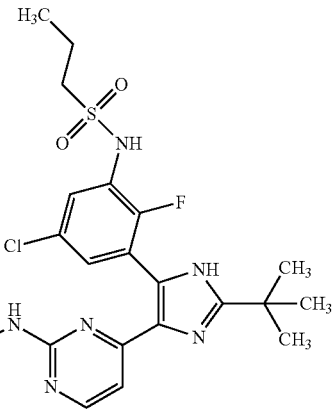

LCMS (m/z) (M+H)=582.4, Retention time (t$_R$)=0.73 minute.

N-(3-(5-(2-(2-Cyanoethylamino)pyrimidin-4-yl)-2-cyclopropyl-1H-imidazol-4-yl)-2-fluorophenyl)propane-1-sulfonamide (4G)

(4G)

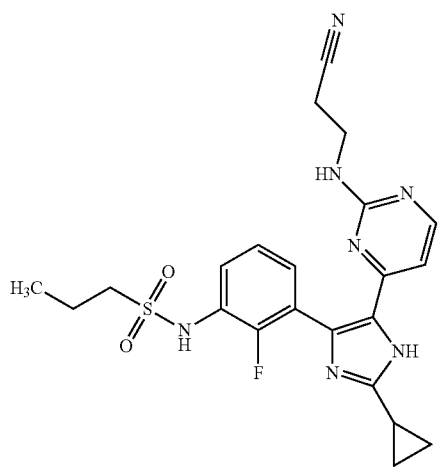

¹H NMR (400 MHz, CD₃OD) δ 1.03 (t, J=7.4 Hz, 3H) 1.22-1.31 (m, 2H) 1.32-1.43 (m, 2H) 1.78-1.92 (m, 2H) 2.30-2.42 (m, 1H) 2.53 (br s, 2H) 3.10-3.19 (m, 2H) 3.48 (m, 2H) 7.33-7.44 (m, 2H) 7.72 (m, 1H) 8.27 (d, J=5.5 Hz, 2H). LCMS (m/z) (M+H)=470.1, Retention time (t$_R$)=0.57 minute.

3-(4-(2-Cyclopropyl-4-(2-fluoro-3-(propylsulfonamido)phenyl)-1H-imidazol-5-yl)pyrimidin-2-ylamino)propanamide (4H)

(4H)

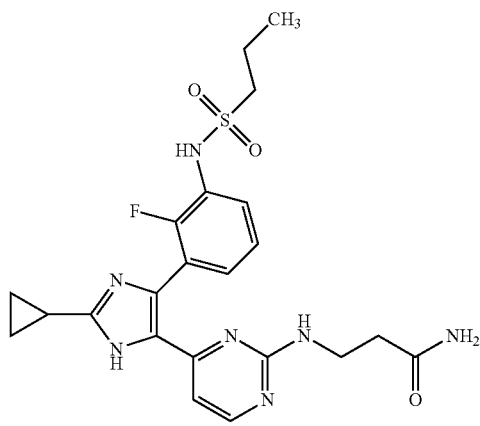

LCMS (m/z) (M+H)=488.1, Retention time ($t_R$)=0.48 minute.

(S)-Methyl 1-(4-(2-tert-butyl-4-(2,4-difluoro-3-(propylsulfonamido)phenyl)-1H-imidazol-5-yl)pyrimidin-2-ylamino)propan-2-ylcarbamate (4I)

(4I)

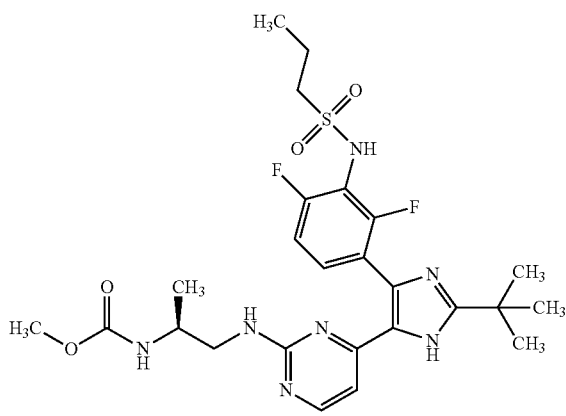

LCMS (m/z) (M+H)=566.2, Retention time ($t_R$)=0.68 minute.

(S)-Methyl 1-(4-(2-cyclopropyl-4-(3-(propylsulfonamido)phenyl)-1H-imidazol-5-pyrimidin-2-ylamino)propan-2-ylcarbamate (4J)

(4J)

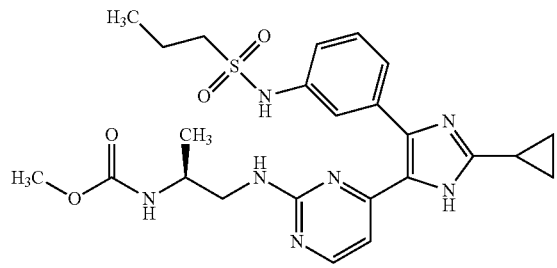

$^1$H NMR (300 MHz, CD$_3$CO$_2$D) δ 1.00 (t, J=7.5 Hz, 3H), 1.22 (d, J=6.7 Hz, 3H), 1.28-1.43 (m, 2H), 1.51 (m, 2H), 1.72-1.89 (m, 2H), 2.62 (m, 1H), 3.18 (m, 2H), 3.64-3.80 (m, 1H), 3.73 (s, 3H), 3.82-3.94 (m, 1H), 4.11 (m, 1H), 6.77 (d, J=6.2 Hz, 1H), 7.33-7.63 (m, 4H), 8.20 (d, J=6.2 Hz, 1H). LCMS (m/z) (M+H)=514.4, Retention time ($t_R$)=0.57 minute.

(S)-Methyl 1-(4-(2-cyclopropyl-4-(3-(methylsulfonamido)phenyl)-1H-imidazol-5-yl)pyrimidin-2-ylamino)propan-2-ylcarbamate (4K)

(4K)

$^1$H NMR (300 MHz, CD$_3$CO$_2$D) δ 1.22 (d, J=6.7 Hz, 3H), 1.37 (m, 2H), 1.50 (m, 2H), 2.62 (m, 1H), 3.07 (s, 3H), 3.18 (m, 1H), 3.72 (s, 3H), 3.88 (m, 1H), 4.10 (m, 1H), 6.79 (d, J=6.2 Hz, 1H), 7.36-7.69 (m, 4H), 8.21 (d, J=6.2 Hz, 1H). LCMS (m/z) (M+H)=486.2, Retention time ($t_R$)=0.50 minute.

Example 5

Preparation of (S)-methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate (5A)

(5A)

A glass bomb was charged with (S)-methyl 1-(4-(5-bromo-2-cyclopropyl-1H-imidazol-4-yl)pyrimidin-2-ylamino)propan-2-ylcarbamate (I-1b, 9.0 g, 22.7 mmol), solid anhydrous Na$_2$CO$_3$ (9.65 g, 91 mmol), 2-chloro-5-fluoro-3-(4,4,5,5-tetramethyl-1,3,2-dioxaborolan-2-yl)aniline (SM-8, 16.65 g, 65% by $^1$H NMR assay, 39.8 mmol), DME (60 ml) and water (30 mL). The resulting mixture was thoroughly sparged with Argon for 10 minutes, followed by addition of Pd(PPh$_3$)$_4$ (2.63 g, 2.28 mmol), and another Argon sparge was repeated for 5 minutes. The reaction vessel was sealed, heated at 105° C. in an oil bath for 17 hours. LCMS indicated complete conversion, and the reaction was allowed to cool to room temperature. The reaction mixture was partitioned between EtOAc (60 mL and water (50 ml) and the layers separated. The organic portion was washed with brine (60 mL), dried ($Na_2SO_4$), concentrated to a light brown oil. Purification by flash chromatography ($SiO_2$, 0-5% MeOH in DCM) furnished (S)-methyl 1-(4-(5-(3-amino-2-chloro-5-fluorophenyl)-2-cyclopropyl-1H-imidazol-4-yl)pyrimidin-2-ylamino)propan-2-ylcarbamate (9.71 g, 21.1 mmol, 93%) as a light yellow solid: LCMS (m/z) 460.1 ($MH^+$), $t_R$=0.55 minute, $^1H$ NMR (400 MHz, $CD_3CO_2D$) δ 1.20 (d, J=6.7 Hz, 3H), 1.26 (app br s, 2H), 1.31-1.48 (m, 2H), 2.45-2.58 (m, 1H), 3.11-3.27 (m, 1H), 3.71 (s, 3H), 3.74-3.85 (m, 1H), 4.00-4.17 (m, 1H), 6.51 (d, J=6.3 Hz, 1H), 6.58-6.71 (m, 1H), 6.71-6.83 (m, 1H), 8.15 (d, J=6.7 Hz, 1H).

To a solution of (S)-methyl 1-(4-(5-(3-amino-2-chloro-5-fluorophenyl)-2-cyclopropyl-1H-imidazol-4-yl)pyrimidin-2-ylamino)propan-2-ylcarbamate (8.36 g, 18.2 mmol) in dry pyridine (40 mL) at 0° C. was added methanesulfonyl chloride (5.6 mL, 72.7 mmol), followed by the removal of cold bath. The reaction was stirred at room temperature for 2 hours. LCMS indicated complete conversion to sulfonylated products and the reaction was quenched with water (2.5 mL) at 0° C. The resulting mixture was stirred at 0° C. for an additional 15 minutes and then heated in a 50° C. oil bath for 20 minutes. After allowing to cool to room temperature, the volatile components were removed by rotary evaporator in vacuo, and then dried under high vacuum. The resulting residue was diluted with DME (100 mL), followed by the addition of saturated aqueous $Na_2CO_3$ solution (75 mL). The reaction mixture was heated at 55° C. for 1 hour. LCMS indicated complete conversion to the desired product. The reaction was allowed to cool to room temperature and partitioned upon standing. The layers were separated and the organic portion was filtered through a sintered funnel and filter cake was thoroughly rinsed with methanol. The combined filtrates were again filtered through a sintered funnel and the filtrates concentrated. The resulting residue was dissolved in aqueous NaOH (0.20 M, 150 ml) and the solution was washed with EtOAc (75, 50 mL). The combined organic portions were back extracted with aqueous 0.2 N NaOH solution (50, 25 mL). The combine basic aqueous phases were acidified with aqueous 3.0 M HCl solution (15 mL) to pH 5-6, and milky product suspension was extracted into EtOAc (150 mL). The organic portion was washed with 0.1M sodium phosphate buffer (pH 7, 50 ml), dried ($Na_2SO_4$), and concentrated to a light yellow foam (9.2 g) which was dissolved in DCM (120 mL) and treated with a palladium scavenger (5.0 g, SiliaBond DMT, loading 0.57 mmol/g, Silicycle, Catalog Number R79030B) overnight. Further dilution with DCM (120 mL) and methanol (12 mL) at 30° C. followed by filtration through Celite and concentration furnished a light yellow residue (8.2 g). Crystallization from ethanol (90 mL) followed by drying under high vacuum in a drying pistol ($P_2O_5$, 100° C.) provided (5)-methyl 1-(4-(5-(2-chloro-5-fluoro-3-(methylsulfonamido)phenyl)-2-cyclopropyl-1H-imidazol-4-yl)pyrimidin-2-ylamino)propan-2-ylcarbamate (5A, 7.5 g, 13.9 mmol, 76%) was obtained as a fine white powder: LCMS (m/z) 538.1 ($MH^+$), $t_R$=0.56 minute; $^1H$ NMR (300 MHz, $CD_3CO_2D$) δ 1.20 (d, J=6.7 Hz, 5H), 1.25-1.41 (m, 2H), 2.35-2.56 (m, 1H), 3.13 (s, 3H), 3.16-3.27 (m, 1H), 3.71 (s, 3H), 3.77 (dd, J=13.04, 3.37 Hz, 1H), 3.97-4.21 (m, 1H), 6.42 (d, J=6.45 Hz, 1H), 7.22 (dd, J=8.20, 2.93 Hz, 1H), 7.62 (dd, J=9.67 Hz, 2.93 Hz, 1H), 8.10-8.30 (m, 1H).

Alternatively, (S)-methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate (5A) can also be prepared using the following procedure.

A 1-Liter, 3-necked round bottom flask was equipped with a mechanical stirrer, a thermometer a reflux condenser, a heating mantle and a nitrogen inlet/outlet, was charged with 450 mL of toluene. The solvent was heated at reflux for 2 hours. The solvent was cooled to room temperature under nitrogen and was used for the reaction. Another 1-Liter, three-necked, round-bottomed flask, equipped with a mechanical stirrer, a thermometer, a reflux condenser, a heating mantle and a nitrogen inlet/outlet, was charged at with sodium tert-butoxide (25 g), 1,3-dibromo-2-chloro-5-fluorobenzene (50 g), 400 mL of degassed toluene, and benzophenone imine (33 g). The mixture was stirred at 22-25° C. for 10 minutes. A vacuum/nitrogen-fill cycle was performed three times. To the mixture was added racemic BINAP (3.8 g) and $Pd_2$ $dba_3$ (1.9 g) at 22-25° C. The mixture was heated to an internal temperature of 83-87° C. over 1 hour. (Upon reaching the batch temperature at 80° C., the outlet vent was closed off). The mixture was heated at 83-87° C. for 3 hours. The mixture was cooled to 22-25° C. and 400 mL of water was added. The mixture was stirred for 30 minutes. The organic layer was separated. The aqueous layer was extracted with 100 mL of toluene. The combined organic phase was washed with 200 mL of water.

To the above solution (~600 mL) was transferred to a 2-Liter, three-necked, round-bottomed flask, equipped with a mechanical stirrer, a thermometer, a reflux condenser, a heating mantle and a nitrogen inlet/outlet. To the solution was added 200 mL of 6 N aqueous hydrochloric acid. The mixture was stirred and heated at 57-63° C. for 4 hours. The mixture was cooled to 22-25° C. The mixture was distilled under vacuum to a final volume of <500 mL. To the biphasic solution was added 1,000 mL of heptane. The resulting slurry was cooled to 0-5° C. and stirred for 2 hours. The dark bilayer slurry was filtered through a polypropylene filter paper with suction. The filter cake was washed with 2×50 mL of heptane. The solids were dried in an oven at 50° C. for 5 hours under vacuum to afford 33.8 g of crude hydrogen chloride salt of 3-bromo-2-chloro-5-fluoroaniline.

The above solids were transferred to a 1-L, three-necked, round-bottomed flask, containing 200 mL of toluene and 100 g of 20% (w/w) sodium carbonate solution. The mixture was stirred at 22-25° C. for 30 minutes or until all solids have dissolved. The organic phase was separated and washed with Separate layers. Wash the organic layer with 50 g of 20% (w/w) of sodium chloride solution. The solution was distilled under vacuum to a final volume of ~75 mL and then held it at 22-25° C. The solution was then diluted with 90 mL of heptane and filtered through a bed of 100 g of silica gel (60-230 mesh). The product off the silica gel pad bed was washed with 1.1 L of a solution of toluene/heptane v/v, 1/3) by applying a slight vacuum pressure. The filtered solution was distilled to a final volume of ~70 mL and diluted with 250 mL of heptane. While maintaining the internal temperature below 27° C., 6 N aqueous hydrochloric acid (60 mL) as added drop wise over 15 minutes. The resulting white slurry was stirred at 20-25° C. for 5 hours. The batch was then cooled to 0-5° C. over 30 minutes and stirred at this temperature for 3 hours. The slurry was filtered through a polypropylene filter paper with suction and the filtered solid was washed with 80 mL of heptane. The solids were dried under vacuum in an oven at 50° C. to constant weight (18 hours) to obtain 26 g (57%) of 3-bromo-2-chloro-5-fluoroaniline as the hydrogen chloride salt (white solid with HPLC purity>98%).

A mixture of 3-bromo-2-chloro-5-fluoroaniline hydrogen chloride (5.0 g, 19.163 mmol), $PiN_2B_2$ (6.81 g, 26.818 mmol), P(C$_6$H$_{11}$)$_3$ (0.536 g, 1.912 mmol), potassium acetate (5.632 g, 57.411 mmol) and 110 mL toluene in a 250 mL, 3-necked round bottomed flask was heated to reflux. About 10 mL of solvent was distilled at atmospheric pressure. The mixture was cooled to approximately 60° C. followed by the addition of Pd$_2$(dba)$_3$ (0.877 g. 0.958 mmol). The reaction mixture was heated at 110° C. for 0.5 hours. HPLC of the reaction mixture indicated completion of the reaction. Heating was stopped and reaction mixture was cooled to 20-22° C. The mixture was filtered through pad of Celite and basic alumina. The black cake was washed with 100 mL of toluene. The filtrate was evaporated under vacuum. The residue was used as such for the next reaction.

In a 1 Liter round bottom, 4-neck flask equipped with an overhead stirrer, thermocouple, condenser, heating mantle and nitrogen inlet/outlet were placed of 4-(4-bromo-2-cyclopropyl-1-((2-(trimethylsilyl)ethoxy)methyl)-1H-imidazol-5-yl)-2-chloropyrimidine (50 g, 0.116 mol), (S)-methyl 1-aminopropan-2-ylcarbamate hydrogen chloride salt (25.5 g, 0.1512 mol), Na$_2$CO$_3$ (49.3 g. 0.4653 mol) and 400 mL of DMSO. The mixture was stirred and heated at 90° C. After 16 hours, the reaction was complete as indicated by disappearance of 4-(4-bromo-2-cyclopropyl-1-((2-(trimethylsilyl)ethoxy)-methyl)-1H-imidazol-5-yl)-2-chloropyrimidine by HPLC. The reaction mixture was cooled to 25° C. and then added slowly to a mixture of water (1.5 L) and MTBE (500 mL). The mixture was stirred until all solids had dissolved (45 minutes). The organic phase was separated and the aqueous phase was extracted once with MTBE (500 mL). The combined organic phase was washed once with 10% citric acid solution (250 mL) and once with water (250 mL) and then with brine (150 mL). The organic phase was dried over anhydrous MgSO$_4$, filtered and concentrated under reduced pressure on the rotary evaporator to an oil (66 g). The product ((S)-methyl 1-(4-(4-bromo-2-cyclopropyl-1-((2-(trimethylsilyl)ethoxy)methyl)-1H-imidazol-5-yl)pyrimidin-2-ylamino)propan-2-ylcarbamate) contained some residual solvent and was used as such in the next step.

A 100-mL, 3-necked round bottomed flask with a small magnetic stirrer was charged with (S)-methyl 1-(4-(4-bromo-2-cyclopropyl-1-((2-(trimethylsilyl)ethoxy)methyl)-1H-imidazol-5-yl)pyrimidin-2-ylamino)propan-2-ylcarbamate (5.746 g, 10.934 mmol), 3-bromo-2-chloro-N-(diphenylmethylene)-5-fluoroaniline (4.15 g, 15.322 mmol), Na$_2$CO$_3$ (3.48 g, 32.83 mmol), degassed DME (57 mL) and degassed water (5.7 mL). Nitrogen gas was bubbled through the mixture for 2-3 minutes followed by the addition of Pd(PPh$_3$)$_4$ (1.265 g, 1.095 mmol). The mixture was heated at 82° C. HPLC of the reaction mixture after 22 hours indicated completion.

The reaction mixture was evaporated under vacuum. The residue was stirred with ethyl acetate (100 mL) and water (50 mL). The mixture was filtered and the organic layer was separated and saved. The aqueous layer was extracted once with ethyl acetate (50 mL). The combined organic phase was washed once with water (50 mL), dried over MgSO$_4$, filtered and evaporated under vacuum to give 15.349 (26.01 mmol, 237.61%) of crude (S)-methyl 1-(4-(4-(3-amino-2-chloro-5-fluorophenyl)-2-cyclopropyl-1-((2-(trimethylsilyl)ethoxy)methyl)-1H-imidazol-5-yl)pyrimidin-2-ylamino)propan-2-ylcarbamate (contains PPh$_3$O, catalyst, solvent and other impurities) as a dark brown oil. The crude product was used as such for the next hydrolysis step.

A mixture of the crude (S)-methyl 1-(4-(4-(3-amino-2-chloro-5-fluorophenyl)-2-cyclopropyl-1-((2-(trimethylsilyl)ethoxy)methyl)-1H-imidazol-5-yl)pyrimidin-2-ylamino)propan-2-ylcarbamate (15.349 g), p-toluenesulfonic acid (3.64 g, 21.132 mmol) and methanol (70 mL) in a 100 mL, 3-necked round bottomed flask was heated at reflux for 1 hour. HPLC indicted completion of reaction. The reaction mixture was evaporated under vacuum and the residue was stirred with 2 N HCl (50 mL) and ethyl acetate (75 mL). The aqueous layer was separated and the organic layer was extracted once with 2 N HCl (40 mL). The combined aqueous layers were extracted once with ethyl acetate (50 mL) and then neutralized with aq NaOH (4 N). The product was extracted with 2×50 mL of ethyl acetate. The organic layer was washed once with water (40 mL), dried over MgSO$_4$ and evaporated under vacuum to give 5.136 g (11.190 mmol) of crude (S)-methyl 1-(4-(4-(3-amino-2-chloro-5-fluorophenyl)-2-cyclopropyl-1H-imidazol-5-yl)pyrimidin-2-ylamino) propan-2-ylcarbamate as a brown oil.

A 3-necked 100 mL round bottomed flask was charged with crude (S)-methyl 1-(4-(4-(3-amino-2-chloro-5-fluorophenyl)-2-cyclopropyl-1H-imidazol-5-yl)pyrimidin-2-ylamino)propan-2-ylcarbamate (5.136 g), THF (50 mL) and triethylamine (6.21 mL, 44.63 mmol). The solution was cooled to 0-5° C. and MeSO$_2$Cl (3.836 g, 33.508 mmol) was added slowly (highly exothermic) keeping the batch temperature<5° C. HPLC of the reaction mixture after 3 hours indicated completion of the reaction. 50% aqueous NaOH (20 mL) was slowly added to the reaction mixture at 0-5C. The addition was exothermic. The batch temperature rose from approximately 2° C. to 19° C. within a few minutes. The mixture was stirred at 19° C. HPLC of the reaction mixture after 16 hours indicated completion of the reaction. The reaction mixture was evaporated under vacuum at 22-25° C. to remove THF. The mixture was diluted with water and the mixture was extracted with 2×75 mL of TBME. To the aqueous phase was added ethyl acetate (100 mL). The pH of the aqueous phase was then adjusted to 5.75-6.0 by slow addition of a 3 N HCl solution. The organic layer was separated and the aqueous phase extracted with ethyl acetate (2×50 mL). The ethyl acetate phases were combined and washed with water (2×50 mL), dried over MgSO$_4$, and evaporated under vacuum to give a light yellow foamy solid (3.42 g, 6.357 mmol). To the crude product (3.42 g) was added isopropanol (35 mL) and the mixture was heated at reflux for 10 minutes. The suspension was cooled to 20-22° C. and then to 0-5° C. The mixture was stirred at 0-5° C. for 30 minutes and then filtered. The cake was washed with ice-cold isopropanol. The product was dried at 65° C. in vacuo for 18 hours to give 2.516 g (4.676 mmol, HPLC purity>98%) of the desired product (S)-methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate (5A).

PHARMACOLOGICAL DATA

Utility for the compounds of the present invention is supported by the data observed in one or more of the following assays.

Raf/Mek Amplified Luminescence Proximity Homogeneous Assay
(Alpha Screen)
Buffers
Assay buffer: 50 mM Tris, pH 7.5, 15 mM MgCl$_2$, 0.01% Bovine Serum Albumin (BSA), 1 mM dithiothreitol (DTT)
Stop buffer: 60 mM ethylenediaminetetraacetic acid (EDTA), 0.01% Tween® 20
Bead buffer: 50 mM Tris, pH 7.5, 0.01% Tween® 20
Materials
b-Raf(V600E), active
biotinylated Mek, kinase dead Alpha Screen detection kit (available from PerkinElmer™, #6760617R)
Anti phospho-MEK1/2 (available from Cell Signaling Technology, Inc. #9121)
384 well assay plates (White Greiner® plates, #781207)
Assay Conditions
b-Raf(V600E) approximately 4 pM
c-Raf approximately 4 nM
biotinylated Mek, Kinase dead approximately 10 nM
ATP 10 μM
Pre-incubation time with compounds 60 minutes at room temperature
Reaction time 1 or 3 hours at room temperature
Assay Protocol Raf and biotinylated Mek, kinase dead, were combined at 2× final concentrations in assay buffer (50 mM Tris, pH 7.5, 15 mM $MgCl_2$, 0.01% BSA and 1 mM DTT) and dispensed 10 μl per well in assay plates (Greiner white 384 well assay plates #781207) containing 0.5 μl of 40× of a raf kinase inhibitor test compound diluted in 100% DMSO. The plate was incubated for 60 minutes at room temperature.

The Raf kinase activity reaction was started by the addition of 10 μL per well of 2×ATP diluted in assay buffer. After 3 hours (bRaf(V600E)) or 1 hour (c-Raf), the reactions were stopped with the addition of 10 μL of stop reagent (60 mM EDTA). Phosphorylated product was measured using a rabbit anti-p-MEK (Cell Signaling, #9121) antibody and the Alpha Screen IgG (ProteinA) detection Kit (PerkinElmer #6760617R), by the addition of 30 μL to the well of a mixture of the antibody (1:2000 dilution) and detection beads (1:2000 dilution of both beads) in bead buffer (50 mM Tris, pH 7.5, 0.01% Tween20). The additions were carried out under dark conditions to protect the detection beads from light. A lid was placed on top of the plate and incubated for 1 hour at room temperature, then the luminescence was read on a PerkinElmer Envision instrument. The concentration of each compound for 50% inhibition ($IC_{50}$) was calculated by non-linear regression using XL Fit data analysis software.

Mutant b-Raf(V600E) $IC_{50}$ data for representative compounds of the invention in the Raf/Mek Amplified Luminescence Proximity Homogeneous Assay are shown in the Table I below. Each of the compounds were tested as either their free base or salt form indicated in the table below.

TABLE 1

| Ex. No. | Compound Name | mut-B-RAF IC50 (μM) |
|---|---|---|
| 1A | (S)-methyl 1-(4-(4-(5-chloro-2-fluoro-3-(methylsulfonamido)phenyl)-2-cyclopropyl-1H-imidazol-5-yl)pyrimidin-2-ylamino)propan-2-ylcarbamate | 0.00020 |
| 1B | (S)-Methyl 1-(4-(2-cyclopropyl-4-(2-fluoro-5-methyl-3-(methylsulfonamido)phenyl)-1H-imidazol-5-yl)pyrimidin-2-ylamino)propan-2-ylcarbamate | 0.0002 |
| 1C | (S)-Methyl 1-(4-(2-tert-butyl-4-(3-chloro-5-(methylsulfonamido)phenyl)-1H-imidazol-5-yl)pyrimidin-2-ylamino)propan-2-ylcarbamate, trifluoroacetate salt | 0.00032 |
| 1D | (S)-Methyl 1-(4-(2-tert-butyl-4-(3-chloro-5-(trifluoroethylsulfonamido)phenyl)-1H-imidazol-5-yl)pyrimidin-2-ylamino)propan-2-ylcarbamate, trifluoroacetate salt | 0.23500 |
| 1E | (S)-Methyl 1-(4-(2-tert-butyl-4-(3-chloro-5-(propylsulfonamido)phenyl)-1H-imidazol-5-yl)pyrimidin-2-ylamino)propan-2-ylcarbamate, trifluoroacetate salt | 0.0001 |
| 1F | (S)-Methyl 1-(4-(2-tert-butyl-4-(3-chloro-5-(cyclopropanesulfonamido)phenyl)-1H-imidazol-5-yl)pyrimidin-2-ylamino)propan-2-ylcarbamate, trifluoroacetate salt | 0.0001 |
| 1G | (S)-Methyl 1-(4-(2-tert-butyl-4-(3-chloro-5-(2-methylpropylsulfonamido)phenyl)-1H-imidazol-5-yl)pyrimidin-2-ylamino)propan-2-ylcarbamate, trifluoroacetate salt | 0.0003 |
| 1H | Methyl (2S)-1-(4-(2-tert-butyl-4-(3-chloro-5-(1-methylpropylsulfonamido)phenyl)-1H-imidazol-5-yl)pyrimidin-2-ylamino)propan-2-ylcarbamate, trifluoroacetate salt | 0.0005 |
| 1I | (S)-Methyl 1-(4-(2-tert-butyl-4-(3-chloro-5-(ethylsulfonamido)phenyl)-1H-imidazol-5-yl)pyrimidin-2-ylamino)propan-2-ylcarbamate, trifluoroacetate salt | 0.0001 |
| 1J | (S)-Methyl 1-(4-(2-tert-butyl-4-(3-chloro-5-(1-methylethylsulfonamido)phenyl)-1H-imidazol-5-yl)pyrimidin-2-ylamino)propan-2-ylcarbamate, trifluoroacetate salt | 0.00135 |
| 1K | (S)-Methyl 1-(4-(2-tert-butyl-4-(3-methoxy-4-methyl-5-(1-methylethylsulfonamido)phenyl)-1H-imidazol-5-yl)pyrimidin-2-ylamino)propan-2-ylcarbamate, trifluoroacetate salt | 0.18900 |
| 1L | (S)-Methyl 1-(4-(2-tert-butyl-4-(3-(cyclopropanesulfonamido)-5-methoxy-4-methylphenyl)-1H-imidazol-5-yl)pyrimidin-2-ylamino)propan-2-ylcarbamate, trifluoroacetate salt | 0.15700 |
| 1M | (S)-Methyl 1-(4-(4-(3-chloro-5-(1-methylethylsulfonamido)phenyl)-2-cyclopropyl-1H-imidazol-5-yl)pyrimidin-2-ylamino)propan-2-ylcarbamate, trifluoroacetate salt | 0.00063 |
| 1N | (S)-Methyl 1-(4-(2-tert-butyl-4-(5-chloro-3-(cyclopropanesulfonamido)-2-methylphenyl)-1H-imidazol-5-yl)pyrimidin-2-ylamino)propan-2-ylcarbamate, trifluoroacetate salt | 0.20400 |
| 1O | (S)-Methyl 1-(4-(2-tert-butyl-4-(5-chloro-2-methyl-3-(1-methylethylsulfonamido)phenyl)-1H-imidazol-5-yl)pyrimidin-2-ylamino)propan-2-ylcarbamate | 0.06720 |
| 1P | (S)-Methyl 1-(4-(2-tert-butyl-5-(3-(difluoromethoxy)-5-(1-methylethylsulfonamido)phenyl)-1H-imidazol-4-yl)pyrimidin-2-ylamino)propan-2-ylcarbamate, trifluoroacetate salt | 0.01120 |
| 1Q | (S)-Methyl 1-(4-(2-tert-butyl-4-(3-methyl-5-(1-methylethylsulfonamido)phenyl)-1H-imidazol-5-yl)pyrimidin-2-ylamino)propan-2-ylcarbamate, trifluoroacetate salt | 0.00312 |
| 1R | (S)-Methyl 1-(4-(2-tert-butyl-4-(3-(methylsulfonamido)phenyl)-1H-imidazol-5 -yl)pyrimidin-2-ylamino)propan-2-ylcarbamate, trifluoroacetate salt | 0.03450 |
| 1S | (S)-Methyl 1-(4-(4-(3-chloro-5-(methylsulfonamido)phenyl)-2-cyclopropyl-1H-imidazol-5-yl)pyrimidin-2-ylamino)propan-2-ylcarbamate, trifluoroacetate salt | 0.00048 |
| 1T | (S)-Methyl 1-(4-(4-(2-chloro-3-(methylsulfonamido)phenyl)-2-cyclopropyl-1H-imidazol-5-yl)pyrimidin-2-ylamino)propan-2-ylcarbamate, hydrogen chloride salt | 0.00047 |
| 1U | (S)-Methyl 1-(4-(2-cyclopropyl-4-(2-fluoro-3-(methylsulfonamido)phenyl)-1H-imidazol-5-yl)pyrimidin-2-ylamino)propan-2-ylcarbamate, trifluoroacetate salt | 0.00055 |
| 1V | Methyl (2S)-1-(4-(2-cyclopropyl-4-(2,5-difluoro-3-(methylsulfonamido)phenyl)-1H-imidazol-5-yl)pyrimidin-2-ylamino)propan-2-ylcarbamate | 0.0002 |
| 1W | (S)-Methyl 1-(4-(5-(5-chloro-2-fluoro-3-(propylsulfonamido)phenyl)-2-cyclopropyl-1H-imidazol-4-yl)pyrimidin-2-ylamino)propan-2-ylcarbamate, trifluoroacetate salt | 0.00089 |
| 1X | (S)-Methyl 1-(4-(2-cyclopropyl-4-(2,5-dichloro-3-(methylsulfonamido)phenyl)-1H-imidazol-5-yl)pyrimidin-2-ylamino)propan-2-ylcarbamate, hydrogen chloride salt | 0.00018 |
| 1Y | (S)-Methyl 1-(4-(5-(5-chloro-3-(cyclopropanesulfonamido)-2-fluorophenyl)-2-cyclopropyl-1H-imidazol-4-yl)pyrimidin-2-ylamino)propan-2-ylcarbamate, hydrogen chloride salt | 0.00018 |

TABLE 1-continued

| Ex. No. | Compound Name | mut-B-RAF IC50 (µM) |
|---|---|---|
| 1Z | (S)-Methyl 1-(4-(5-(5-chloro-3-(ethylsulfonamido)-2-fluorophenyl)-2-cyclopropyl-1H-imidazol-4-yl)pyrimidin-2-ylamino)propan-2-ylcarbamate, hydrogen chloride salt | 0.00024 |
| 1AA | (S)-Methyl 1-(4-(5-chloro-2-fluoro-3-(3,3,3-trifluoropropylsulfonamido)phenyl)-2-cyclopropyl-1H-imidazol-4-yl)pyrimidin-2-ylamino)propan-2-ylcarbamate, hydrogen chloride salt | 0.0006 |
| 1AB | (S)-Methyl 1-(4-(4-(2-chloro-5-methyl-3-(methylsulfonamido)phenyl)-2-cyclopropyl-1H-imidazol-5-yl)pyrimidin-2-ylamino)propan-2-ylcarbamate | 0.0011 |
| 1AC | (S)-Methyl 1-(4-(5-(5-chloro-3-(cyclopropylmethylsulfonamido)-2-fluorophenyl)-2-cyclopropyl-1H-imidazol-4-yl)pyrimidin-2-ylamino)propan-2-ylcarbamate, trifluoroacetate salt | 0.00026 |
| 1AD | (S)-Methyl 1-(4-(4-(2-chloro-3-(ethylsulfonamido)-5-fluorophenyl)-2-cyclopropyl-1H-imidazol-5-yl)pyrimidin-2-ylamino)propan-2-ylcarbamate | 0.00043 |
| 1AE | (S)-Methyl 1-(4-(4-(2-chloro-3-(cyclopropanesulfonamido)-5-fluorophenyl)-2-cyclopropyl-1H-imidazol-5-yl)pyrimidin-2-ylamino)propan-2-ylcarbamate | 0.00030 |
| 1AF | Methyl (2S)-1-(4-(4-(2-chloro-6-fluoro-3-(propylsulfonamido)phenyl)-2-cyclopropyl-1H-imidazol-5-yl)pyrimidin-2-ylamino)propan-2-ylcarbamate, trifluoroacetate salt | 0.00045 |
| 1AG | (S)-Methyl 1-(4-(2-tert-butyl-4-(2-chloro-5-fluoro-3-(methylsulfonamido)phenyl)-1H-imidazol-5-yl)pyrimidin-2-ylamino)propan-2-ylcarbamate, trifluoroacetate salt | 0.0010 |
| 1AH | (S)-Methyl 1-(4-(2-tert-butyl-4-(2-chloro-5-fluoro-3-(propylsulfonamido)phenyl)-1H-imidazol-5-yl)pyrimidin-2-ylamino)propan-2-ylcarbamate, trifluoroacetate salt | 0.0010 |
| 1AI | (S)-Methyl 1-(4-(2-tert-butyl-4-(5-chloro-2-fluoro-3-(methylsulfonamido)phenyl)-1H-imidazol-5-yl)pyrimidin-2-ylamino)propan-2-ylcarbamate, trifluoroacetate salt | 0.00028 |
| 1AJ | (S)-Methyl 1-(4-(2-tert-butyl-4-(5-chloro-3-(ethylsulfonamido)-2-fluorophenyl)-1H-imidazol-5-yl)pyrimidin-2-ylamino)propan-2-ylcarbamate, trifluoroacetate salt | 0.00046 |
| 1AK | N-(2-Chloro-3-(5-(2-(2-cyanopropylamino)pyrimidin-4-yl)-2-cyclopropyl-1H-imidazol-4-yl)phenyl)methanesulfonamide | 0.011 |
| 1AL | (S)-Methyl 1-(4-(5-(5-chloro-2-fluoro-3-(methylsulfonamido)phenyl)-2-(1-methylcyclopropyl)-1H-imidazol-4-yl)pyrimidin-2-ylamino)propan-2-ylcarbamate, hydrogen chloride salt | 0.0010 |
| 1AM | (S)-Methyl 1-(4-(5-(2-fluoro-5-methyl-3-(methylsulfonamido)phenyl)-2-(1-methylcyclopropyl)-1H-imidazol-4-yl)pyrimidin-2-ylamino)propan-2-ylcarbamate | 0.0010 |
| 1AN | N-(2-Chloro-3-(5-(2-(propylamino)pyrimidin-4-yl)-1H-imidazol-4-yl)-5-fluorophenyl)propane-1-sulfonamide, trifluoroacetate salt | 0.00039 |
| 1AO | (S)-Methyl 1-(4-(5-(2-chloro-3-(methylsulfonamido)phenyl)-2-(1-methylcyclopropyl)-1H-imidazol-4-yl)pyrimidin-2-ylamino)propan-2-ylcarbamate, trifluoroacetate salt | 0.0010 |
| 1AP | N-(2-Chloro-3-(2-cyclopropyl-5-(2-(propylamino)pyrimidin-4-yl)-1H-imidazol-4-yl)-5-fluorophenyl)methanesulfonamide, trifluoroacetate salt | 0.0050 |
| 1AQ | N-(2-Chloro-3-(2-cyclopropyl-5-(2-(ethylamino)pyrimidin-4-yl)-1H-imidazol-4-yl)-5-fluorophenyl)methanesulfonamide, trifluoroacetate salt | 0.011 |
| 1AR | N-(2-Chloro-3-(2-cyclopropyl-5-(2-(isobutylamino)pyrimidin-4-yl)-1H-imidazol-4-yl)-5-fluorophenyl)methanesulfonamide, trifluoroacetate salt | 0.0050 |
| 1AS | N-(2-Chloro-3-(2-cyclopropyl-5-(2-(ethylamino)pyrimidin-4-yl)-1H-imidazol-4-yl)-5-fluorophenyl)propane-1-sulfonamide, trifluoroacetate salt | 0.0010 |
| 1AT | N-(2-Chloro-3-(2-cyclopropyl-5-(2-(isopropylamino)pyrimidin-4-yl)-1H-imidazol-4-yl)-5-fluorophenyl)methanesulfonamide, trifluoroacetate salt | 0.025 |
| 1AU | N-(2-Chloro-3-(2-cyclopropyl-5-(2-(isopropylamino)pyrimidin-4-yl)-1H-imidazol-4-yl)-5-fluorophenyl)propane-1-sulfonamide, trifluoroacetate salt | 0.0050 |
| 1AV | (R)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate | 0.011 |
| 1AW | (S)-Methyl 1-(4-(5-(5-chloro-2-fluoro-3-(4-fluorophenylsulfonamido)phenyl)-2-cyclopropyl-1H-imidazol-4-yl)pyrimidin-2-ylamino)propan-2-ylcarbamate, trifluoroacetate salt | 0.0010 |
| 1AX | (S)-Methyl 1-(4-(5-(5-chloro-2-fluoro-3-(3-fluorophenylsulfonamido)phenyl)-2-cyclopropyl-1H-imidazol-4-yl)pyrimidin-2-ylamino)propan-2-ylcarbamate, trifluoroacetate salt | 0.00033 |
| 1AY | N-(2-Chloro-3-(5-(2-(2-cyanoethylamino)pyrimidin-4-yl)-2-(1-methylcyclopropyl)-1H-imidazol-4-yl)-5-fluorophenyl)methanesulfonamide | 0.00023 |
| 1AZ | N-(2-Chloro-3-(5-(2-(2-cyanoethylamino)pyrimidin-4-yl)-2-(1-methylcyclopropyl)-1H-imidazol-4-yl)-5-methylphenyl)methanesulfonamide | 0.00029 |
| 1BA | N-(3-(5-(2-(2-Cyanoethylamino)pyrimidin-4-yl)-2-(1-methylcyclopropyl)-1H-imidazol-4-yl)-2-fluoro-5-methylphenyl)methanesulfonamide | 0.00037 |
| 1BB | N-(5-Chloro-3-(5-(2-(2-cyanoethylamino)pyrimidin-4-yl)-2-(1-methylcyclopropyl)-1H-imidazol-4-yl)-2-fluorophenyl)methanesulfonamide | 0.00011 |
| 1BC | N-(2-Chloro-3-(5-(2-(2-cyanoethylamino)pyrimidin-4-yl)-2-(1-methylcyclopropyl)-1H-imidazol-4-yl)phenyl)methanesulfonamide | 0.0010 |
| 1BD | N-(3-(5-(2-Aminopyrimidin-4-yl)-2-tert-butyl-1H-imidazol-4-yl)-5-chloro-2-fluorophenyl)methanesulfonamide, trifluoroacetate salt | 0.0030 |
| 1BE | N-(3-(5-(2-Aminopyrimidin-4-yl)-2-tert-butyl-1H-imidazol-4-yl)-5-chloro-2-fluorophenyl)-2,6-difluorobenzenesulfonamide, trifluoroacetate salt | 0.00013 |
| 1BF | N-(3-(5-(2-Aminopyrimidin-4-yl)-2-cyclopropyl-1H-imidazol-4-yl)-5-chloro-2-fluorophenyl)-2,6-difluorobenzenesulfonamide, trifluoroacetate salt | 0.00010 |
| 1BG | N-(3-(5-(2-Aminopyrimidin-4-yl)-2-cyclopropyl-1H-imidazol-4-yl)-5-chloro-2-fluorophenyl)methanesulfonamide, trifluoroacetate salt | 0.0040 |
| 1BH | N-(3-(5-(2-Aminopyrimidin-4-yl)-2-tert-butyl-1H-imidazol-4-yl)-5-chloro-2-fluorophenyl)propane-1-sulfonamide, trifluoroacetate salt | 0.00008 |
| 1BI | (S)-Methyl 1-(4-(4-(2-chloro-3-(2,6-difluorophenylsulfonamido)-5-fluorophenyl)-2-cyclopropyl-1H-imidazol-5-yl)pyrimidin-2-ylamino)propan-2-ylcarbamate, trifluoroacetate salt | 0.00010 |
| 1BJ | N-(3-(5-(2-Aminopyrimidin-4-yl)-2-tert-butyl-1H-imidazol-4-yl)-2-chloro-5-fluorophenyl)methanesulfonamide, trifluoroacetate salt | 0.0050 |
| 1BK | N-(3-(5-(2-Aminopyrimidin-4-yl)-2-tert-butyl-1H-imidazol-4-yl)-2-chlorophenyl)-2,6-difluorobenzenesulfonamide, trifluoroacetate salt | 0.00022 |
| 1BL | N-(3-(5-(2-Aminopyrimidin-4-yl)-2-tert-butyl-1H-imidazol-4-yl)-2-chlorophenyl)methanesulfonamide, trifluoroacetate salt | 0.055 |
| 1BM | (S)-Methyl 1-(4-(4-(5-chloro-3-(3,5-difluorophenylsulfonamido)-2-fluorophenyl)-2-cyclopropyl-1H-imidazol-5-yl)pyrimidin-2-ylamino)propan-2-ylcarbamate, trifluoroacetate salt | 0.00037 |
| 1BN | (S)-Methyl 1-(4-(5-chloro-2-fluoro-3-(4-(trifluoromethyl)phenylsulfonamido)phenyl)-2-cyclopropyl-1H-imidazol-5-yl)pyrimidin-2-ylamino)propan-2-ylcarbamate, trifluoroacetate salt | 0.0070 |

TABLE 1-continued

| Ex. No. | Compound Name | mut-B-RAF IC50 (μM) |
|---|---|---|
| 1BO | (S)-Methyl 1-(4-(2-cyclopropyl-4-(2-fluoro-5-methyl-3-(2,2,2-trifluoroethylsulfonamido)phenyl)-1H-imidazol-5-yl)pyrimidin-2-ylamino)propan-2-ylcarbamate | 0.00025 |
| 1BP | N-(3-(5-(2-Aminopyrimidin-4-yl)-2-tert-butyl-1H-imidazol-4-yl)-2-chloro-5-fluorophenyl)-2,6-difluorobenzenesulfonamide, trifluoroacetate salt | 0.00026 |
| 1BQ | N-(3-(5-(2-Aminopyrimidin-4-yl)-2-cyclopropyl-1H-imidazol-4-yl)-2-chloro-5-fluorophenyl)methanesulfonamide, trifluoroacetate salt | 0.012 |
| 1BR | N-(3-(5-(2-Aminopyrimidin-4-yl)-2-cyclopropyl-1H-imidazol-4-yl)-2-chloro-5-fluorophenyl)-2,6-difluorobenzenesulfonamide, trifluoroacetate salt | 0.00019 |
| 1BS | N-(3-(5-(2-Aminopyrimidin-4-yl)-2-cyclopropyl-1H-imidazol-4-yl)-2-chloro-5-fluorophenyl)propane-1-sulfonamide, trifluoroacetate salt | 0.00020 |
| 1BT | (S)-Methyl 1-(4-(4-(5-chloro-2-fluoro-3-(methylsulfonamido)phenyl)-2-cyclobutyl-1H-imidazol-5-yl)pyrimidin-2-ylamino)propan-2-ylcarbamate, trifluoroacetate salt | 0.00023 |
| 1BU | (S)-Methyl 1-(4-(4-(2-chloro-5-fluoro-3-(methylsulfonamido)phenyl)-2-cyclobutyl-1H-imidazol-5-yl)pyrimidin-2-ylamino)propan-2-ylcarbamate, trifluoroacetate salt | 0.0010 |
| 1BV | N-(2-Chloro-3-(2-cyclopropyl-5-(2-(methylamino)pyrimidin-4-yl)-1H-imidazol-4-yl)-5-fluorophenyl)-2,6-difluorobenzenesulfonamide, trifluoroacetate salt | 0.0010 |
| 1BW | N-(2-Chloro-3-(2-cyclopropyl-5-(2-(methylamino)pyrimidin-4-yl)-1H-imidazol-4-yl)-5-fluorophenyl)methanesulfonamide, trifluoroacetate salt | 0.031 |
| 1BX | N-(2-Chloro-3-(2-cyclopropyl-5-(2-(methylamino)pyrimidin-4-yl)-1H-imidazol-4-yl)-5-fluorophenyl)propane-1-sulfonamide | 0.00011 |
| 1BY | (S)-Methyl 1-(4-(4-(2-chloro-5-fluoro-3-(methylsulfonamido)phenyl)-2-(2,4-difluorophenyl)-1H-imidazol-5-yl)pyrimidin-2-ylamino)propan-2-ylcarbamate | 2.04 |
| 1BZ | (S)-Methyl 1-(4-(4-(2-chloro-5-fluoro-3-(methylsulfonamido)phenyl)-2-(4-(trifluoromethyl)phenyl)-1H-imidazol-5-yl)pyrimidin-2-ylamino)-propan-2-ylcarbamate | 0.002 |
| 2A | N-(5-Chloro-3-(5-(2-(2-cyanoethylamino)pyrimidin-4-yl)-2-cyclopropyl-1H-imidazol-4-yl)-2-fluorophenyl)methanesulfonamide | 0.00008 |
| 2B | (S)-Methyl 1-(4-(2-tert-butyl-4-(3-(cyclopropanesulfonamido)-2-fluorophenyl)-1H-imidazol-5-yl)pyrimidin-2-ylamino)propan-2-ylcarbamate, trifluoroacetate salt | 0.00027 |
| 2C | (S)-Methyl 1-(4-(2-tert-butyl-4-(2-fluoro-3-(methylsulfonamido)phenyl)-1H-imidazol-5-yl)pyrimidin-2-ylamino)propan-2-ylcarbamate, trifluoroacetate salt | .00061 |
| 2D | (S)-Methyl 1-(4-(2-tert-butyl-4-(2-fluoro-3-(1-methylethylsulfonamido)phenyl)-1H-imidazol-5-yl)pyrimidin-2-ylamino)propan-2-ylcarbamate, trifluoroacetate salt | .00078 |
| 2E | N-(3-(5-(2-(2-Cyanoethylamino)pyrimidin-4-yl)-2-cyclopropyl-1H-imidazol-4-yl)-2-fluorophenyl)methanesulfonamide | 0.004 |
| 2F | Methyl (2S)-1-(4-(4-(2-chloro-6-fluoro-3-(methylsulfonamido)phenyl)-2-cyclopropyl-1H-imidazol-5-yl)pyrimidin-2-ylamino)propan-2-ylcarbamate, trifluoroacetate salt | 0.005 |
| 2G | N-(2-Chloro-3-(5-(2-((1-cyanocyclopropyl)methylamino)pyrimidin-4-yl)-2-cyclopropyl-1H-imidazol-4-yl)phenyl)methanesulfonamide | 0.035 |
| 2H | N-(3-(5-(2-Aminopyrimidin-4-yl)-2-cyclopropyl-1H-imidazol-4-yl)-2-chlorophenyl)-2,6-difluorobenzenesulfonamide | 0.0010 |
| 2I | N-(2-Chloro-3-(2-cyclopropyl-5-(pyrimidin-4-yl)-1H-imidazol-4-yl)-5-fluorophenyl)-2,6-difluorobenzenesulfonamide, trifluoroacetate salt | 0.0010 |
| 2J | N-(2-Chloro-3-(2-cyclopropyl-5-(pyrimidin-4-yl)-1H-imidazol-4-yl)-5-fluorophenyl)methanesulfonamide, trifluoroacetate salt | 0.087 |
| 2K | N-(2-Chloro-3-(2-cyclopropyl-5-(pyrimidin-4-yl)-1H-imidazol-4-yl)-5-fluorophenyl)propane-1-sulfonamide, trifluoroacetate salt | 0.0040 |
| 3A-2 | N-(3-(2-Cyclopropyl-5-(2-(methylamino)pyrimidin-4-yl)-1H-imidazol-4-yl)-2-fluorophenyl)-methanesulfonamide, hydrogen chloride salt | 0.578 |
| 3B | (S)-N-(3-(2-Cyclopropyl-5-(2-(2-hydroxypropylamino)pyrimidin-4-yl)-1H-imidazol-4-yl)-2-fluorophenyl)methanesulfonamide, hydrogen chloride salt | 0.028 |
| 4A-3 | Methyl (2S)-1-(4-(2-cyclopropyl-4-(2,5-difluoro-3-(methylsulfonamido)-phenyl)-1H-imidazol-5-yl)pyrimidin-2-ylamino)propan-2-ylcarbamate | 0.00013 |
| 4B | (S)-Methyl 1-(4-(2-tert-butyl-4-(2-fluoro-3-(propylsulfonamido)phenyl)-1H-imidazol-5-yl)pyrimidin-2-ylamino)propan-2-ylcarbamate, trifluoroacetate salt | .00038 |
| 4C | (S)-Methyl 1-(4-(2-cyclopropyl-4-(2-fluoro-3-(propylsulfonamido)phenyl)-1H-imidazol-5-yl)pyrimidin-2-ylamino)propan-2-ylcarbamate, trifluoroacetate salt | 0.00016 |
| 4D | (S)-Methyl 1-(4-(2-cyclopropyl-4-(3-methyl-5-(1-methylethylsulfonamido)phenyl)-1H-imidazol-5-yl)pyrimidin-2-ylamino)propan-2-ylcarbamate, trifluoroacetate salt | 0.00096 |
| 4E | (S)-Methyl 1-(4-(2-tert-butyl-4-(2-fluoro-3-(3,3,3-trifluoropropylsulfonamido)phenyl)-1H-imidazol-5-yl)pyrimidin-2-ylamino)propan-2-ylcarbamate, trifluoroacetate salt | 0.00108 |
| 4F | (S)-Methyl 1-(4-(2-tert-butyl-5-(5-chloro-2-fluoro-3-(propylsulfonamido)phenyl)-1H-imidazol-4-yl)pyrimidin-2-ylamino)propan-2-ylcarbamate, trifluoroacetate salt | 0.00053 |
| 4G | N-(3-(5-(2-(2-Cyanoethylamino)pyrimidin-4-yl)-2-cyclopropyl-1H-imidazol-4-yl)-2-fluorophenyl)propane-1-sulfonamide, trifluoroacetate salt | 0.00013 |
| 4H | 3-(4-(2-Cyclopropyl-4-(2-fluoro-3-(propylsulfonamido)phenyl)-1H-imidazol-5-yl)pyrimidin-2-ylamino)propanamide, trifluoroacetate salt | 0.002 |
| 4I | (S)-Methyl 1-(4-(2-tert-butyl-4-(2,4-difluoro-3-(propylsulfonamido)phenyl)-1H-imidazol-5-yl)pyrimidin-2-ylamino)propan-2-ylcarbamate, trifluoroacetate salt | 0.00012 |
| 4J | (S)-Methyl 1-(4-(2-cyclopropyl-4-(3-(propylsulfonamido)phenyl)-1H-imidazol-5-yl)pyrimidin-2-ylamino)propan-2-ylcarbamate, trifluoroacetate salt | 0.0010 |
| 4K | (S)-Methyl 1-(4-(2-cyclopropyl-4-(3-(methylsulfonamido)phenyl)-1H-imidazol-5-yl)pyrimidin-2-ylamino)propan-2-ylcarbamate, trifluoroacetate salt | 0.0080 |
| 5A | (S)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate | 0.0004 |

A375 Cellular Proliferation Assay

A375 is a melanoma cell line that harbors the B-Raf V600E mutation. A375-luc cells engineered to express luciferase is plated to 384-well white clear bottom plates as 1,500 cells/50 μL/well in DMEM containing 10% FBS. Test compounds, dissolved in 100% DMSO at appropriate concentrations, are transferred to the cells by a robotic Pin Tool (100 mL). The cells are incubated for 2 days at 25° C., then 25 μL of Bright-Glo™ is added to each well and the plates are read by luminescence. The concentration of each compound for 50% inhibition ($IC_{50}$) is calculated by non-linear regression using XL Fit data analysis software. wild type and V600E B-Raf.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound of Formula I or II

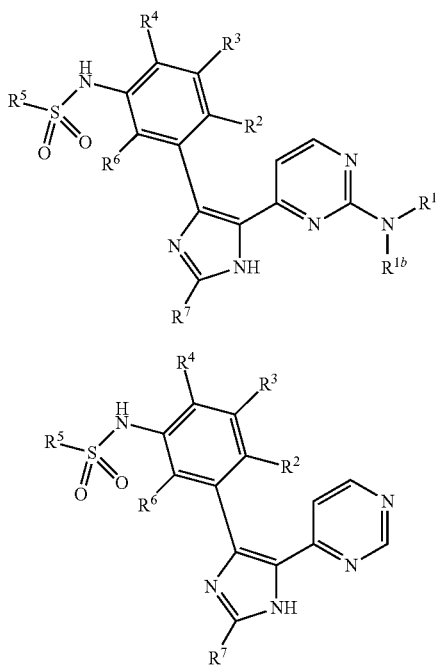

wherein:
R1 is (C1-C3)alkyl optionally substituted with cyano, —C(O)NH2, or hydroxy,
  or R1 is —X1NHC(O)OR1a or —X1NHC(O)NHR1a, where X1 is (C1-C4)alkylene optionally substituted with 1 to 3 groups each independently selected from (C1-C4)alkyl and halosubstituted(C1-C4)alkyl, and R1a is (C1-C4)alkyl or halosubstituted(C1-C4)alkyl;
R1b is H or methyl;
R2 is H or halogen;
R3 is H, halogen, (C1-C4)alkoxy, (C1-C4)alkyl, halosubstituted(C1-C4)alkoxy, or halosubstituted(C1-C4)alkyl;
R4 is halogen, H, or (C1-C4)alkyl;
R5 is (C1-C6)alkyl, (C3-C6)cycloalkyl, (C3-C8)branched alkyl, halosubstituted(C1-C6)alkyl, or halosubstituted(C3-C8)branched alkyl;
R6 is H, (C1-C4)alkyl, or halogen; and
R7 is (C1-C6)alkyl, (C3-C6)cycloalkyl, 1-methyl-(C3-C6)cycloalkyl, or (C3-C8)branched alkyl;
or a pharmaceutically acceptable salt thereof.

2. The compound of claim 1 wherein said compound is a compound of Formula I;
or a pharmaceutically acceptable salt thereof.

3. The compound of claim 1, wherein:
R1 is —X1NHC(O)OR1a, where X1 is a (C1-C4)alkylene optionally substituted with 1 to 3 groups each independently selected from (C1-C4)alkyl or halosubstituted (C1-C4)alkyl and R1a is (C1-C2)alkyl or halosubstituted(C1-C2)alkyl;
R2 is H or F;
R3 is H, halogen, (C1-C2)alkoxy, (C1-C2)alkyl, halosubstituted(C1-C2)alkoxy, or halosubstituted(C1-C2)alkyl;
R4 is H or methyl;
R5 is (C1-C4)alkyl, (C3-C6)cycloalkyl, (C3-C5)branched alkyl, halosubstituted(C1-C4)alkyl, or halosubstituted (C3-C6)branched alkyl; and
R7 is (C3-C6)cycloalkyl, 1-methyl-(C3-C6)cycloalkyl, or (C3-C6)branched alkyl;
or a pharmaceutically acceptable salt thereof.

4. The compound of claim 2, wherein:
R1 is —X1NHC(O)OR1a, where X1 is a (C1-C4)alkylene optionally substituted with 1 to 3 groups each independently selected from (C1-C4)alkyl or halosubstituted (C1-C4)alkyl and R1a is (C1-C2)alkyl or halosubstituted(C1-C2)alkyl;
R2 is H or F;
R3 is H, halogen, (C1-C2)alkyl, or halosubstituted(C1-C2)alkyl;
R4 is H or methyl;
R5 is (C1-C4)alkyl, (C3-C6)cycloalkyl, halosubstituted (C1-C4)alkyl, or (C3-C5)branched alkyl;
R6 is H, (C1-C2)alkyl, or halogen; and
R7 is (C3-C6)cycloalkyl, 1-methyl-(C3-C6)cycloalkyl, or (C3-C6)branched alkyl;
or a pharmaceutically acceptable salt thereof.

5. The compound of claim 4, wherein:
R1 is —X1NHC(O)OR1a, where X1 is (C1-C2)alkylene substituted with (C1-C2)alkyl and R1a is (C1-C2)alkyl;
R2 is H;
R3 is H, Cl, F, or methyl;
R4 is H;
R5 is methyl, cyclopropyl, ethyl, propyl, isopropyl, sec-butyl, isobutyl, trifluoromethyl, or 3,3,3-trifluoropropyl;
R6 is H, methyl, F, or Cl; and
R7 is t-butyl, cyclopropyl, or 1-methylcyclopropyl;
or a pharmaceutically acceptable salt thereof.

6. The compound of claim 1 wherein R1 has the following formula (1a)

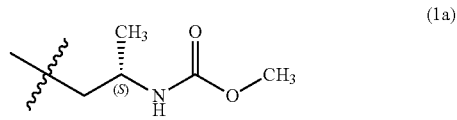

or a pharmaceutically acceptable salt thereof.

7. The compound of claim 5 wherein R1 has the following formula (1a)

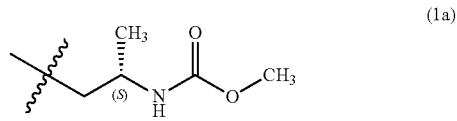

or a pharmaceutically acceptable salt thereof.

8. The compound of claim 1 wherein said compound is a compound of Formula I

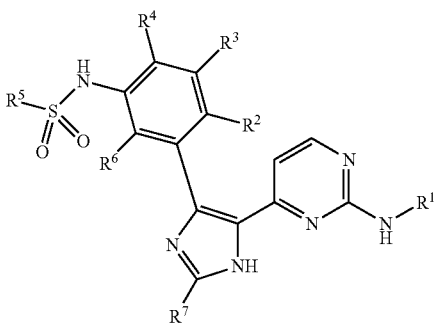

wherein
- R1 is —X1NHC(O)OR1a, where X1 is (C1-C4)alkylene optionally substituted with 1 to 3 groups each independently selected from halo, (C1-C4)alkyl, and halosubstituted(C1-C4)alkyl, and R1a is H, (C1-C4)alkyl, or halosubstituted(C1-C4)alkyl;
- R2 is H or halogen;
- R3 is halogen, (C1-C4)alkyl, or halosubstituted(C1-C4)alkyl;
- R4 is H, or (C1-C4)alkyl;
- R5 is (C1-C6)alkyl, (C3-C6)cycloalkyl, (C3-C8)branched alkyl, or halosubstituted(C1-C6)alkyl;
- R6 is halogen; and
- R7 is (C1-C6)alkyl, (C3-C6)cycloalkyl, 1-methyl-(C3-C6)cycloalkyl, or (C3-C8)branched alkyl;

or a pharmaceutically acceptable salt thereof.

9. The compound of claim 1 wherein said compound is a compound of Formula II;
or a pharmaceutically acceptable salt thereof.

10. The compound of claim 9 wherein
- R2 is H or F;
- R3 is halogen;
- R4 is H or methyl;
- R5 is (C1-C4)alkyl, (C3-C6)cycloalkyl, (C3-C5)branched alkyl, or halosubstituted(C1-C4)alkyl;
- R6 is (C1-C2)alkyl, or halogen; and
- R7 is (C3-C6)cycloalkyl, 1-methyl-(C3-C6)cycloalkyl, or (C3-C6)branched alkyl;

or a pharmaceutically acceptable salt thereof.

11. The compound of claim 10 wherein
- R2 is H;
- R3 is Cl or F;
- R4 is H;
- R5 is methyl, cyclopropyl, ethyl, propyl, isopropyl, sec-butyl, isobutyl, trifluoromethyl, or 3,3,3-trifluoropropyl;
- R6 is F or Cl; and
- R7 is t-butyl, cyclopropyl, or 1-methylcyclopropyl;

or a pharmaceutically acceptable salt thereof.

12. The compound of claim 11, wherein R5 is methyl, ethyl, or cyclopropyl.

13. The compound of claim 1 selected from the group consisting of
- (S)-Methyl 1-(4-(4-(2-chloro-5-fluoro-3-(methylsulfonamido)phenyl)-2-cyclopropyl-1H-imidazol-5-yl)pyrimidin-2-ylamino)propan-2-ylcarbamate;
- (S)-Methyl 1-(4-(2-cyclopropyl-4-(2-fluoro-5-methyl-3-(methylsulfonamido)phenyl)-1H-imidazol-5-yl)pyrimidin-2-ylamino)propan-2-ylcarbamate;
- (S)-Methyl 1-(4-(2-cyclopropyl-4-(2,5-dichloro-3-(methylsulfonamido)phenyl)-1H-imidazol-5-yl)pyrimidin-2-ylamino)propan-2-ylcarbamate;
- (S)-Methyl 1-(4-(4-(2-chloro-3-(methylsulfonamido)phenyl)-2-cyclopropyl-1H-imidazol-5-yl)pyrimidin-2-ylamino)propan-2-ylcarbamate;
- (S)-Methyl 1-(4-(2-cyclopropyl-4-(2-fluoro-3-(methylsulfonamido)phenyl)-1H-imidazol-5-yl)pyrimidin-2-ylamino)propan-2-ylcarbamate;
- Methyl (2S)-1-(4-(2-cyclopropyl-4-(2,5-difluoro-3-(methylsulfonamido)phenyl)-1H-imidazol-5-yl)pyrimidin-2-ylamino)propan-2-ylcarbamate; and
- (S)-Methyl 1-(4-(4-(2-chloro-5-methyl-3-(methylsulfonamido)phenyl)-2-cyclopropyl-1H-imidazol-5-yl)pyrimidin-2-ylamino)propan-2-ylcarbamate;

or a pharmaceutically acceptable salt thereof.

14. A compound selected from the group consisting of
- (S)-Methyl 1-(4-(5-(5-chloro-2-fluoro-3-(3,3,3-trifluoropropylsulfonamido)phenyl)-2-cyclopropyl-1H-imidazol-4-yl)pyrimidin-2-ylamino)propan-2-ylcarbamate;
- (S)-Methyl 1-(4-(5-(5-chloro-3-(cyclopropylmethylsulfonamido)-2-fluorophenyl)-2-cyclopropyl-1H-imidazol-4-yl)pyrimidin-2-ylamino)propan-2-ylcarbamate;
- (S)-Methyl 1-(4-(4-(2-chloro-3-(ethylsulfonamido)-5-fluorophenyl)-2-cyclopropyl-1H-imidazol-5-yl)pyrimidin-2-ylamino)propan-2-ylcarbamate; and
- (S)-Methyl 1-(4-(4-(2-chloro-3-(cyclopropanesulfonamido)-5-fluorophenyl)-2-cyclopropyl-1H-imidazol-5-yl)pyrimidin-2-ylamino)propan-2-ylcarbamate;

or a pharmaceutically acceptable salt thereof.

15. A pharmaceutical composition comprising a compound of claim 1 and a diluent, carrier or excipient.

16. The pharmaceutical composition of claim 15, further comprising an additional therapeutic agent, wherein said additional therapeutic agent is selected from the group consisting of an anticancer compound, an analgesic, an antiemetic, an antidepressant, and an anti-inflammatory agent.

* * * * *